US008232070B2

(12) United States Patent
Lee et al.

(10) Patent No.: US 8,232,070 B2
(45) Date of Patent: Jul. 31, 2012

(54) DNP63A GENE AND SCREENING METHODS OF ANTICANCER AGENT BY USING IT

(75) Inventors: Hyun Sook Lee, Seoul (KR); Jung Hwa Lee, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 56 days.

(21) Appl. No.: 12/532,267

(22) PCT Filed: Mar. 30, 2007

(86) PCT No.: PCT/KR2007/001576

§ 371 (c)(1), (2), (4) Date: Sep. 21, 2009

(87) PCT Pub. No.: WO2008/120831

PCT Pub. Date: Oct. 9, 2008

(65) Prior Publication Data

US 2010/0105045 A1 Apr. 29, 2010

(51) Int. Cl.
*G01N 33/574* (2006.01)

(52) U.S. Cl. ...................................................... 435/7.23

(58) Field of Classification Search ......................... None
See application file for complete search history.

(56) References Cited

U.S. PATENT DOCUMENTS

| | | | | |
|---|---|---|---|---|
| 6,479,285 | B1 | 11/2002 | Vize et al. | |
| 6,946,256 | B1 * | 9/2005 | McKeon et al. ............... | 435/7.1 |
| 2002/0094547 | A1 | 7/2002 | Burstein | |

FOREIGN PATENT DOCUMENTS

| | | |
|---|---|---|
| KR | 2007/0055855 | 5/2007 |
| WO | WO 2004/048520 | 6/2004 |

OTHER PUBLICATIONS

Lee et al., "Regulation of ΔNp63α by Tumor Necrosis Factor-α in Epithelial Homeostasis," FEBS J. 274:6511-6522, 2007.

Nalepa et al., "Drug Discovery in the Ubiquitin-Proteasome System," Nature 5:596-613, 2006.

NCBI Genbank Accession ID AAG45610, Jan. 4, 2001.

Yang et al., "p63, a p53 Homolog at 3q27-29, Encodes Multiple Products with Transactivating, Death-Inducing, and Dominant-Negative Activities," Mol. Cell. 2:305-316, 1998.

Zangen et al., "ΔNp63α Levels Correlate with Clinical Tumor Response to Cisplatin," Cell Cycle 4:1313-1315, 2005.

International Search Report from International Application No. PCT/KR2007/001576, dated Dec. 11, 2007.

* cited by examiner

*Primary Examiner* — Laura B Goddard
(74) *Attorney, Agent, or Firm* — Clark & Elbing LLP

(57) ABSTRACT

This invention relates to a gene encoding ΔNp63α and screening methods of anticancer-drugs thereof, more specifically a gene encoding ΔNp63α and a protein which is transported from nucleus to cytoplasm by contacting with potential anti-cancer-drugs in an epithelial cell carcinoma, a recombinant vector comprising said gene and reporter genes, and carcinoma cells comprising said vector. Also, This invention relates to high throughput screening methods of anticancer-drug comprising identifying the transportation of ΔNp63α protein from nucleus to cytoplasm by contacting with potential anticancer-drug in a carcinoma cell.

3 Claims, 2 Drawing Sheets

SEQUENCE LISTING

```
<160> NUMBER OF SEQ ID NOS: 3

<210> SEQ ID NO 1
<211> LENGTH: 107466
<212> TYPE: DNA
<213> ORGANISM: Homo sapiens

<400> SEQUENCE: 1

atgttgtacc tggaaaacaa tgcccagact caatttagtg aggtaaggat tttagatttt      60

agcactccat ttagagatgc tttttaattt ttatttttgt aaaaaaactt acgtatttgc     120

ggttctcggt cacccaatgt aatgttttgc aaattgtata taggaatctc cttttcttgg     180

ttaatgtttt ctgtggtggc tgtaagattt tttttttttt attaagtagg agatgaaaca     240

gtaggagaag atgaaaaaga aaatctgggt gacattatgt atttgaaaaa ataatattca     300

ggagtttata aaatcacttt ttagaaaaac agactcagag agcagatcac actctgctag     360

atacattgca atgaatcctc tgatgggtat tcatgtacca gtaagaaaaa tcagttgact     420

gtgtcttaac ttcttagcat agttctattt ccagacttca tcctaaaagc aaatgaagct     480

tttttcaaaa taatcaggtg agatttttta aagccatctt cgtttttaag tctgtcaatc     540

cagagaccca cctaaatcca gaaggggctg tgataacgtt tctgtcgtct ggagggtgac     600

ttgtactttc acgtgtgatg acaaataaag ttattttgga gggatgcatt gttaaatatt     660

tatacatgca tacatgtaaa tgtgtattat agcatacagg attttattta agaaactgat     720

tatttgcatt tctgatctct tctcagcaag tttgtcttag gtatttaaac ctgtgcaaag     780

ggataaaaaa aaaaatcctg aagagactgt aaggctttga ggaagtttcc taaggttgag     840

ggaggtctaa caacaatatt agtttacatt cctcagaatg gggcagctgt gttgacacta     900

atcagattgg gttgtggtgg ggagtgttgt ggagagagag agttcggtgt ttcagataaa     960
```

```
aatgcttgca ggtgagtgct tggaaaagtg gactagagta ctcaaattga gctccttaaa   1020
aatcaaaaca aaatgcatag tattccggtg cagaccgcaa gaggaagagt agagcagagg   1080
gctgcgaagc agggcctgtg ctatcgtatt gaccacgcta ttgtctagac tcctgaactg   1140
tgtaaataca acaggggaaa tatcgagtta tctaaagaag gaaaaggaag tgcctatttt   1200
tctttaaaac attcaagcag gcttgcttgt cctcagtaga gaaacttgag tttcttgttt   1260
tgcagttata ttgaaagtta gcttaaaatg ttaccaattt gtttttaaat aggattagct   1320
tttaagatct tcttgattct attggatcca attttgtcca gttttaatca ttcagaaaat   1380
gatctgtcca tcatgtcata cctgagtttg tttgtcttta ttcatgaact atttcacaca   1440
cagtatttat aagccgccta ggatcttgta agtcaaatgg gagaagcaaa agtctgttca   1500
ttgatatctc taagtgaagc acaaggttga tgtaaagtgg caagaaatga ttaattttag   1560
gttaaatata atgtcgtgaa agaaagcaat tgcattaatg ttgtgattag aggatatttg   1620
tagaaattat ttccttttat ggaggcaaaa gagtcatatt gtatgtgaga atatggcatg   1680
cttatgaaag aaaatagttt tatacacagg ttttagtttt tcacaactct aggtaaatat   1740
gtaatcaaga gctacaaaag gcatcccttg tctgttttct attggaatgc tgctaaggtc   1800
gacaaaaaat atctgtaaaa aacatggctg cacttcccta cctttctatg tctttttgca   1860
tgttgcctgc atgactttca tatccttcca ccagtgcatg tattaggtta taatttcatg   1920
gcttgacttc cattctatta cgtacgaaca actttctttc tgtacaggat tatgctttca   1980
tatctagtcc tctgttaaaa ttcagtgcta catctgagta tatgaaatgc ctggcaccac   2040
atggctctga gaaccatgaa tttaatataa aagttataat gtatagggat ttatgtttat   2100
tagtaactgt caatacagaa aaagcaatct actattatta cacaagaatt gttaaacatt   2160
gggtagatta aaaatgaaaa aggcataaaa ctccctgtaa gagtgaaaat tatttaaaaa   2220
ctataatcca ttctttgact tcaaataaat ttatagttta atttgctagc aatttctttg   2280
agttgataac tcaaaaacta tataagaaca ctgttccttc tctattcctt ttcccacaac   2340
ttttgaattc ttccccaacc cttagcagat ttggatttgg gggagctgct aattaacagg   2400
aaatggtccg gaagggagga gaacacaagc aggatataac aggcaaggct gaaggctcta   2460
cccttgggta cagcggagag gccgcaagca agctccactc cccagtgcca gactaggaaa   2520
gacagagcct ctgggaatgg tctcagactt ggagatagag agggtcaaaa taaaggaact   2580
tcttcacaga tcaagtttta acttcaactt tctggcaaaa caaaacaaaa caaaactggg   2640
ctgtgtgtgt ggtgtaagtg tgtatgtgtg tgagtgggga ggatctcaaa ctccttctta   2700
gaaagagata tttactaaaa ttcctcatcc ggggttttag atgatgaagg aaagacactt   2760
tggtaaatgg gttacagtat tttcgaacta aatgggaaat caaggttcat atatggaaac   2820
acctcatttt acaaatcagg gttaatgatt tttctttctg tagttgagag agctatatgt   2880
atacgatcgt gttcccttta ctcagccact ttctttttaa taccaaggag agatgggatg   2940
attcatagta gatgctccaa aacagtttcc atgaagaaca gttgtacaaa gccagttgaa   3000
tgcaagaaaa aaagtgtgga gacagcagtg taaactccct gtagtccagg tcattctcac   3060
ttaattgact tctttgtctg cttggtctag ggaaaaaaat ctgtcctgtc ctagtactat   3120
ttctactgac tcaaccattt aaaagatatg ggtgtgagtt ttctattgat agttaataaa   3180
tgtattaagc tgtcccatgt tgtacttctg agctagttag catcatagga aaaagcacag   3240
tgggtgagaa gcagaagctg catttttaat tagtgtcagc caggtcgtat tcctcactcc   3300
atgctgttgc catagattgc actacttgtt ttacagttgg ttgtcctcga gcccagaggg   3360
```

```
aactaggaga aagacatctt agatcacaga tcacagatca taccttcctt cactactact   3420
ggaaaaaaaa agattttgag acaataaatc acttatcctt tacctcgata aggaaaaccg   3480
tgtttggttt ggtttgcttt ttagaagagc agtgattctc aacagcatgt cacacgtaca   3540
gcagaaagca tcaatggatg tctacatttt ctagagcaac caaaaaaata ttggtttctt   3600
tttcattata cgtacatttt ctgaatgcaa agttgctaaa acattcctca atgactatgg   3660
acagaattta gattctgcgt tctgctataa agggagtata tatctaatgt catgagattt   3720
taaaaaggga tttggatcaa acagttgaga aatatgttac cacaaataca ccctggtttt   3780
ctttgatgtg catatgattg ctctgggtgg aatctgagct ggtagaatag aggggcacag   3840
gtaaaaatcc ttccttccta gtataacttt tctctcccct tgaatatttt taaatttcta   3900
attgttttat gtcaacaaat agaatgaata caggtaacaa aaagatactt ctgtgaaaaa   3960
caacttgatg atttccataa tttataagtt ttactatttt gaagataaaa aattgttaaa   4020
cccaagtggg cgctcaattt tctttagatg tatgttgagg aaaatgtcag ttgactaata   4080
tagcattatt gtccagtgcc aatttagtgg aacctacaaa tggtatccaa tagagtacta   4140
cattttgggt ctggaagagc atggattcaa gtgtcaaggt gaaacatttg attcaaaagt   4200
taagttttaa atcttattcc taatcttaag gacacaattt gtgggcccaa gaaaatagtg   4260
aaatgtggct tattaatggg ccaccactct aaacatttta taatttttac ttatactttt   4320
tgattaagtt ctatgttgac aatattcatg aaaagtagta ttgagaaaga gaaacaggtt   4380
agaagaagaa ctgactgact cttaaaaaaa tgtttactga gcatcaatta tatgtaaaat   4440
ggtatatagg atctaaaaat aattaagaaa taattcctac actaagaagt ttatagttct   4500
ttgggggaat gagctaagta tgcatgcaat tataatacag gagagatttt aagtgtgtga   4560
gcaagataat ataaagcatc aaagggaaag agagtccatg atgtaggaag atcaagaaag   4620
tctatatgca tatgtaagat gaagctgcac ttggaaggac agatggaaat ttccaagttc   4680
tagaaatata agaaggaatg aggattttag gtgaagaaat aagcatcagc aaagggaagg   4740
ggggtgagga gtgaatgctg gtacactcag aagcatcaaa tagttcaaat gcaattgaaa   4800
ttatgagacg atcaggaaat aaagttggaa atgcaagata gagtggctca gagatgacca   4860
taacactgag aggagagtac atttatcata gtgacaatga aaagccatgg aaggatttcg   4920
aacagaagaa tggtgtaatt gtgtaattgg agctctacta gagagcacag ggagaataaa   4980
tggctttgct tgagattgcc tagaagtatg aaaatgcatc tctctgcatt gcacattggc   5040
tgcctgtttt gcagaaatat ctatcagttc tcttggatct ttggaaggat acgcatggat   5100
tgtttctaaa gtctcataca acctgtgtat tttctgccca gtgctctttt taatagctat   5160
ggtccctgcc atagacaaat tgggaactac tggtcttggt ttgtctttat ttatgcctgc   5220
tattctagca taattactaa tagcacacct tttcactttc aaaactgtcc catttagaag   5280
ataaattata tagtcactct gtaaagaccc cattctttat ttcattctct tccacacact   5340
aacactccac cccaaaatga aaaagtagta taaatttggc tgtaagccag acacaatgat   5400
tttgaagtac cagccacaaa tcattttgat tatttccccc actaaaggaa acacttcctt   5460
ccaacccaac agttactgaa aacttataat agtcactgtt atatgcactg tgaggaaaga   5520
agaaattagt aattcacagc ttctagcctc cgtgaattca taatctgagg gagttatgag   5580
gggttcgtaa atgactccag tataaaacag aattggtaaa agatatccca agttttgaaa   5640
gagtgaaatc gagttcaaac tgtttatgat aaaggtaata ttttatatgg tttgagaact   5700
gaaattcaga tgtggcgtga ggggaggaaa gacattctat gtagagggga taaaatttat   5760
```

```
aaaaatacaa gggaggactg tgccagacaa cgtgaaggaa catagtatat tgatttaaaa   5820
agaaaatgtg ttggtttaaa cactgatatg tatttactat ttatgtcaaa atggaacgct   5880
tttgtagaaa tagcaacaaa agttaattgg aatattgatc tcactaagag cggaaaccta   5940
tatgtgtttt aaaagtgtga ccagtgttca gaattcgaga ttcaaaactt cacatactct   6000
agggatgatg agtgacatct tgcaggaagg aaaagaaaat tagcccgaat gattccttag   6060
gctgaaaagt tgaggattac cttttcccgt tccttagact tctacagagc cagatatggt   6120
gtcctatcat ttatagggac ttagtaatga cattttaaaa cttatcaaag ctaggaacaa   6180
aattcaaact gactctctgt gtttattatg agttaatttt atttattaaa tagtcgtctt   6240
agaaatagga ccagaagtct tttctctggt cactgctcta aatgcaaata gtaatcctga   6300
agctgaatat aagacattta ttcagaatga gaatcccagc tgggaaataa ataacagagc   6360
agagggaaat atgaatatcc catttaaaag ccaaccccac caaataaaaa atttaagata   6420
ttatctttgc cataaaattt ttaaatttga ctttgggaca aggatacatg tgtaagatgt   6480
aatatgtaaa gataaatatt gggagaagac atgtcttttc ccacatcaat atcctccctt   6540
tccacagcct ccttcatcac ttccatctca cccaagaaga ccacgtgggc aattgaagag   6600
ataataacag ggcaggggag ggtaggccat ggtgggagga aggagtgaac cagtgacttg   6660
atttaaagcc aaagggagtg gataagagaa ctgggcttca agataaataa ggagacatct   6720
aagctagtac tcatttcttt ctcttttttt taccaaccta atcctccact ttcaaaaagt   6780
agattttgaa agcatcaaat gttaacatat gattgtccta cagacattag gggaaacagt   6840
gaggttccac taaatacaac ctccttaaaa gaaataagta gttcaatgaa gtgtctgtaa   6900
aatcttttca aaagtcttac tttatacttc cccacagttg atttccttag ttggtctgag   6960
aatatagcac ctatactatt caaaaactat tcttttccat tttctgcaaa aaaaattata   7020
aatttcttat ttctaagttg attgattgca tgtttgatat ggactaactt tattctgatt   7080
ttgaagttgt tcaagcttct ttttcaaaga caaagtacaa atggatcatt gtatggattc   7140
gagctgagat ggcttcacca gataatgttc acctgtcaat ttaaaattca gtcactgggg   7200
ttaagataga gcacatgttg gttctaggtg agggaataac tggcaagaat aaaacatttt   7260
tggaatgtta gtgaatgtgt gtgtaacgta aattgatatt tcatgcaaaa cttgtaatct   7320
gaattgcatc ttgtctgtat ttcttaaatg gcaaaaagat ttccttataa aagctgaaag   7380
agggaatttt gagtcaagct gtggtgtgtt gccagaggcg gaaatttatg aaacactctt   7440
gtcagctatg ctggaaacac tacaaaagaa atagttctac tttcttattg gtgctaaagc   7500
cactaatagg tgcagtttag tataataccc ctatgagaat taccaccccc gaagtgagct   7560
tgccttggaa ggaactctgt acaggcattt tctttttcct tttaagcttg cgcaaaacac   7620
ccaaaggggc catttcccac ccagccagtg atctttctca agtttattct ttctcagatc   7680
acagagacaa tggggaatat gccctgttta ctcaaatcag tctggattag tgtcactcta   7740
ttgatggagt cagaattaaa aggaaaacca ttaccctctc aaagggcaac atcagatgtt   7800
tggggaatgg cgtgattact tttaaataga ccgtgtgaga ctctgtcacc agactgaggt   7860
tgaggactcc acaagacaca cttgaagaga aacagtaaca ctgggtgagg caggaagctc   7920
ttcataagcc ttaggcctgg gaaattattt caacagacaa tcccaaaatg cttgaaaggc   7980
tgaaaatcag aatggtgaga cttcagagaa gagggctttt ctgccttctt tctttgctcc   8040
aacacctcac ccccatatat ttatctccag gtcaaatcct ttccagtcat taagccctgc   8100
tggggagaaa cttaaccctg aaaaagctct cagattcccc cattcaggat aacacttcca   8160
```

```
tcctctgaac tcttttactc tgtttcttcc tcattgctct ctgtgtacac cagatccttc   8220
ctccctatcc tttgactgaa gaccctggga gggtagagga tgtgttatgc ttatctctgt   8280
atcccctaca gggccactca gtaatgttcc ctgaatgtga tgaggacatg catctgttgc   8340
tgttgcttga agggatatct tcacctagga atatatggtg tattgtatat acttaaaagg   8400
ctgtttgtaa ttgacttgtg cacaaaaata aataaagcga gccgacatat tatacaagcc   8460
tcttctatct atatgttctg caggtaaacc aaattgtgtc attttccttc acatcttgca   8520
ggtcatttgt ttttgctgtt tgtttgtttt aataagccca atattatttc cattatcttt   8580
taaatagcaa gaaagttttt gaaagacagg gcagatgatt tgtttggtat caagtaatta   8640
gtgtaaagta tgtgctgctt tcacataatt gattactcac aaggacagag aatgtgtttg   8700
attaaaaaaa agtcttagat ttttatcttg ctttgcaggc cctttttaaa agtgtttacc   8760
tgtgtctgca ctgttccctt gattcagttt atcccctgca gttctctctg tcctcaccag   8820
agatggggga agtttgatct gggtgaataa gcttgatgat ttgcaaacgc tctctccttt   8880
taattctcta tagtgttatc actaaaggat gtctgagaaa cctcaaagca atttttctct   8940
taaacgtggt attccaactt ttggttttgc tcatatcttt tataatagga caaatagaat   9000
aaaatgaata agacgagtgt cttttcaaaa gtaaggcatg tcttctgcat agctcaaaac   9060
ttgagtttta ttttgcagtt aaagtgacag ctgagaggaa cactccaatg ttatataggt   9120
caccatatct aattgcaaag taatcactaa aaactttaat tatctcaaat ataacttaaa   9180
aagtagcaat cagcaaagaa tttgacaaac aaaagcaaat tagaactcat gaaacagtgt   9240
tccccgcttg aatgcctata gtctaacaag attgagtagt acactccttg tttcaagcct   9300
cagttttcca gttgcaaata aaaactagtg tttcaacctt taagtgtttg ttatattgga   9360
gcataaattt atatcatttg caagaaagga tttataagtc tgataaacta taatctcagt   9420
tccttaaaca tacaatcaca aactgttaat tatggcttta ttctaaactg aattctggct   9480
aactgggcat aaaatcatgg aaattaggca gggagggacc aattttgtgg cctatctacc   9540
agaaactaaa tgtctttctc taagcttgtt tctgggtggt ttcttttcaa agcaacctgc   9600
atttggccat gtgctccatc agtaggaagt gaataattat atgaccacaa agatataggt   9660
tcttattgct gacctaggtg cattcgaaac aaaacctaga ccatcaggtt aaaaaacact   9720
gccttggcac aaaagtgtgt atgtgtttgt tttaaggaag tagaagctca ttaataaact   9780
tcccagctag gtgtgagcta ccaagtatta ctcattgtat tgtgagtgac aggactggct   9840
attctgctac tagttcccat aaaagctgaa gctaaaagca caattcccac ctaccaagac   9900
aaagctaaac aaaaagtaaa gatcatagag attatttagg gatgcactat aacatttgtc   9960
tgacagtagc atataaagaa atgaatcaaa tttggacaca gactcaggat aaaataaatg  10020
atcagttgta ttagaataaa agagatactt tctgcaagta attttcatgt tgaagtgttt  10080
tgcatttatt cttttaagaa ctgtctcctg agcatctatt atgtttcagc cattatccca  10140
ggtattgggg attcagtact aaacaggcca gatatattct ctcattaact tattgcctag  10200
cagagaagac caacattttt aaaagtttat acatatagtt aatttctatt atgattatat  10260
gatacaaatg gaaagtgcta tgaaaatgtg gaacaaaaga gaataatctg tctgaacagt  10320
caaagaagac ttctgggaga tgacatctga gctaaaggtt gaacaaggaa ttggaaaaca  10380
gctggcatgt gcaaaagact tgaagactga aggagttagc ctttaaaaaa atgaagaaag  10440
ttctatttgg ccagagcaga gtttcaaata gtgcctcaca ggccacgtta aagacctgag  10500
gcctttattc taggagaata gggagctgct caaggaattt aagcttgaga gtgacaagat  10560
```

```
cagatttgca atgcctttca agtggtagtt acaaggagtt gggtctctga ccctttgcaa  10620
ttatacccat tctaactaag aatggggaaa cttttatatc ctgtctttaa tgagtaaaaa  10680
aaaaaaaaag aaaaaaaaag caaataaaag aggtgcgctt ttcttgattg taactttcag  10740
ataaaaattc caggcagaaa tgtgagtgat tcctatttac atgcagtcgg aatgaaagct  10800
acttaggaaa gcgggttccg gagccagatt tactggttcg acatccaggc tcttctcact  10860
accttgggcg agttacttaa ccttgtggag cttcagtttc ctcatctata aaacatggat  10920
aaaacatgga tattaatgcc atgtgtctca tgagaaataa gtaaaaccat gcaaagcact  10980
tgaacactct aagacacata cttagaactc cgtaagagaa ttaataatag tagaagtaat  11040
tgctcatttt cttttataga ggggatggaa gatggatgat aagtagattt cagagtttta  11100
aaatttattt ttatttttat tttttgctcc tgatagtcac cattacttta ttgaaactga  11160
tatgtcttca gtttcatgtc atggtaacga aagcttattt tctgtgataa aatgttaatc  11220
acatttaatc acccgttgtt ttaagtcaca atttaggata tgaactagac aaatatacta  11280
ccaacattat ttaaaaaata tttttaaact cactttccaa accaaggatg cattactgct  11340
gggcttctaa aggcagtatg gtatgcttaa cataaagatg gcttaacatt cattgaagaa  11400
ttttattact atgtactttc ttcttttaat attaccatat ctgctatata gagctatgaa  11460
aacatattga ttgctataga ttgaaaatct cttcaaacat attttgattc acttggaata  11520
aactgaaatt ctgaatattt cccctaatac cagaattaaa aattattaaa tattaaaatt  11580
ctatcctgct ttctgcttag tttgatactt ctttgatata aaatgataat aattccttca  11640
gaattgggat gccttctgat tttcattttg ttgagttgtt atgattatta taggagtatg  11700
tactaaaata atataatttt aaaatttatt tttcttaatt gagttctaca cattttaatt  11760
tagctgcatt tggatcaagt tttaatttta ataccttttcc cacttcctgt cttttcaaat  11820
gttgtgtcaa atgtttgttg acattgttgt ccacctgatc agacaacttt gtatttattt  11880
ctctcacctg ccgttggggc ttctagagct ctttctccta aattatggaa tcttggcact  11940
caaaggaatc ttgacacttt gtgtcagaac acaggacatc tagtgaactc tctgcttaca  12000
gtcttgatag ttttgggtgc gtttaaatac tttattctta tattttgttc tttgtatgag  12060
tatatattaa gtattcactt tttatataat tttagaaaac aaaatgagtg acatatttta  12120
tacctaataa aatctggttt tgagaaaaat gtgatgctac ataaattctt cggttggaaa  12180
gatggtgttt taacttgacg tttgaatacc aatatatttt cttaacctgg agtagaacac  12240
tgtaagtcaa ttgtgtttaa ttctagcata aaagaaacca tcattctctg aggtggggca  12300
ggtggcagaa gacgaaaaaa tgacaagtat gtctccctta ggcagtgctt gttgaaaagt  12360
cactatcctg ctgatatttg gggatggaaa tgtagtactc tctgctaaag cataattgaa  12420
tgaatgcttt taaagccagg gtcatcaagt aaagctgttt tctttaccca tgagggactg  12480
tagaatgttc ataaaagcac ctccgtgaag cctcaggtga aaggtggtta tcagctgagg  12540
aaactgtatg tgctgcctaa aatgttttag atttctaagt ttggtcaggg acatctgtat  12600
agagagagaa cagttacctt agaaaactgt tttgaatgtg gtcttatagc attgttttaa  12660
cgtagcttca cagatgagga tggccataag tcacagaatg ttagaactgg agatccctct  12720
cattgaatcc tcaaattcag tctcctcaat tttacacaga ctttggatta tggtaaacta  12780
aggtccacaa gttgttcagc taccttgccc agaggtacac agcacactag tggcagtgtt  12840
gggacttaga ctccatgtaa agaagtttaa gttcagaatt cttttgcatc actaggatcc  12900
atacaggagt gtaaggagta ctgaagcgtg ttcaatcccc tagcctcatc caccagtcac  12960
```

```
tcatggatta taaatacaat ttcttccaag tgaaatttgg gaatactgtt gtatcttgta  13020
acaaaggtct ggttgaatcg agataagtta tgattatata tcccaacagt aatctcttct  13080
acccctgatt tggtccctat cccatttttt taataacctc ttactatata ttgttgacta  13140
ttgttgctat agtgtcataa atttactatt atagatagta atatctgaaa aaggggacat  13200
tttaaaaaat tctcttggcc aggtgtggtg tctcacacct ttaatcccaa cactttggga  13260
ggctgaggca ggtggatcac ctgaggtcgg gagtttgaga ccagcccgac caacatggag  13320
aaaccacatc tctactaaaa atacaaaatc agccgggcat ggtggcacct gcctgtaatc  13380
ctagctactc aggaggctga gggaggagaa tctcttgaac ctgggaggca gaggttgtgg  13440
tgacccaaga tcgtgccatt gcactccagc ctgggcaaca agagtgaaac tccatctcaa  13500
agaaaaaaaa ttatctttta cagataaatt ggtggagaga gattttcaaa aacacaaatt  13560
ataggtaaat acctatttct attgcattgg tcaaatagct tcattggaat ctctttttga  13620
tgttaaatac ttttatagga aaataattac gtcatcaact ttaagtaaat ataaatccaa  13680
ttatttaata ttgagttata gcaatatata ttgacacagt tttgtttctt catggtgaaa  13740
acagtttgag attcagctcc tgggtatctt tatacctacc atgcaagctg tatgtttcag  13800
aatgccctca gggtgttcta tgattgcagg gaatatgtcg agtccatgtg accaaggcgt  13860
acttcatcct ttctgtgatc agatcagcta gtttgtgagg aacctgaata tatcacaact  13920
acaaataaat tttccagggt ccaaacagtg attcttctat ttcaaagtta ttttatagaa  13980
aatgaagcat ctgtttggaa tcacaggaaa ttattttact ttataagttt cacagtagat  14040
atcacagaag ttgtgttcat ttttgccttt atgttttgtg gaaagaatac tgcctctttt  14100
ttcagacatg ctgagataga tatataatgt ttccattcac tcattatttg ggtgtctgca  14160
gggtatgtta aggttattcc aaaatcaaga tgccttgtgt ttagaaaggg agaacctgct  14220
tcctatttca tttcagatac gccaataact tttgttacct aagaaataca tgcatatggg  14280
acatgggggc tctatggagt tcttccaaag gccgttttta tggctgatct gaaagtatag  14340
tgttctaatc tctgagactg actctttgac ttgtcattgt cagtaagcat tgcattaaca  14400
tcccagcata ttacacattt ctctcctctg ttatggaatt attggctgta aataaggcaa  14460
gaggtactgc tccctttacc ccgccagatt tgctgtgata gaaaataagg gatagatatt  14520
attcacttga cctgggacag cttcatgggc ataaaaactg caattggtca cacagggccc  14580
tatcttagaa aagcaccatt ctttgtttaa tgctttgcta tcatcatttt gaaattctta  14640
atctatgaac aagaggttct gcattttcat cttgcactga gcactacaaa ttgtacaaat  14700
tgttttgctg gacctgtctg ggtgacactt gttcttcttg actataatgg ccagcccttg  14760
gcttccaatt gtaccctgtt aacacacgcg atctttcttt aaatcaaagg aataagtgaa  14820
taagaatatt ttctttaaac tagatatttt aaaaattaac ttctgaagaa tgaatttatt  14880
gatttttaat aaactaagaa aatatgtaaa tggatttcca gtcattcagt tctgactttg  14940
gtgggtttgt tgttgtttct gttcatttta agctaacatt caaagttagt agtgtcagtt  15000
ttacgctttc caggaaaaga caacggagta tactacttgg cttatatttc tgtaaagtat  15060
cacttgagaa gcgtttcaac tgaaatgtgt tttcccactt tgattgtgtg tagtaggctg  15120
atttctcatc aatcctaaga aatatacctt tatgttatat taattgagga tttagcattg  15180
gtaacaaatc ttgtttttct tacgtacaaa atctcccttg ggactggata taatttaaaa  15240
ctatgacgcc taaaagtaga tccatcagta cccacattgc tattcatgac ttttgaaata  15300
cagtttctgc ttctttgttg cttctcaatg gttcagtctt tctatcattc caaaggactc  15360
```

```
ttgtgactcc tcagtaaatg gaattttccc tttcttttcc ttaatatcca taaaatcagt  15420
ttactcaaga aattatatag cagtatacag cctaaaccct ttctcaaaat tgtcactagc  15480
ttttcttatt cattaaaaca ttttcatctc attacaaatg atttcttcct ttaaaatttc  15540
ccagaaagta tggcctctgt attttctgct gctcagttta aacacatcat caaagacaga  15600
taattattaa tgtcatatga gcataacagg agatttataa atcagaaatg tattttctgg  15660
gaaccaactt tcaagttagt caggtaagtt ttattaactt cactggtgaa gtcctaggat  15720
aaagcagtgc ctagatcagg cttgtttacc cttggcctta tatggcacca aacactgttt  15780
caggacagtg gaagaacagc ctgggaggcc ttcggccttg gccagccttg ccgaggcccg  15840
ctcaccagga gaaataggaa ggaaggccag tgagtgtgca aaggagcatg gcttattttg  15900
aggtcctgaa ggccagtgag tgtgcaaagg agcatggctt attttgaggt cctgctgatt  15960
gcaggccaac aaaacaatgg caggatttga aggaagaaag tattgcaaca gagtcaccgt  16020
atactttgaa ctgcaaaggg agactgagga aatgttgcct caaggccaaa aaccctggct  16080
caaaacacag gttcctcagg tgactcagag gcagaccaag ttcaccaagt caaggacatt  16140
ttcctgctac ccccctgggg agaggggcct tcaccaaacc accctggaca tggatctcct  16200
gctgttcaga acccacccaa taaacaacag aagcaaacac ttttttttt ttttttttt  16260
tttttttgcc ccttacacgg aattgtccct ttttgtaagt ccttgttgaa ttgaagagtg  16320
tttgctcact ggcttttaaa gtgtggtccc aaaacttttt tcttcgttta tattgggtta  16380
aaaaaaaaat caaggggccc atgcgtcttt gttctcatcc aagcccacaa ttagttagct  16440
ggggttcctt ctgtgtagct agaagcagga gggaaggggg tggcccagca ggcattttac  16500
tgcctgcgag aaagtgctgt gagtttcttt gtcctttttg tcagggacgg ctgcctccct  16560
aattgtactg ctgtagggag gcacgtgcct ttgggagcat tatctgattc ctacaggacg  16620
ttcaagagtg ctttgtatac tgacccttaa cttgaacaca aagaatatct tttcaatccc  16680
cttccgaggc tgttgcctca ggcttggata cctaagagct ttagttcagc cggggtatgg  16740
accatttata tgggctcagg ttttattttt ttgtccccta gttgtcttac ctgcagtttg  16800
gccacacctg ccgggagaga aagctgaaga tggtgggtaa gtggtggata gcagctatag  16860
aagtcagaag ggagagaaag cgagacaaac agctgctctt gtcagcatgg ggataagtgt  16920
aaagagatta atagttattt gaagagcaaa tggggacatg gcattcggca gtggaatgcg  16980
aatgcatgaa tgtaatggaa tgagcatgtg actattaaca tttagacaaa tgcttcctgg  17040
actgaatgga atggcaaagc ccacttctcc tccccctgtg gaaaaaaaaa agttcaataa  17100
aataattaaa agtttgaaat ttttaaaaag ataagcctag ctcctatttc tttgtaagtt  17160
tgttcttctc tatagtttta cttaatctgg gactctcagt tacatttcaa ctgaagagct  17220
aggcctattt cctttataaa atatgtacga ataggactgc cttaatcttg cttttgattt  17280
ttttttctca ttcattaggt tgatgaaaca agatttctat gtgtcggaag gttttacaaa  17340
ggaaaagcaa ctgtaccata agctggttgc ccctttgttc attttggctc aggtttagaa  17400
atgatgatag gctgatttgc ctactcaggc tgacagtttt gatggcatgg acagagccct  17460
gaagtcagaa ccagaagatt cagcaccgaa agccccagtc attgtgttag cggatgctag  17520
ggcaaatgct ctacctctcc gatagtaata tagtcaagtt ttttgtagag taaatgaggc  17580
aaaattaatt tattctttca taaatatgtt cttgagtact tttactctgt gcttgggccc  17640
attcacatag aagacataaa aacgtttggc agaaggaaat acatgagcta atgtattttt  17700
gaattatatt gaccatagaa ttttcttcat aagtagttgg tatttctctt acaaatgttc  17760
```

```
tactctagaa aagaataaat ttctattaag aaaatgaaag aacaaataaa aaagaattag  17820
accagtttgg atgatttact agcatgttac tttttaaaat acatagttgg gtgtccctaa  17880
ccccgctacc catgatcctc cagtctttgt gaaaccagtc cttagggggc tgggtggtac  17940
actcttggta ctctgggaca gaatgcagaa ttgcaagatt aagagaaaat tcgaaggtca  18000
tttgattttg ccccctatgc aacaatttaa cacttaaatc ccctctggaa catacctatc  18060
aagtggtctt tctcattttg tgtaacacgc cccaaccccc accaacaacc tcaaaatgga  18120
atagcaggca gtatttattt aaagacttcc taagcagcta ctgagcactg ggaacgtttt  18180
gcctagtttg tgaataagca tatactctac tttcaaatgc tctgtaggaa gtcagtctcc  18240
agaggtggca catagagctg agtgatctgg aaaagccgtt acaaacacac acatgctcag  18300
acttctcttg ttttctctgt ttaccaaaaa tcaacggttt tactttgaat gtgaagtgct  18360
tccgacgtga ggtccatctc tgtagaatgc attcacccat ggatgccttt ttttggagca  18420
atgatccgtg gcttcagcgg ctaatattgg ggtttctggg tgtccttgca gccacagtac  18480
acgaacctgg ggctcctgaa cagcatggac cagcagattc agaacggctc ctcgtccacc  18540
agtccctata acacagacca cgcgcagaac agcgtcacgg cgccctcgcc ctacgcacag  18600
cccagctcca ccttcgatgc tctctctcca tcacccgcca tcccctccaa caccgactac  18660
ccaggcccgc acagtttcga cgtgtccttc cagcagtcga gcaccgccaa gtcggccacc  18720
tggacggtaa gagcagcggg cacgcacata cctgaccccc caagtccaag gatgggcttc  18780
accacgtccc agggatttct ccccttccc agtttagcga ttccatgttc atggtggaaa  18840
atttgtcttt gaatatttaa tactgaacca gagagagaga aagtgccagt tagtgggaaa  18900
agtcccaatt taggaaccaa acgtctgcgt tctagccagc tcctggcaac ttcagtcagt  18960
gtgttcctgc ctgcttcaca ctgttgtatg tgaaagttca tggcaaggta aagagcgctg  19020
tgccaacaag aagtatcata atcatgggat atgtgtttac agtctccaga acgtgaacgt  19080
gtttaccagt ctcattcttg taaagaagta agtgtcacat taagttgtga ttttaaaaac  19140
tgagtaaaat aataaatata gtgttataaa aattaagaaa ataaaatccc atttatgaag  19200
gaaggatgaa tatgtttata catgtaggta tcaataaatt ataatttatc agtaaattgt  19260
ataatgtctt ataaattact atttataatt tatcagtgaa ttataattta ttgatatgta  19320
tatatttatt taatttggaa acattctttt cgaaaagaaa gcctttaaat agacatatca  19380
gagccctgaa ttagtccaaa gaaattgtta aagaaaaatc tttctgcata taagttttct  19440
aaggaagcat ggaattttct tttcataaat taggaagata caagaattag tccaaagaaa  19500
ttgttttaaa aaatctttct gtatataact tttctaagga agcatggaat tttctttttc  19560
ataactagat ccaagaatat tttattttga agtgtatttt gaaatgtatt ataacaagaa  19620
taaagctcaa gtataaaaga ggacacctac aaagttggtt ttaactggtt gatcaaagaa  19680
tgttcaagac caaagtggta tgtttgtcaa acaacttaat caagaccaaa gtggtatgtt  19740
tgtcaaacaa cttaatgttt acatggatta tagaaatgct tccaaatatc atcatcttaa  19800
taaaaagtag ctttagaatt gttttgacag ttttttccct ctttgacaaa tggatttctt  19860
tggaaagcat ttctatgttt atgttatata tagtatctag ttcattccag cctttagttt  19920
gtatagttta taaaatgatc ggcatgccta agacctatta cactctaaca tcatttcaca  19980
tccatttcct ctttttcacc tcatttcttt gtgaagtacc caggacaagt tttataactt  20040
ccactgtgct agtgaggaaa gctgaagaag ttggaggtta agttaagagg catgcctaaa  20100
cttacagaaa cttgtgtgta gctgggcctg tttttcattt ctgcttccct ctcactggat  20160
```

```
tgtatccttt ctttcaacca ttttatatca ggatctccca aaattgtcta aaaattaatg  20220
ttattttagt tctttcctct tgtggtttga gaagtaattc tccggtggct catatttcaa  20280
ctgtagagca tgaacatcag cttaaaactt gatctctcct ccacgtgtta cttatcaatg  20340
gagtcataat ccttagtttc ctttactttt ataattctgg aggcgatgga tactgcaggt  20400
gagtaaactt agagtttata ggcttcaaat agttggttga ttgatctaag tagtatcttg  20460
ctaaagagcc actagaataa ccattttata aatggagcac tgatatctct taggtcacca  20520
accggacatt tacagtcacc agtcttcaaa gctaacagtt actaattcag tttactccgc  20580
caggtctcca ttatattagg agtcagcatg tctgatgaga tgatgggcat attagggctg  20640
ctaaatgaat aatcgctttt tttccctgta aaatttttag aaaaccatgg ggatgaatct  20700
tgatgtaagt tcaacatcaa attagttatc cttccctgtc ccttcctcac tacctcctca  20760
tatagaaatc ttaaaagccg ggcgtggtgg ctcacaccta taatcccagc actttgggag  20820
gctgaggcag gcagatcacg aggtcaggag ttcaagacca gcctggccaa catagtgaaa  20880
ccctgtctgt actaaaaata caaaaattag ccagacgtgg tggtgggtgc ctgtagtctc  20940
agctactggg gagactgaga aaggagaatc acttgaacct gggagacaga ggttgtggcg  21000
agctgagatc gcaccactac atgtgatctg cctgcacaat agaacaagag tccgtctcca  21060
aaaaaaaaaa aaaaattaaa gttattttca ggtttagcat aatcctaaac catcactcaa  21120
agcccctctc tcagagaagt caattgtctt actcaaaaag ttggagatct ctaccaaaat  21180
gttaggttta aaagaaaaga aaatattctg gtacactggt aaaatttcct tacatgtgac  21240
agcagtaata tcagtgccct gacaaaaggg atacactgtg gtgatgagaa aaaggcactg  21300
actgagagac agaaaacctg gattatggtc ttgatcattt atgcaaactt agccaagtca  21360
cttgatcttt ctaaaattca gtctgtgcct cagatgagaa agaggatgag aatggagaaa  21420
cctactctgt tttcttaagg tgagatgata gtattaataa ttaacgtaga aagtttttag  21480
aagggctttg gttcgcatcg atatattgtc tgccattcat gagtgtcctt ggttaagtga  21540
ttttgcttct cttggatttt tgttcacttt tctgcattct acctataaat tttacaatca  21600
ggtttctact cacatatcac atggtaatta tatttttatt aaatttcttt cttgttcaca  21660
accaggctta tttcaggccc agttcatttc ttctaaatta gggcacttga acccttatct  21720
gagcagctac tgagatcacc taaaaagatg taagttcttc gtcatggata cctgcatctt  21780
agcttctaat tctttgagcc aaattatata tcctcatgtt tatacacaga cttcccattt  21840
taaaaagtat tttttcatat atttatctta gttgagcctc ataaccaagt ttgtaatccc  21900
cagttttata gatgaggaaa cttgaagatg taaaggtcac atggctaata accagccaag  21960
gatggggaag aatccaggcc tccctcaccc taattcaagt ctctccacca tcctagttag  22020
actgtttctc ctctggtttg agaccaggga ggggcataca ggagcaggca gtgcctgtgt  22080
agtttggagc ttgcctctta tgtcccagag tccaactggt aaagaaattt tttgtgcctt  22140
attatacaac acctatttct taggcatttg tgcattttag agcaattttt caaaataaaa  22200
tgctgcattt tagaactgcc cacaaactga aagaaacaga agctgctgtc attaggggga  22260
gatcatgctt atcgcatagt cttctggtaa ttctttaata aaaatatttt tagtaccatt  22320
ttatcacttg caatcctttt atgtcaagtt ttctttttta acttttctgg ttttaccctc  22380
aggattactg tcaaaatata gctaatatat ttaaagtata tgtgcatttt tcctttgcgt  22440
ttctgtgttt taaataacaa atgtgattat gtttccagtt ctacaaaaat atggtattta  22500
ttttaaactt ctttcaatga aatgaagtaa aataagacaa catttttcat cttctctgtt  22560
```

tcacacacac atacatacac gacaaaccaa cgtttacttt agtttcagat tttcttattt 22620
ccacaattta attgatacta gttacagagg cctatcattt aatataatgt agtgctggtc 22680
tagcattgta gttgggaatc gttaatcata ggacagttga aagaatggta gtgtggagat 22740
ggcaagaaac ttaaattcag atttcaactc ggaaacttac taacagcata tggggctttc 22800
accaaaaatt caatctctct aaacctcact tttctcacct acaaatggga acaaatggga 22860
acattaatac tttccttatc atgaggatta cttcatgtaa acatacctat tagcacctag 22920
ctactcatat gctcccaagt gtttattggg tctgaatttg aatttcttcg gttcgtgagt 22980
tcattgtagt tttgttgagg cttcgacaaa actttagtac ctttagttgt actaaaggta 23040
ctcatttgag agaatgaaaa ataaaatttc aactaatgtt ttttcttaaa gcttttgggc 23100
tattaacatg catactttat agagggactg tgatactatc cactatccaa atatatgaat 23160
agatggtata gggtgataac agcctctcct gcatgcagac ttctgcaggc tggctctgct 23220
gctttccgaa gcctgcccaa gcagatgtag gctctccttg ccagtgcaag gagaggccct 23280
ttccagattt aagaacctgt tgatttttga cattcgttcc tcatttttaa tctgatgctt 23340
catgatggga atgccttttt gtattctttg tgttaaggaa taacagtggg ccttacttat 23400
ggcagactca agatattaat gtataatgac aaactactgg aagcaacctg atcagtcacc 23460
cgtgaaaaac tagatggcat gttataagca ataaccatac ggccattaga aagaattctc 23520
tgtactgata aggaaagctt tgggagttgc tggtgaggga aaaagaaagc tttctgtggc 23580
acctgcttga gaattgagag tcctggtaag gaaccccact tgtaggggcg gtgtttcttt 23640
gtgctcccct ctagtgatga ggcttcttgg tgaacatagt tcagtctgtc ttgattattg 23700
gcctcacaca cctttgccag ttggagagct atttttcacc gctcatgaca cgagagtact 23760
ctctgtgtgc atacgccatg aaaatcctca ggttgttttt ttttttgcat tgttttgttt 23820
tttaaattgt gttcagactg aagtaaggac cctacccttg ggacatagga tcacttttg 23880 ctgttgtatc tttctcctgt cattgacctc aaggtcttgt atggcagact ccctgatcta 23940
gtgcccagca caatgtccag cacacagtaa acctttaata aatgggaagg aacttttttt 24000
ctctcataat taaaggaaac aattgtagtt cccagcagga gccctcaatt ctgactctga 24060
ttgttaactg cccgtgaatt tgttccctgt agccttcacc catgatttat agagagtgtt 24120
cttcctttgc ctttcttaac catgccagct tcgtgtcatg ttcagagctg tggagaattt 24180
gacttgagca agtggagaga ttagggaggt ggcgtttgaa aggggaacag ccagttcccg 24240
ggagagttcc attgatccca gcatatgggt cttggtctcg caagctcact ccctttggct 24300
ccgcaggcag gctgagatgc gcgcctgcgg cccaccctcc ctgtcatcag gttacctgta 24360
atgtaagact tttagaaaaa ggctgccagc tctgcagaaa tctaatgcaa cccagccaat 24420
tgcgtggccc tctggaattt agagactctt aagaatagcc catcaaagga caagatgtac 24480
agacaaactc ttcgatggta aataggattt atcagttttc tttcacagtg gaagcacttc 24540
ccccattaaa gtctgagtct catctggggc ttgatctaat cttacaattc agtggctgtt 24600
agattttatt ggtgaggggc agaagtcagt agctcgtgcc actggtacat gtgttcgtgt 24660
ttatcataac aagataattt ttacttcttg ccatagctgt ttcataaatt atgtgagatg 24720
tgtatcaggt gcctttttgt gccactccca tgatgaagaa aataatagca ttgagcatat 24780
taatctgtta tctaaactat ttcttagttc acagagtatt gaggaagaat gtactaaata 24840
aagtgcttag agatttttgg tgatggttca agtaacttac ctctaggttt tggatttaaa 24900
atgaatattc attgtaaggc atgcttccga agagttgttc cctcatccag agcagaataa 24960

```
ctgaatcagc gttcttgcct gagttttaga ttgactctag gttaacgtat tcgtgatgag  25020
ccagtttaat ctaatctaag gcttatcagc ctcccatact attttgagtg atttgttcac  25080
tgcaccgtgg agtgtctatt taacattaaa ctgatcttga tttattgcat gtgaacatta  25140
taaaaactat tgattttaaa aatgaataat ttaaataaag cttatatttc ttttcctact  25200
acaaagagta acagcaaaaa tcctctgctt ttcccttttc ttctttctcc ctattcttct  25260
cctcttcccg catttcttct ccccttctt tctactccct ccttctcttt tttccttcat  25320
ttatgttatt attgttagtt aatttggttt tgtaggtatc atcagctaca tggtatcttt  25380
ctttattttt ttttactata gcttcactct tctccataaa ttaatatgga gaacatgata  25440
tatatcaatc accgtggaaa tttttatcag gattaaatta tcacaacctt ttcatgtaac  25500
aaatcacttt ggtgaataat aatgggctgc tttagaggta gcaaacccaa atgtcattgg  25560
agtcagggag gtagcataaa tgagccgaat gataagtaca gaaactgtgg caaaagagct  25620
tatatactgt atctacaagg acatctgctt tacaatccca gactgttgtc acaggggaaa  25680
gtagacctag tattaaaata tttaaaatat taaattaatt atcacaatat taactcttaa  25740
atattaattt ttaaaagagt aactagaaac ctgggtttgc atgtaatatc ttcatatctt  25800
aaaatgatga tactaattca aaaaaaagtt gtaaaacact acaggccaaa caaaacagta  25860
cacaggctgc atgccatcct gtgcaaggtg ttaatggtaa caaggggaga ttactaaatg  25920
tttaaataaa ttaattggaa gttagttatt aaaataacta aaataactgg aatcagcatc  25980
taagagaaag gttactagtg ggtatatttt attcacaagt aataattctt tattccttta  26040
caaagtcata tagattaatc tcttgctgca tttaactaag caatacatta tcagaacata  26100
tttttctcaa cttgttttct tacagcaaat gacctttctg cttctcattt ttatatcatt  26160
ttatatttta aaaatctaat ggcatgcagg attggatact tggaagttta ttgtttgttt  26220
gttcctgtgc ttatcattag agaattatgg aactctgtaa cttaactcct taaaattggc  26280
caaagttgca ctcagaaaag agctttgaga tttaaagggc ttctaatcaa ttttctcagc  26340
ttactaacag atagcttact tttaattggc acatagtgtg ccagaacaaa aatcatctga  26400
taattgaagt ataaagagaa aataatgtca taagaacttt taatgactct ggaaaactat  26460
atcattaagc tcaaaagaga tcccttaaaa tgaatgcaaa cttaaaatcg gccctgagtg  26520
atgtgtacca tttattgtgg gattgtcgct cttggtacat ttccatacat gagctttgca  26580
cattctcctg ttcgcattcc ccaaattagg ttatttccat aacgtgacca agtctatgca  26640
attgttccta cccgctttgg taaagggccg atgtatgttt ctcatgaaaa gtcctcagca  26700
gttacagctg tcatatcgcg agtaaaacca tataactata tataaaaacc ccctggtttt  26760
atattagcag caattggtat gtctagtcag gtcactgtga ctgaaaggag acttgagata  26820
atgtagcttt ccaacaactt ccaattcttc aaaattaaag aagagtttat tgtagaatag  26880
aaagatagaa agataattct tcagttcttt gaagccctgc agacattttg tagatatgga  26940
atggttttta gaatgatgga tcctgtaatg aggcacacag aggcgtaaag gtaatgatct  27000
tagtagattt ctctcttgtg gtttttagta atgatcatga ccttatcatt aagcccccca  27060
cgtgaaattt aaaagaaaat ttgatagtag tcagagaccc tagatctaat ttattgtgag  27120
gtaaattagg gagggattct gactttacag atagaatgag acttctcatt ttagtctgaa  27180
tttaataatg aagattcatg tgggggaaaa aaaaaaccct acaacttgcc accttgttat  27240
tgtatcagaa aggcctgaaa acagagcagg gaccttaatt gctaattgtg ttagtaccaa  27300
cctttcaagt tcattgatta aataggagtt ccttcttgga ttaatgccta agtttttatt  27360
```

```
tttgttttgc ttcatgtgct gttcagccag tatcatctgc attgaatctt ataaaaacta  27420
taatgaataa gttgaggaga ctatttctaa agacttttcc tttgagtggt ttccaagttg  27480
tattaaataa gaagactaat gattacttaa gggttctcat ttgaatttga gaagacatct  27540
gacaggctcc tgaggagtgt gactcattaa gtagaatacg ggactcagaa ggacaacttt  27600
ggggtactaa caagctatat gaactggggc aggtcttttg tctctgtctg tatgttaaat  27660
gagtattata atttttactt ggcaagattg ctgtgaggct taattaaagt ttataaagtg  27720
ctttgggagc ctgagagatg aagctctaaa aacataatat gttattatct catcctggat  27780
ttttgttttt agatttactt gcttgaatct gtatcataac gatgcttaca attcaggcag  27840
ttttctgagg tttttttattt ctacaaagac atgaaataaa ataacataaa tatataagtc  27900
cctagacatt catatgggat gaaaaaatta cacataattt ttttctgatg taaaagagtt  27960
tcttcttaaa aaatgtttaa ttgaatctta tatctgttaa ccagctttat tttttaaaa  28020
gcatttcagt gttttattcg taacattttt gcagaaccag taaaaagttt taaaatgcag  28080
tcatctttac tgggtcatga gaagaaaaat ttactccatt taaaaaatgt aaatacttat  28140
ttaaatgtaa ataaatatgc gcatttagat atatataaat ataaatatat tactccaatt  28200
gaataacaat ggaattaatt tacagtaatt agaatttgat aatttgggct tgaaagatat  28260
tcctttcttc tatctttctg ccttactttt ttcttctact gtgtgttcat ttgagatttt  28320
catatttata aaatataaaa atgtatatag agccctggag ttaatataaa ttgccttgaa  28380
aattcttttt attcctactt tgtattcttg aaagaaaaat catgttttcc cataagaaca  28440
gtgtcataat tatggataaa atttctgacc aagctattgt catcaagtaa gtaatagata  28500
tgtttaactc tatgtcataa aagcaaagct attaccacca taagccagta taattattgg  28560
aaataacaaa atgattctca ttgtcatata aactttgctt aaatatttta tatgccttga  28620
catatatgta ttaagtttac ttataaaatg ttattttat aaacttatct agaactgact  28680
gctattataa taaatacttt taacattttg acatgccata attttgatcc atttcatggg  28740
gaataatttg agaagcctat gtttctcaaa attttcgtag gaaaattaga atggatactt  28800
gtataatata ttcctgttac taggaatgat gcttaaaaaa attctatagt gtaggtcagt  28860
cttcatttta agcaattgaa tccattttta atgatattac ttaagaattt tgcttgtaag  28920
aaaaaaaact gtatctgatt gaatttgaaa atgtagtttt ggagtgtatt tactcttcct  28980
gcctgatacc ccactcccca aaacagagta gtcttgagga aataaaaggt cctcaaaggc  29040
agctagatat gagaagagtt tgaattgcta atggggaaac ttctagacct ttgccttgat  29100
gttagaaaag gaatttgaga acatgattta tgtgttagac ccagagtttg tctttaaaca  29160
caattcaagt ttatcacctt tcttataacc tttctataca aaaccatgga tttagtgaat  29220
aaagcatttg gaagacggtg gatagttgat agataaagca gattgaccaa catgtaaaaa  29280
tagaaagtgt tttcatagta ggaatttgga ataacttttt ctatattccc atagttagaa  29340
tggatgccta gaaaatgtat ccttattgtg atgattaaaa atctcttttt gaactaagac  29400
acgtaagata gtaacctctt tctgctttgc ttattctccc acccaggctg tgttgaagtt  29460
atataagtat aagcaaatgt gcactttttt tttaaatttt attattatta tactttaagt  29520
tctagggtac atgtgcacaa tgtgcaggtt tgttacatat gtatacgtgt gccatgttgg  29580
tgtgctgcac ccattaactt gtcatttagc attaggtata tctcctaatg ctatccctcc  29640
cccctttcct caccccacaa cagtccccag tgtgtgatgt tccccttcct gtgtccaggt  29700
gttctcattg ttcaattcct acctatgagt gagaacatgc ggtgtttaca ctgttttata  29760
```

```
aaatgctttt gtctaatttt gttaccttta agtttagcta cttggcaaat aaacattttt  29820
aatactgctt aagtcaagtc ttttacaaat agaattgtca acatccaaga gttaccaaaa  29880
gatacttcat tctttagatt tttattgttc tttcacagta ctcactggta atggattata  29940
ttttaccttt tttttttttt tttttttttg agacagtctc tcactctgtc actcaggctg  30000
gagtgcagtg gtgccacctg agctcactgc aacctccccc tcccaggttc aagcaactct  30060
ctgcctcagc ctcctgaaca gctgggatta caggcgcgtg actccatgcc cagctaattt  30120
ttgtattttt agtagagatg gagtttcacc atcttggcca ggctggtctt gaactcctga  30180
ccttgtgatc cacccgcctc ggcctcccaa agtgctggga ttacaggcat gagccaccac  30240
gcccagccct attttacttt tatctattgt caatgactac attgaatact tttgtatgca  30300
aatgtaacaa aggcatattt tgcagttatt tatactttat gtctgagaat tatcacataa  30360
tttagcaaac attaactcat ctgtttacct tttgctgtaa aagctagagc aagtgatgta  30420
gatggggaca agaaaatgac tcactcagcc tcagaaccac aaggaactat agacttcttg  30480
cagtctggtt ttctcttcaa aaagcaatta aatatacgac catttgtata agtttccaca  30540
atgcattcat atttcagaac tgatttctta cctagcacgg catggatttc agttataatg  30600
tttctccttg cacaagcatg gtagacatgg ggttagtagg tataagaatg cctctgggaa  30660
caatctttta aggttttata gactcttttc tctcaccact cccccaacct aagtgtaatt  30720
gtcatcttag acactttgag tttaggggtg gagataggga gagcatcatc agaagggaca  30780
aaaggagaaa ggggaagtga aatggtttgt tggatactag tgagtggagc cttttacaga  30840
agtacaatgc acgcatttta catttgttag ttagatgttt tctaagatgg ttttgtagct  30900
ctgatggtat atttttatgg atataaactt ctaatatgag gaagagaccc aaaccaattc  30960
aaatagcatg ttaaaattca atctatctac aatcttcacg tccttgatta ttacattctg  31020
taatctcatg ggtatttttg cttccaaata taaggacata cctattattt ccttcagttt  31080
tctttttagg agagttgact gaactatttc aggaaagaag atgtcttact ttcctttgcc  31140
tagtaagcct tgctgctttt tgaacacagt gcattttctt caaaatatac ccactacttt  31200
aggtggtctt aatgaatgaa taatatgtaa ttgtgtatac ttttctaaaa ttctttgaaa  31260
cttccaggaa ggaaggtctc attaaatatc tatttgaatt ttagtgaaaa gaacaaaaaa  31320
aagcaataac aaattaagac ctttgattca tgtgtactag cagtggtttt attttggtag  31380
ctagtgctgt gatgtaattg aagcagtatt ttcatataga agcatttttt acttttatgt  31440
tctttctact tgttagaagt attcttttat tatggttact tttgaatgta tgtttccctt  31500
gcactaactc agaatacagc ctcacttcac agcgcttaga tttgattcct gcattcatac  31560
tgtttgcatt tgagggtcct ggtgactgca gtaatctcca cctcctccag agccagagag  31620
aaagaaatgg ccacagctac tttgtcatct tttgtcactg gtctcaatag agggtcaagc  31680
gtgcttacca catggaggat gcttcagaac aacaagggaa agaattagag tgttgcctgg  31740
gtactgccca cgctgctata tgaacagtga gagaggttat attttcctaa gcctcgctta  31800
aagcattccc aactaacaga ttttctgttt ctaatggttt gaacttttgt ttttaagttg  31860
ttatttgggc atgtggttgt agggcataga ttatctccta atttattgct ttcttaattt  31920
gacattggaa tttagacttc agaaacaaaa aatgcaatac tttgaattat cttctttcca  31980
taagttcctg atttaaaatg aaaatgtccc cttaactgct aattacgaga tatcgtataa  32040
agcatatgat acttacagta tatctttttt ggttgtttta taagatgaag attacaaata  32100
tgatatttag cacatcctgg ctcttcttga aagcagggac tatggctctt ttactaaagg  32160
```

```
acaaatagtg cctaaggaaa caggagggtg taggagaaag aattcagctt tgtggtcaga  32220
tagacctggg gggttgaatt tcacttctct ctagctgtat ggtgttgggc taaacactgt  32280
ctctagagcg gcttcctcac ctttcaaata gggatgatac tcctttaggt aacgatgtta  32340
ttggtaggat ttgatataat aagtataaag tgcctaaaac aatgcctgta aatggtaatt  32400
tctattagga tggatcatag atttaggatt agaatttaca ctaaacctac cttattcata  32460
gatttgtcca gaatcatagc aggaaatcta ctccataaag tagctctagc ctctggtgcc  32520
tagtagaggt gatgtattag gatagtactt taaaactttt accccaatta agagcagagg  32580
aaaatgaatg gctagattag ccatcctgag ggtttaatct gaaatggtcc atagaagaca  32640
tatcattttc tttctgaaaa acttatttca actttgcatt caaatataaa tatatatttc  32700
aatataggta tttcttcccc tcattaaaaa gtctttaaaa ttgttgttcc aggaagatga  32760
gtagtattta tcttgtaaca ttgagttatt atacccaggc gcactaccag gaacacttct  32820
gatgtacaag tgccttcaat aattgtttca gaagcacaat tttgagataa gttaaagtgc  32880
cctgggaaag agcattgttt atttttggag ccttagccca aaatgactcg gactcatgct  32940
acaaaatgat aacgctcttc atcagttgta tagagctcct tctttatggc cagctttcct  33000
agagatattt tagacttctt tagatgtccc caaaggcaca ataaccacgt aagaagggaa  33060
gccacaggaa ggcagattgc agcagaaaat gaatggtcag ggttctctag gggtggctgc  33120
actgcctcca gtggtggtga gttctccacc tccagagagt gagacaccct tgactcaagt  33180
tttagatgag agaaacaatc aagcagcctc tgaagttccc cttgaattca aattctttgc  33240
atccagaaga gaagtatttt gtgaccagaa agatacagat tgactgcaat tgacctttc  33300
tatgccagac cattggttaa ctgaagagag tagactctcc agacaggcag tggactcagc  33360
ctacaccaaa acacacagca agccttctgt gcctttcccc aggacagtga ctcttctttt  33420
ctctctgaag ctgtggttct atgtaggaaa ctacataggg tgaagctaaa aggtaggatg  33480
ggccagccta tgtagggtaa ggctttttaa ctctatcgca tgggcagtgt gctgacattg  33540
catacttttt cagcacctct tcagatcggt atataaagta gattaacctg acagcagatg  33600
gcggttggtt ggaggggcct gcagtaaagg agagcagttt ggagaatgcc acggcatgca  33660
gacgcacact gtggagctga gcactcagtc ggtgatgtgg ctcactcacc aggggaagga  33720
cagaggtgag atagggcaag agtcagttgc tgaagtcact actccaaagg gctagataga  33780
aaggtaggga ggaggaatgg agagccagaa aaggagccaa aatgattagc tattttacta  33840
gagcaggtct gtcctaaagg cttggctgcc attctctagc tgggaccttg acgaatcact  33900
tcctccctag tgcctcagtt ttcttgtctt caaaatgagg atgatgctac ctatcctgaa  33960
gggttattgt gaggattaaa tgagatgatg gggtgaaagt gatttgtaaa ctaggaagtc  34020
tatcatgcaa accgcatgat agacttcgga tagaggcagc aggtatacct ttcagctttc  34080
tgtcttgcca aatgaacatt tgtatcctct cacctggtgt ccaagatgaa ggtgctggtt  34140
cagtgagata actcttatcc agcctaatct caagacttcc tttcatgctc tctctctcac  34200
acctagcaat aaatgccaaa agcctaatag ccccccaaac cttgatcgtt tcaagaggat  34260
cctttcaaag gaaacctgcc tttcctctct ccttgaggag aaaccaaagc agtccagtga  34320
ataaaattca tatttttctc ccaggctgat tgaaatggct ggccgtggga gcccagggcc  34380
tttttgtagg actgttttat ttatttattt tattattatt attatttttt ttttgagaca  34440
gagtctcgct ccgtcaccca ggctggagtg cagtggcaca atcttggctc actgcaacct  34500
ctgcctcctg ggttcgagcc attccggatt cgagccattc tcctgcctca gcctccccag  34560
```

```
tagctaggac tacaggtgcc tgccaccatg cctggctaat ttttgtattt ttagtagagt  34620
tggggtttca ccatgttggc caggctggtc ttgaactcct gacctcaggt gatccacctg  34680
cctcagcctc ccaaagtgct gggattacag gagtgagcca ccgtgcctag cctggacttt  34740
tccaattagg ctgtgccggg gctgctgtga aactgttttc ctgtgaagac agtgattttc  34800
tccttagggt ggctgctgtc acacggcact gcccctttcc ttataatact tgatcacaga  34860
cacagtaaca tctgtgccta gatcacaagc catacttact caggacgatt ttcctcttaa  34920
agcaccaggg agggagaggc ccttgtcaga attctcacga ctgaatcatt gccatgagct  34980
aatgtctcca gttttatgag tcagtgctgg cccaggcatc ggttttgtag gtttaaaaaa  35040
aaaaaaaaaa agacatgggt tagactcccc taatatcagt agcttgttca gggggaaagc  35100
aaactgagct atcatcagac agcagcattt tagaaatcag atgtttggtt cctctcctct  35160
gtaaggatat agaataagtg gaagaatttc agaattaaaa ataatagtaa taaaagctct  35220
ctgatttgtg cgtgtgtttt gttttgcttc tggcaaagaa ggtaaaatgg tgtgtttggg  35280
agatgaatgt tcttgtaata ggcaagatgt agcttgcagg agaacatctg caacaaaccc  35340
ttattctgca tgagatacag ccaagacctg tttgtgtgtt agtgcctgtt caaacatgtc  35400
taatttttaa aatgatttat aaagttttgg aggaatcacc ttaaaatgtt atttcctcat  35460
ataataggca tatacattca cagcgtggtg gctaaactat acaccctgtt ggagtttgag  35520
cagtgccaat attgagctaa gtgatataaa aatggttatc aatatgaagt agatagaaaa  35580
gtattaggaa tatctgcaat cattcgtgag tctaccgatt aatccagcag caggcaaaaa  35640
taaattatgc tttccacgtt tttaaatgtt cttggtagag aatttatgca aagaataaaa  35700
gggaaataca tggatatttg cttcaaaata cccagaggta ttgctcaaaa cttgattaaa  35760
aataaaataa cagaattggg gatggacgtc aataagaaag aataagctta aataatatca  35820
gtatctatta aacaacatga tttttaattg tgtcttctct attctttccc tttatcatat  35880
atttacacat aataggaaat gccttttagg aaagatagtg gaagccttct cttttgtttt  35940
taacagccat tgcttatgta gtgctaatgc atcttcttaa atccacgtgc tttaaaaaaa  36000
ataatatttt atggtagtca tgtacttctc aacacatcat ttggaaagaa agttaggggt  36060
atgcgctgta atttgtaccc agtattcaga gtttacaaga aagattgctc ttccctgcag  36120
cctctccacc cttcccccctc cttctctctc tcccccactt gcttcttgct ccttgtttct  36180
ttctctgaag aaggacgtga gctacatgga ggacagggca gaaaagggaa gaaaaaaata  36240
ggaaatggtg agaaaaatat taaggacatt taaaacttaa agttttatgg ttctttttag  36300
ctaaatgaat cttttgagct tccatggggg aaattagtgt aattaaaatt ttctagttca  36360
taaaaccaaa tctttacata ctgactgagc ccactgtaag tattgactaa ggcaaggaca  36420
aatgttatcc tctgacttgg aaaattcaaa agaagcattt tgtctcttaa atgaaggtag  36480
gttgattata tttgatgagc ttcttggaaa aggcattgat tagtccacat ccagaaattt  36540
aacttccctt ttgcttatac tacttgaaaa atgattttat ggacaccgtg atgtaaacaa  36600
tgagtctctc taggaaggga tactgtgtat attttttgtt ttattttttaa ctttctggca  36660
ttccaagaca catacagttt ttatttgagg gaaatattcg taaaatagaa tacgaaggaa  36720
ctattccaaa gtcaggagtt gagtgaaata tcccaattaa aaaactgaaa ggattgttta  36780
tcagtaagtt gcaggatatg tgtagagctc cacaacatga aaattcagta ttaataattt  36840
tggcttgaaa tattttcagt tctatctcct tataagcttc agaattacta accaccgaaa  36900
ctggtgtaac taagaggacg catagcatga gtctcatagg atctctccaa ctggtgcctt  36960
```

```
gtaattttgt atggtatgca tgtgcacaca tgtcccaaga tgcgtttgtt gaggcttagt  37020
tgaaggcccc atactatgag gtctcaaatg ttagagttca ctgaacagca cctttagttt  37080
caacatgcat tttctaagca ctggaaggta cacattgaag aaaaacagat ataactccac  37140
agttgactag ctgggttgac taggcaagtg acctgatgct tctgagactc aattttctct  37200
tctgtgaggt gaaaataatc tccattgaag gcttttgaaa gttcaatata tgaagcccat  37260
aatatagttc ctgccactga gcagggcctt gataaattgt gctagttatt attaaggcta  37320
gacactattg ggtaattata ttaatagata agttagccct ttctcaaaga gctcacagtc  37380
aagaagggca aactgataaa cctagttgta atttagtgtg acaggtgcta taatctgtct  37440
ggaatgttcc cctagccacc accacctctg tctgccatgc agactcctac ttattcttta  37500
aaactcattg gaagcattaa ttgtagatga acacttgcct tgtgataccc accccccacc  37560
agctccccct tacagacacg tactcaggag ttcagaggca gtagctttga cctttcatct  37620
ctgggtctta gtgctggcac atataatggg tcttaacaaa tatttttcag gtaataccta  37680
ttacctaaac aaagtggaat gtagtacaga aaactgattt tgctagtttc acagaaaact  37740
ttgcatttaa agttgggcct tcaaggataa gcaaagtctt gggaaaaata agaatagata  37800
ttccaggtag agggaccagg gtaagtaaag gcatggagac atgaatgtgt tatgtaagtc  37860
taggagtggg aagcagtttg gtatacctgg accatagaaa gtttgcagga acaggagtag  37920
caggaaatga ggctagagag aagtccacag agccagattg agatgggctg tgaataccac  37980
cctaaggagt ttggctctag tcctgcaagt gttaagaaaa catggaaggg ctgtgagttg  38040
ggagatgaca tcatgttctg ttggaggaag ctaactggca gcagtttgga ggtagggaga  38100
ctaaaagcag ggaggctaat tggaaaggtg ttgcaatatt ttagataaga gatatggggg  38160
ccaggtgcaa tggctcatgc ctgtaatccc agcactttgg gaggccgagg ctggtggatc  38220
acctgaggtc tggagttcaa gaccagcctg gctgatatga tgaaaccctt tctctactaa  38280
aaatacaaaa attagctggg ctaggtggtg ggcgcctgta gtcccagcta ctcgggaagc  38340
cgaggcagga taattgcttg aacccaggag gcagaggttg cagtgagctg agatcgtgcc  38400
gctgtgctcc agcctgggca acagagcgag actccatctc aaaacaagca aaaaaaaaaa  38460
aaagagagag agatacggag atatgggcag gcaaagggga aaggaggtga gtgtggggtt  38520
tggggtggtt ttgcagtata tattttagag atagaaacct attttccgta attgggatta  38580
ttttgactcc taccattgta acatttttcta gacattggtt ttagaggtac ttcttataag  38640
gactgtacca agaaactagt tgaatgatat attcctcaag gtttggggcc tttttggtgc  38700
catgctttgc tttctttagt taggattagt cttggctatt tatccttctg ctttgactat  38760
gagaagaacc acatacctgt aattggtcag acaaaagaac attttatatt ctctatgtct  38820
ctgccttgca ctagaaatgt ttgggtaaaa aatttattgg tttaagaagg aagaaatgtg  38880
cccaaatagc caatgattgg cttgatggct ttggctaggc cgttttgctg ctttgagctt  38940
cagttttctt atctgtaaaa gaaacatatt gagctaaatc ttgatatctt tttcctattt  39000
cttaacgtgg tatggaagtt aacactttcg tccttttact gaatgaaaat aatctaatag  39060
tagcttaaag aaaacggaag catctttcac ttcagtgttt tgagcgtaat gaaatgaatg  39120
ctattattat aaatagcagt accattttac aaaatcagaa gctaggaaaa tgtatttggc  39180
ctttgactcg tggttggtcc tcagtgaatg ttcagtgaat agaattataa aatctctttg  39240
ttcttttttg ctgagtacta aagaccataa atttattaca gatgatattt actgataata  39300
aagtactttt atttttactg gtacccaaag aaggattcaa aaatcttggc agataccata  39360
```

```
ttaccaaatc taactatagg agctggacca agagagaaga ctctgtaaat cacctgtcta  39420
cagacccaag acccaaccat cttaaaagag gattcaggaa atcatttaaa tgtttcttcc  39480
tgctttcatg ccttgaacat gctgtttctg agcaatacac tacagagatt gccctaattg  39540
acactaaata tgagttttaa gcatttattc tgaaaactag acccatgtaa acaagttagc  39600
atccaactat caattcttag aaaatctact ttccctatat gtctactgga ttatttgtct  39660
cagatcttag gggaggaagt ggaagagctg gagaacagca cgtgttattt tagagttata  39720
actggaagta tttggaatgg cttctatgaa agtttatttc actgaaaatg tggaaacagc  39780
tttggaacta aggaatgggc agagactaga tttggaggag cagggtacta aaagcctaga  39840
gtctggcgag gacttagaag agaaaaagat tctggaaagt ttggagctct taaagaaaaa  39900
taaaaattta cttcacttct aactatttgg ttggtgcaaa aataattgca ggttttgcca  39960
ttactttttc accaactaac aaattcagtt tcaaagattt ctatactgct gacagttttt  40020
ttcaaatatt agccctttta attatttcat taccagacca atataacctt aatttttttc  40080
aaccaagata aacaattttt ctgcagtaaa tttgtattta tgttccagac acatctcatc  40140
tgatatacaa tattttctta aattgtataa agagaaatta ttgtacatcg gatgagctgt  40200
gtctgggatt aagtattagc tccactgtaa ccttcatttt cttgaacact ggaaagaaag  40260
gccaacggtc atttagtagg gttggaatag gatggggaat ggggctttgg tgagagagca  40320
ttggactgtt ggttatagaa acacagttca agtatatctg gagttcagat ttgagatctg  40380
actaggagaa tctgtctagt gaaaaaagct agacctttac aaattgtagt caggagctac  40440
cgttgtaaca gtctgccaga gttcctgata caaaagattg ataatttgtg tgtttgaaaa  40500
acaaaacaaa acaaaacaca tctaccttca atttgactta ctgcaactct gattttcatg  40560
gcaagggata gagacaaaat tcattctata aaatttgaaa aaaaatgtat atcctgaaac  40620
cattggaaat tggatatcag cattaatttt attggactga aaaacctcca gtttactaac  40680
aggagttgaa agtcatcact tttcctttca tcatagtgag ttttcatcac aaaccacaat  40740
gatatgctta tctcaaatat attcatttac ttgttttaca caagtatcat ttctgtttac  40800
ataacacgca attttgttgc tgctgctgtt gttttattat gcctgtcact tgagtaaaag  40860
atggataagg taaggtctcc atttagaaat gtatagtctc ttggcaggga agacaaataa  40920
aggcccataa ttatcataac agaaaaatta atatgtgacg caagaaaaaa taaagatact  40980
attaaatttc tttgggactt tgaaggagga agggagcata tagacactta gtaaatattg  41040
tttgaagaag ggaatgaata tgtaaaggga gaataaacct cacctataag gtctagggca  41100
atttaaacac aaaggagttg tgtaggatta tttaaggttt gcaaatgtgt aaaattatct  41160
cactacaata ctagggaaat ggaaaaacac caaagttcct ctaccagctt ttgctggatg  41220
agatgggcca gaagtagtaa ctgcgagggc agcctgtatt tctgttgttg gtgtggttta  41280
tcttcccagt gccaatgctg ccaacttccc ctcaaataaa aacccatagg ggttcagagt  41340
ctcatgaggt gagaacagac ttgcactatc tgtgacaaca acaaaagcac ttataatttt  41400
gatgtggagg atcctaattg aaatctgctg tttgaggttc cttgggtcct gcattctttc  41460
ttaaatattt ctacttgagt tggttattga tccttattta ttttccgtct aatcgattga  41520
ctttataaat ctattgcaga gggcagatta aataggcaga cagttttcta atttgctgtg  41580
agggtatttc ttaatttact ttttaaatac tgattttatt tatacattta tatgcacagg  41640
tcattttcat ttccatgata tcattcgagc ttcacaacca cactccaagt tcagtgttgt  41700
tatcttcatc ttcatgttga ggatgaggac acggaagctc acaggtaaag tgacaaaccc  41760
```

```
cagtctttag gctactagat ggtggagttc agactctgat tttctggcca ggtgctcatt  41820
tgatgatagc agcatgaagc tcttcccatt ctgcaccgtt tgagctccta cccttcctaa  41880
tcttctttct ctaatacgag aacactgtaa ttaaagtggt atttggctga taagtagtag  41940
gttttgattt ataacacata gagctggcag tgtaattttt gtcccagaac ttgatgtgcc  42000
atgaaagcta ttatgctctt tttttttttt tttttttttt ttttttgag acggagtctc  42060
actctgtcac ccaggctgga gggcggtggc gtgatatctc ggctcactgc aacctccgcc  42120
tccagggttc aagtgattct cctgccccaa cctcctgagt agctgggatt ataggcatgc  42180
accaccactc ccgcctaatt tttgtatttg tagtagagac agggtttcac catgttggtc  42240
aggctggtct tgaacgcctg acctcatcat ccacctgcct tggcctccca aagtgctagg  42300
attacaggca tgatccacca cgcccagcac tataatgctt ttaatagagg gaaatgaatc  42360
ttcagatgat gtcagcatcc taattttttt tctcctcttg gggtttttct aaatgactgg  42420
caaatggaaa acctgaaagt tacctgagac ttctctgcat cgggcttgtt ggggtatact  42480
gttcttctta taatcaaccc cagggactga cagatggaca gttgttagag acaaagtcct  42540
caatccaagg aggtcactca gggccaactt tccttagtat atatcgttca ttacattagt  42600
tggttatatt acctgtagta caactcaagt acaatagctg caggaggaga cagctcgcca  42660
gctaaaccta aaagttacaa cagtgacata gcaagcaagg gtaaaataaa aggctcttga  42720
cttattcctt catttttaa taaagcatga agtttgacat aaattttaac ctctggccgc  42780
atagtcagtt atgcttatta tcttgtgtgt attattatgc tgtcaggagt tggccactga  42840
tgaccaactc caaaatttag atgatagaga taaaactggt agttaatata tgttgagtac  42900
caggtcaaaa actccataag acactttaca ctgtgggaac tggttcatgt aacagttctc  42960
caggatggag gattaatatt cccatttcac agatgcagag ttatgtgtct ttctagacct  43020
gacaacacct gtcacctacc aaatgaatag agagctatgc tataagtcta gggatgagtg  43080
atccttggat gcagagcact tcctactagt attctgactt ttactattat gcgtctgtta  43140
ctatttgaca gctctcattt ttgcctgtcc aaatttaagc acgtttaatg agataaagag  43200
agcagaggca aaggtgagac tggatcttcc cttgtatctt attgatagag agtaaatcga  43260
atccaatttg ctaaggcctt ctctctcctt tcatgtttcc tcactttgcc tccaccacca  43320
tgaggttgaa aaatgagttt ccatttagtt taagcctttt gttattcatt acttaatttt  43380
gcttctattt ccctcttcta tctatgacaa attcagcaca gtgaggggaa gaaacagtga  43440
tgatagtgat ggcctcaaga agaaaacagg gtgactgagt aggagcaaat aagtatctca  43500
gaccagcata taaacaagtt catttgtagt gtaaaagaac attatgcctt tggcttgaaa  43560
actgcctttc caatttatga gcatgtttag gattatgtaa gtacagtgtc ttcataacaa  43620
gcccaacacc tcttacccaa agaatgcaaa acgctttgca aacagtagaa ctcacaattc  43680
ccctgtgacc tggggactta tatgtatttt catgcattat tttttataga ttgagaagtg  43740
aacttgagac ctaccaatct gtccacgttg acaaaataga tccaatacta aactcttaat  43800
tccagcttcc tgtcttctta gaagcagatc acactgaaag aggaatctta tgtcaagggt  43860
agcaattttc tctctctctt tttttttttt ttaaagaaaa cacaaattac atagtagata  43920
tatttgcata aaggtagatc ttgaaaacat ttaattaaga cagcggtatc tatttccagg  43980
aaaaaataga aaagccagat ctctactcca ctgaatttaa aaattagagc agcattttgc  44040
agttaaaaac gattattatt ttgcattctg ccatttgtct ttacatgaag aatgcctgaa  44100
ttcagaatgg aaaatatttt cttttgaaaa gtgcatagga aagaattgtt ataaagcaaa  44160
```

```
tgtgttcaga atgtatgtag atattaatta taagtaaaag taaaagaagt aggatgtatg  44220
tgagcgtatg tgcatttgtg ttgcagataa accgattttg aaggttgaga gacatgacga  44280
tacttgttag gtatgaggga gacaagacca gaggcgccgg gaagcttgac taccgtggag  44340
agctcagttg agacttgtct ttgcccatgg cctgcagcgc ttatgtagaa attggggatg  44400
cttttactcg ttccaaagcc taacctgatc agacctgccc aggttggagt ttgggaaaaa  44460
aagtgtttga agtaaacagg aaaattactc accttaatga tgtgtcttac tggcactgac  44520
agtgctttga tagtctgaca gtcttttttt ttaagttttg ggaggaaaga caggggaaat  44580
tattaatatg atttttggaa aacatagatt cttatgctta tgcacttgct aataaggtgg  44640
aaaaagtggg ctttgcacca tttacagtta tggactcgcg tttcctccta ataaagtcta  44700
tatcaggaat tttccattag gaatttctac caaaaagaaa agaaaatacg ttactgttta  44760
ttttgtgtac ttgtgccatg tatctccaca attgcgctgt ggctgttcac acagaacaga  44820
ttcttcctag cacttgggct gtgggttccc aaacttgcag gtcgctttca tctgtctggt  44880
gattaagacc ataaaccaag tggtgtgatg agagagtttg gtgctctaga cagagcaagc  44940
acacccttt ttcataagaa gcacaattct taaatctctg cacctaaatc tttccttagg  45000
atgggtcagt tttttggaaa aagcaattat atatgttttg atattttgtt gaaacataat  45060
agatgttgat ttcatatggt tttttccctt tttttttttt tgtctttgct aaatgtcaaa  45120
cggtacattt tttctaagct tgaagacaga gaactgggtc atatgtctct aaacatttaa  45180
atcttcactg agatagggaa gagtgacctg atcttatgga tcgtccgagt cctgtgagac  45240
aaaaatgctg ggtttttcat gcagtcccta attcactttg accttggtgg agggagtcaa  45300
atctcctagt ttgagatccc acacatataa agctctagag tttcaggatt aaaatcttct  45360
taactttata ttctcagatt ctgtatagct tattaaacta gatggagggt ctagttatac  45420
tgtctagaag gacatagatg aatagttata ttttataaaa attaaactcc taatgataaa  45480
aggctaaatg gggagagaat aaattatagt ttatgaaggc atgtaaaaca aaagatgtct  45540
gccaatttcc tctctttggt tctctgactg ggaataactg tatcgttttt actttttttg  45600
tcctaactgt gtcctaattg taaatgaatc tggtgcccag taaaatcaaa tgaatagaaa  45660
tacttaccat ggtgtgtata taccagcctc ctggtgtctc agatataatt aacataatga  45720
aagcattgca atacattctt accgaaggct cagttcctgt cctgtcagca actgtttgcc  45780
tacaactaaa gcaagtctgg gttcaaagca ttttaaaatg ttccaaaaaa gtggggaagg  45840
cggctgggtg cagtggctca cacctgtaat cccagcactt tgggagaccg aggcaggtgg  45900
tcaggagttc gagaacagcc tggccaacat agtgaaaccc catctctact aaaaatacaa  45960
aaaattaact ggccatggtg gcaggtgcct gtaatcccag ctacttagga ggctgaggta  46020
ggagaatcac ttgaactcag gaggcagagg ttgcagtgag ccaagatcgt gccattgcac  46080
tccagcctgg gccacagtgc gagactccat ctcaaaataa taataataat aataataata  46140
ataataataa taataataat aataataatg taaagtgggg aaggcaagat ttggctcacg  46200
cgtcagactt cctatcaatg ggtctatctt tgaagcaagt gctcagagtg tctattcctt  46260
tgatcacacg ggtagtggtt tatttccatg agtatttgct gttttcagga gatttcactt  46320
tgggttttgt ccatattcca cattcaggaa actgttaatt ttggaagaag agattgtttt  46380
tacttggttc ttctaaggaa attaatcaaa tgtacacgtg caacttaaaa tcaaagaatc  46440
cctgttttaa gaggagtttt tcttatttca actggcaaac aatatgaaac tgaatgtacc  46500
caaagtgttg gaggtttaca aacatgatca gcacttgtta atgacaattt tctcctaaga  46560
```

```
aaatggaatg ctaccttcta gcatggggac ttgtaggcag tatttctgtg tttgctagcc  46620
ttggaaagta taactcttat agggttgggc aaagcaaagc gtttttgctt tgtaacctgt  46680
agaaatgatt acgtagtgta atttggttat ttaatataat ttgttaataa ttctcattca  46740
tctaccagaa acttaaaact tggtactatc ctgctaattt ggttttggta atgtctcttt  46800
tccctaattt taatatccct gttccttggc aaacccatcc atacacctac ctgttgttca  46860
actggtgtga taagccccat cagtgctcct agacattttc ttttcctact cttcctcttc  46920
agtgtcaggc agaaggatct ttctaacact cgcctcagtt catggattgc tgatggtcca  46980
ttgttggtga ctgcatgatg acctgtaagc atgtcacact ctgaccaaag tgtttgtatt  47040
tggcccaatt ccccacggct aataataatc cctttctgtt tggaaaatgt cttatatttt  47100
tcaaaacaca cacatatatg tattatcaca tttaatcctc ataacaaacc tgtcacattg  47160
gcaggtgtta ttctcacttc tcacatgcaa agttatgtaa cctttcttga gattatacct  47220
cagtttggaa agtaggggaa tgagccttct gcctctgtga gtaccgtgtt cttcacggtg  47280
tacgatgctt ccaaatatat actcttccca acaggcagag gtggtgtttc gcagtcaaca  47340
aaagatgatt tttgttttgt tttcccttct gcatgccctg tctcctgcta cttcctctgt  47400
tcaaaacatt tttttttct ctctctctct ctcctctcac tgctgcctac caaaattatg  47460
tcacataatt tggctattta atgtaatttg gttaataatc ctcatctatc taccagaaac  47520
ttaagagttg ttatcatcct ggcaatctac cttgaagatt ggcaaaatgt tagttaacta  47580
ttgaatatag atgatgagca tatggaatta aatttgaaat ttccaatttc aggttccaaa  47640
aatccaattt caaattaaga aattttaaat ttaaatctta aattaagaaa tttaagaaac  47700
ttcttaaaat ttttacttat cctttctagc tagagttgcc agatttagca aataaaaacc  47760
aaggatgtca gttaaatgtg aatttcaaat aaaccatgaa aaaatgttta gcataaggga  47820
atcccatgca atagttatta cttttgtttt attttgtttt gttttcttga gacagagtct  47880
ccttctgtca cccaggctga agtgcagtgg tgcaatcatg gctcactgtg gccactacct  47940
ctcaggctca atcagtcctc ccacttcagc ttcctgatgg ctaatttatg tattttttt  48000
ttctttaggg acaggggttt tgccatgttt cccaggctgg tctggaactc ctgggcttaa  48060
gcaatcctcc cgtcttggcc tcccaaagtg ctgggactac atgcatgagc cattgtgcct  48120
ggccaatatt ccttacttat gctgaaaaat ttcattgctt ttacaattaa attttaatta  48180
ggctggagat tatctggtaa ccccattccc agctcaatca ccaactctct aagcagaagg  48240
aaatttttca tctctcttgc catagtgagg tcaggattag tgaggtgaca agattaaata  48300
tgagctaagc tatgacactt gttttccaca gtttcctgag ccccccctccc tccttttctc  48360
tttcttcctt cttacctccc ttcctctctc ctatttattc ttcctacctt tttgttgttg  48420
ctgtgagtgt cttcacctgt ttccttcctt cctttatatt cctggtaatg tttcaaattt  48480
attggcatgg gcagcttctc ataataggtt tgtttttatt atttttcttg ttattactaa  48540
aacatgttaa tagatagatt ctaactctat ggcacaacta agacagttgt gttacattct  48600
tttccgtgtt ggggctaatt agaatattaa gtttacaaag aatgcagaaa aagcgaacaa  48660
gatgaagcac gtttccgtct taaacaaatg aactctaaag aaataggaag taacatgatg  48720
acaagctttt aagagatgtt gcaagtagag gaaagggttt gtttaaatct ctccccaagc  48780
accccctaca cctaccccca gccaacacag atgcttatgt attagtggcc cacacggtac  48840
ctaattatca acgatggaaa tagatgtctc aaaattgttt caattatcca ggggttccct  48900
taaaaaagga gaggagagca aaagtttaaa acttggcttg aaggtattaa agagcaaatc  48960
```

```
tgatctaatt gattaagtta cacctttcct ttttggcagt atcttaatac ccctaggatc  49020
tcagtatttc agcatattgg tttcctgtac ttatctagaa taaagaaact cagcaatttg  49080
cctataggat agtagagcct tgaactaaat ttatctcatt attgttcact tgaaaccttg  49140
gggacagctg tagttgaagg gaccttaaag tcccttaaac ttctcagcat ttgcaggttc  49200
acttttaagg tgcactaaaa agcaactagt atcctaagct aaaaaaaaaa aaaaaaaaaa  49260
aaaagaaaaa gaaaaagtag atttaagtat accaatgagc atggactctg tttatgtttt  49320
gaaatccatt tgctactcat tttcctcgtt tttaaatcct attatattta cacctgggca  49380
tccatttctc tgaagagaga agaatgaagg atctaaaatg tcagaataac agtgattctc  49440
aacaattatt gtcggcactc tttcatgaag agatttaaag ctctttgctt atctgactta  49500
attcctgccg gaaggacagt acagagggat tacggtttaa atattgcagt tagaagcaca  49560
aagtggaacc tggacttccc cgaccttgga agaaaaatag taaagtgtgg ttcctataaa  49620
atattatagg aacttcagac atagaatgga gcatccattt atagtgattt aagttccagt  49680
attgaaacag gccttctatt tttatttcaa tctccctccc ctttattttc tttgttttgt  49740
gattcacccc aaaacgtatc ttcttatacg gtaatattaa ctagtacctt agtcaaagat  49800
tgatctccag aagtttgttt aggaaattcc ttgtgttact tgtctagcag ttaaactgcc  49860
tagtggaaac aacagctcag ctaaatagtg tgatgcaatc gtgatagctg ctgttcatca  49920
ggcatttacc ctggaccaag cactgtaccc tgaatatcat gtggcttttt ctccacactc  49980
aggacaagct tgcagtgggc agtagtatta tctcagcctt gaaatgagtc acacaaggtt  50040
ttgcagcaga gagaactgtc ctctttttca gccctgtaca ggggaggagc aagggtgctg  50100
cagtgagggg atctggagtt gaatctggct tagtagctgt gaaagattgg gcaacttatt  50160
tcacgtttag gagtttcaat ttacttaact ggcaaatgga ataacaatgt ctacttcaca  50220
gcttactgcg atgatcatat aagacataaa gaacttagcg aagtgcctag actgtagatc  50280
acagtacgtg ttagcttttt gtgttttata catcaagcgt aagtcttatt ttttacatct  50340
gtcatattac cctttcccca gtattcagag tatttgagtg tatacgtacg ggtggtaagt  50400
gttgtttttc attgaaagtg cagatcctaa cttttttttt catgcagtaa tcctcaaaaa  50460
ggtagacgtc taccataatt cagtctattg ctccaattgg aggatgtaca gttgttttag  50520
gagttaagga attgagtttt ttcttttttg cttttcgtct tttttttttt tttttttttt  50580
tttttttaca aattctttta ttctttttctt ctccaaattc aggcaaacag tattaaacac  50640
tttgttttaa aaatagattg tgtacgtgtg tgtgtgtgtt tatgagagag acagagagag  50700
agatgggaga gggtgagaat acacagtaag gacttggaac atattctttg tgtgaaatgt  50760
taaaaaattg ttcacggtgg ctgggtgcgg tggctcacgc ctataattcc agcactttgg  50820
gaggctgagg tgggtggatc acgaggtcag aagttcaaga ccagcctggc taagatggtg  50880
aaacccgtgt ctactaaaaa tacaaaaatt agccgggtgt agtggcaggc acctgtaatc  50940
ccagctactc gggagcctga ggcagagaat tgcttgaacc cgggaggcag aggttgcagt  51000
gagccgagat catgccactg cactccagcc tgggcgacag agcaagactc agtctccaaa  51060
aaaaaaaaaa aaaaaaaaca actattcaag gtttcccaat aaccttcttg ggctttgaag  51120
ctagagagcg ctttggaatt catgctccat tatatgtgtg tcttaatgct atatactgtt  51180
gtaggtcagc aatatttata tacataagtt tatatatatg tatatataga tcttttgtaa  51240
atagagggtg gatactttgt ccccaccttt tcccatccta gcatgcagta taatgatttg  51300
aacacggcaa ggacaccaca aaggcacagg aagacatcct gcaatgtaca tatagtatgt  51360
```

```
gccttatgta cagtaagggc cctgaattta aagttaaaac ctagattgga gaattctaac  51420
tttgtgttat cgtgagcaaa gtagtttact taagtctctg attctgattc ttccttgaca  51480
gaaagggaat acaggtgact ttcttataga gttagctgag gattaaatta atagctgtat  51540
gaaaatgctc tataaactgt taaggactat acagatgggt gagtgatggt gtcatttatg  51600
gaaatcagta gatgccatta ctctccatac tgtcgataca tagtctccca tttcttctta  51660
tcagactggc ctacctagtc ttccggtaaa aagaatatcc cgcagataca aattaccatt  51720
actggaacag aggactcact tttagagcag atgtacaaat gaaactccaa aacaagccac  51780
aaatctacca ggaaagagaa ccaatatgtg tggtattata tcgccaagga tacctgagtc  51840
atttcataga aattgagctg tgagtgcctc ccagaatgaa tggtttctga acgtgtttct  51900
gttaggaatg atgcaacctt cagtagagac cagagattta agaattctat actgtgagtc  51960
attttaaaag acaatcaaag agtatgtgtg gaagcataga caataacttt cacctctagc  52020
gtccaggtgt tgaaggaggt cagctaccag ggaaggactc ctacgacttt gggtgccact  52080
gcgtgaggct ttgtcttgga ccagggggta aaacatatct caggcaggac gctgagctct  52140
aggtagggct atcgtttttg tagaagcgtg acttcttgat acaacaaagt aagagctgag  52200
gaaggaacag ggaaaaccag tttgggccca gaggggaaag aaatgatagt gtagtagccc  52260
gcggttttgc aggcagttgg gagtagcaag ccacccttag ggggaggata atgttttctc  52320
taccttaagg gaaaatgata gctgacttgc agagcagtgt gctgagacag acatgctgct  52380
actgcagtgg aagggggttg caacgtattg tcttctgtct ggagagagag agagagagag  52440
cgcgtgtatg tcacgtctgt gtccataaag ctctccgatc tgcccaccaa ccctgtcccc  52500
caccaataac atcttaaaga gaagaggtac aggaatgttt tacagtgaaa agattacagg  52560
gctggaaatt agaagccaca agttctaatt atgtctcatt gctaacttct ggtgtgatat  52620
tttctctggg tctctcattt atcggggagt taaactaggt atgtccagta ggggtgaggg  52680
gtaagagttc tctgcccatc cagggtttct actagaagaa ttttgactct acagataatt  52740
gtgtcttcct gtattgctga ggaatgtcca ggtttgtttt attgaggggc aggggagcac  52800
atagatgtcc agtagtcagg aaggtggttt gcaggccttt aatcagcact gagaagaggg  52860
aaaactaact gcagttcagt tctcagttcc accattcact ggagtgctgc tttcaacttt  52920
tgagctcctg tttctacacc tctaacgtat cagtgtcatc tcaccctggc ctttttctca  52980
tgatggtcgt gactttagga aacatgtaag agtaagccga ccttaacacg agtacctgct  53040
gtatgacagt cactctgaca aatgcctccc agtgtctgct ctgtgaaggt aactgtgaat  53100
gatattactg gtcaggtggg gttgacagag gtggccctgg caggagacac taaatgaaag  53160
gtcattttac cctcctgggg agataaagtt gcaaaattac cgatcaagtc tgtcaaatct  53220
ttttagactg ggtttccaaa tccataccct caggcaacta gaacaaggct ggcgagctcc  53280
acccccgccc cttcccaagg tgggtgccaa catgctgccc ttcagcaggg aggacacagc  53340
tgcctctggg gccagtgccc agggctagcc acaaagctgg ctatggcctc cccaagaaga  53400
cccaggacac attactccct gcagaggttt tgctgctttg tggcacggtc taagtgtcgc  53460
cccactccca ccacctgcca ggcccagtgg gctcctggct ggtcctcacg gtaagtgagt  53520
agcagacagc ccacctgctt gatgtcaaca tttgtgggcg cggcccggga agaatgtgcc  53580
gctcccagcc tccttggctc aggtaattaa tccccgcaac tgacaggtgg caacaggcgg  53640
ccctttggct ggagccatca ggaaaagtgc ttggaggaag gattttttta aaaaaatgat  53700
caagagcaca attcgtacat gtctggcagc tagacggctg tggcaggaag ggaggcaggg  53760
```

agaagtaaat accttgccaa gacgactgtg gggccaatgt tgggatctgc gtctgcctga 53820
tcattgtgat agatccaaaa ggatatggtg gccttggact tgtttgcaag ctcactttgc 53880
agaattcccc ttcctttgat gtggatacag tcttaaaatg gaatgcctca tttgtgaatc 53940
aaaaaatccg gggccaaagt tggagcccca gaggagaaat aatttgccca agatgatgca 54000
gtaagtcagt gggcaggtag aggactagaa gccaaactca atgcctcttg gctttgtttc 54060
catgattcac tgggcaatat ttactgcccc attatacaca tgtagtttag aaatagaatg 54120
acaaaactgg ggtcctagtc aaaggaagga tgatcagttg cctcttgaaa gatattagtg 54180
ttttcaatct aaccacttaa agctgacttc tcaagagaat gcccccaccc caaccccaga 54240
ccacctgtac ccattcaccc cccctacttt ttatttttgg tagttcggga cactgactat 54300
cagaacacat tgacctgatg tttattagga tggatatatt aaaagccatt gaaatgaaca 54360
cttttccttt ttcttttttt tttttctttg agacagagtc tcgccttgtc tcccaggctg 54420
gagtgcaatg gcatgatctc agctcactgc aacctccacc tcctgggttc aagtggttct 54480
cctttctcag cctcccaagt aggtgggatt acaggcacgc gccaccacgc ccagctaatt 54540
tttggcacga cctcagctca ctgcaacctc cgccttctgg attcaagcga ttctcctttc 54600
tcagcctccc aagtaggtgg gattacagac atgtgacacc acacccagct aatttttgta 54660
tttttagtag agatggggtt tcactatgtt gtccaggctg gtctcaaact cctgacctga 54720
ggtgatctga ctcggcctcc tgaaatgctg ggattacggg ggtgaaccac tgcacccggc 54780
caacactttt taaacattac atttttaaa aaataatatc tttctcgata tgaaatttaa 54840
aatgtttttc aagtgagttt ttttgtagag gacaaatcca aagtatagta tataattagc 54900
ccatataact tcatgtgata atcagtgtct ttgaagcaga ccaaactgaa gctgtgtctc 54960
agcgctaagg gtctttttac attttactga attggatctt tagaattaat ttttcaaacc 55020
ctccttatca aaagttattg ttggaccctc aaatttttat tttcatgtat ctcatttctc 55080
ttccctaaat cttgcctccc accagattag ctgccagaac tttatctggt tctctggcaa 55140
ccctccatct gttttgtatg atttttcatt cccagcagtt ctaattattg atttcatcac 55200
cctcttaccc ttataaaagg acatttttaa tttggcagtc ccaaggaata tagcttataa 55260
aaagaaaaaa aattaagtca ctgaatgttt taggagagca ctaagttaag acagactttg 55320
tacttgatta acggaattgt tctgagagct ttagagcttg acttttttttt cttcctgtca 55380
agtattttgg gttatttgag atagtacaga caacacttta cctcttaagt tttttgaact 55440
agaagccata aattagaagt gcacctggca tttcctgttt gtgactagtg gctatctttt 55500
agataacagt gaagtcctca atgtccttga taggttcttg gtaaactgcg accttaaaca 55560
aaatgatgtg caggagatct tcgagtaatt gtttcataca atgttatttt cttataacag 55620
tgatgagaaa aacaaattgt tttgttatat gtgttttgct taaagttaca gttcccaaaa 55680
atctatcaaa aatgttaaat gaggattcat tgtatttgta aatctcatta tttttctctc 55740
ttttttaaag aaactaaatt caaattcatt cagaaagcca ggcataaagt gagactaata 55800
tgttcgttgg tgtatttaag cctttcttag agttttcttt tttttaagac ctcagtataa 55860
gaacatgcca gacgtgaatt gatctggaat tgcagactcg ggagggcttt gatgctactc 55920
tatctagttg ccttccttga agagggattg agaagagagg taggttatag aattaatgat 55980
tttttttgt tccgtgagag tttatttcat ccatagtctc taagatttag ggctcaagat 56040
agccatgtga tttgagattt gcatgtagta tggcatttct tctgggagag gatgaaagag 56100
ctaaagttct tgttttttgg ttttggtgta gtaggcaggg agggttttga ttctaccttt 56160

```
aggaaaggga ggtgttgaaa aattacgcag gtgtgtgctg atattacctg gcacctctat  56220
gcattgtgat actgaattac cagtctgcca gccaaaagcg tgtaatatag tatgtctact  56280
gaggcaggtg gtaaaggtag ggtcctagtc actggaattc ttttttttc cccttctct  56340
ttgcaacata ttattagtaa aggagctgaa tttacttgtt ttccaaaatc ccctggagtt  56400
gttttatttg aacatgatat ttggctttaa gcagctcacc cctcgatatt ccaaacttcc  56460
tcccctccct cccaaagcaa aacaaaattt aggcaaagct tacttatcca ttttgacaag  56520
gatattttat aaaaagaagg agtttagttc atttgttagt tttcaggaac ttcttttcca  56580
tgtcattgtt gaaatattta gttcatgtgg atggccaaaa ctgtcatgtc agtatacaag  56640
gaaatttggt tgaagatcag tacaatatta ggctcatcat tcttgcccat gggctggtgc  56700
ttcctgggaa tgaacaaact attgaatata tgtacagtat gtatacagaa gaacatatat  56760
taagttctac tttatatatt tatacatata tgatcagaaa tggccagtag ggtgtgtgtg  56820
tgtgtgtgtg tgtgtgtgtg tgtgtcatca gaaagattac caacactttg ttttccacat  56880
tctttttttt tttttttttt ttttttgaga cagtctcact ctattgccca ggctgtagtg  56940
caatggtgtg atcttgactc actgcaacct ctgcctcctg ggttcaagca attctcctgc  57000
ctcagacttc tgagtagcag agattacagg tgtgcatcac cacacctaat ttttatattt  57060
ttagtagaga tggggtttca ccatgttgtc caggctggtc tcgaactgct gaccttgtga  57120
tccacccacc tcggcctccc aaaatgctgg gattacaggc atgagccacc acgcttggcc  57180
ttccacattc tttattaaag agtcactttg ccagtgcaaa tctggtaact gcgttctcta  57240
agagatttgc accaaattat aaaataatca aatgaggccg gacacagtgt ctcacgccta  57300
taatcccagc acttctggag attgaggcgg gcggatcacc tgaggtcagg agtttgagac  57360
cagcctggtc aacatggtga aaccccgtct ttacccaaaa tacaaaaatt agctaggtgt  57420
ggtggcgggc gcctgtaatc ccagctactc aggaggctga ggcaggagag tcgctagaac  57480
cttggaggca gaggttgcag tgagctgaga ttgcaccatt gcactccagc ctgggtgaca  57540
gagcgaagct cagtcttaga ataacaaaaa taatcatcat catcatcatc attatcatca  57600
aatggaagta acactataca ttatctattt tcccctctat gaatgattag ctcaagattt  57660
ggggggatca tgtaagttgc cagttatttc tcagtgagtg tcagatattt atgacttctt  57720
tgaagaggcc aatcgttttt gaaaattatt tcagatgtgc tttatttccc cccacccatc  57780
acagtatttt atttctgatt tcacttagat ttgcataatg caaagagcca cagttgcact  57840
gggggtcctt tctaaatagg caacgaggtt agtgcaaccc actgctgact tattgaaccc  57900
aggacctgat ggagtagagt tgattcttaa agcaatgagt gggcattttg tgttgttttt  57960
atgttcaagc tcccattgtg agaatatggt tacactttag ggaagaaaac ctcaactctt  58020
agacaaactt ctttgcttaa ctaaaaataa gtatatatac tcctgtaaga atttggtgat  58080
catattttta tttttgttag taagatggcc tctgagcttt acacttgatt gtctaatcat  58140
atattttcta atcatgtgtt tattcactca aattcactct ggcacgaata caccagttcc  58200
actttggcct catactataa ctgttaaaac tgtgtgggac gtggggaaga acactggtct  58260
gtatgtcaag atggtcccag ttactgagaa cttttgagca aatctcttct cctttctggg  58320
gcttagattc ctcatcggcg aataaagtgg ctgaaccaaa tgatctttaa ctttgaattt  58380
tcctgatcta acttttcctt ttccttttcc tccctctgcc tcctcctcct cctcctcctt  58440
ctctctctct ctctctctct ctctctctct gttgcctagg ctggagtgca ctggtctgag  58500
gatggctcac tgtaacctca acctgctgca ctcaagtgat cctctgcacc tcagcctcct  58560
```

```
acagatgccc ccatacctgg cttttttttt tttaattttg tataggcaga gtcttcttgt  58620
attgcccaga ctggtctcaa attcttgggt tcaagcaata ctcctgccta gacctcccaa  58680
aatgctggga tgacaggcat gagccactga acttggcccc tgatctaatg ttctaaaaaa  58740
atcttagcaa atgtgtgtta aactaaaaat gctttgaaat gggatgactc agtaatagaa  58800
acatagaacc aagcccttgc tttaagatgt caagttggat ttctacagaa attctgtaat  58860
tagaatataa tattgtagta aaagcattat cttcatagaa ctaaggaaat ctgagttcac  58920
ttcttcatta cccaaattta gttgtgcaac ctttagaaat cattttatca gggatgcact  58980
cctgaccctc tgtgatatca tgaaatacgt atttggactt tgtccaagtt tcttggcata  59040
taactcctaa aatccttgga atttccaaaa tgctgccttt tttgtatgct aatgctggct  59100
catgggttca gaatgggggt ctggtcactg gaaaggcaaa ggcacaatta gagagtcagc  59160
cccacccccc agcctccagg aaggagagag aggctgaagg ttaagttgat caccacttgc  59220
caatggttta atcaatcatg gctagataat gaaaccttca taaaaaccca aaaggacagg  59280
tttcagcaag gttcaagata gtaaaacatg tggagagttt tagaggttga agcccaggga  59340
gggcatggaa actctgcacc tctcccccca taccactccc tagatgtctc ttcatcttca  59400
tcctctgcaa catcctttat aataaaccag taaatgtgtt tccttgaatt ctgtaagctg  59460
ctccagcaaa ttaatcaaac ccaaattggg gtcatggaaa acccaatttg aagctggttg  59520
gtcagaagtt ccagaggtct ggatttgctc ctggttgtgt gtggagtctt gggaactgag  59580
tcttcaacct gtgcgatatg acagatctcc gggtagacag tgtcacagtt gaattggagg  59640
acacccagct tggtgtctgc tgcttggtga gtggtgaaaa actcccacac atttggccac  59700
agaagtcatc ttctgtgttg atgattgttg ctgtggtaat gtgagaggag aggaaaaaac  59760
acagtttgag catttcccaa aacatcctcc aagctaaata gacccccatg ttttaccttc  59820
tctccttttg cttttttttc aagacatgtg tcacaatttt agaaattatt tttttaatg  59880
tcagtacttc ctttggatca actcccttag tgtaaggttt accgttggtt ccctaatagc  59940
caggacaagg actggcatga agcgcgtgct caataaatat ttgctgaatt aataagcttc  60000
acctctttaa gtctcagttt tatatcagaa aattaggaga agaaggtttg gacaagaggt  60060
gctataatgt tccttctgag ttctaacatc ttctgtattc tctgtcttct aaaatcatag  60120
gtctgtaaca agtttacagg ttggtgctac tcataataat ttatgtatta aacattttaa  60180
gtgagaaata tttcaaggtc aggtgtggtg gctcatgccc tataatccga gtactttgac  60240
aggctgaggt gggtggatca cacttgaggt caggagtttg agaccagcct gaccaacatg  60300
gcagaacgct gtctctacta aaaatacaaa aattagccag aagtggtggc actcgcctgt  60360
agtcccagct gtttgggagg ctgaggcagg tgaattgctt gaacccagga ggtgggtgtt  60420
gcagggagcc aagatcatac cacttccctc cagcctgggc aacagagtga gactccatcc  60480
ccccgtaccc cttcccccac cgccaccacc aaaaaaagaa ttatttctaa cgtaaaaaaa  60540
gtaagtaaat taagacatct gagtataaga caaaatgtta acatttttcc atattgcttc  60600
aaatcttttc cttaaataaa atataaagca aaaagtactc ctccattcta tctcatttcc  60660
cttctttcag ccattaaaat gaataaaata tacctgtata taagaacatg gataaatctg  60720
ggaagcatgg gaattgaaaa tagattacta aggctaaatg taggatgatg taaattaaat  60780
tttaaggaca cggggaggga tagcgttagg agatatacct aatgctaaat gacgagttaa  60840
tgggtgcagc acaccaacat ggcacatgta tacatatgta acaaacctgc acgttgtgca  60900
catgtaccct aaaacttaaa gtataataat aataaaaata aaaaaaattt taaggacacg  60960
```

caaaattata ttacatatat ttatggatgt gtattaaaaa tgtatgggag taaataaaat 61020 tctttttta taaatgaatc tagtaatttg aaatggttaa gaacttaatg attattaata 61080
gataaatatg aattgtgtga tttattttaa atggttaaca ttcaaacttt agcagacttt 61140
tactatgtca acaaacactt tctcaccagg ttgagataca gttttcacag tgctgtctta 61200
aaattactta agctatgtta aacactttat gtggagaatc ttagaaatat gaggcttcag 61260
tcataattgt tatacatgac ttttattttg atctttgcag ttgagtaaga attttttaat 61320 ctatttttc tttcacctta agagatgtga actataattt tttccatttt atatgtgtaa 61380
tggtgaagtg gccaaaatgt gggttagatg ttattgtatt tcaaagcgag cttgggaagg 61440
ggcgcaaagc agtctgcctt taaatgtgtt atttccagcc aggcgcggtg gctcacactc 61500
gtaatcccag cactttggga ggccgaggca ggtagatcgc ttgagcccaa agagtgagag 61560
accagcctgg gcaacatggg ggaaaccccg tctctgctga agaaaaagaa aaatagaaaa 61620
aaaaattaac cgggcgtagt ggtgggcgcc tgtaatccca gctactctgg aggctgaggc 61680
aggagaatca cttgaacctg ggaggcagag gttgccgtga gacaggatcg cgccactgca 61740
ctccagcctg ggtgacagag cgagactctg cctcaaaaat aaataaataa aataaaatgt 61800
gttagttccc ctttggagca gaaagaagtg gacactttta taaggtaagg agggaagtga 61860
acaagggcag gcggtccccc tgctagcttg gtgcctcatc tacctgatag ttgagttggc 61920
accaacccgg gcagaaataa gttgtgaaaa tggccaagca ggcagactta agatatgccc 61980
ttctgatggg tgaaagtccc aaggccaccc cgtgaaggtg aaagttccat ggcaggtgtt 62040
ctctggtttg caaatggact atcagctctc caggagagat ttgtcttgga gcacacagtt 62100
agaacttacc ctgcagggag tatctggtga ggaggacgtg aagggttata tttgcatttc 62160
tgaagggcta agtaggaaac agggaacggg aggaaagggg acaggataag agaaaataat 62220
aaaaataata gtaactcatt cctcttttct tagaagaaat gggagtactc agttaagact 62280
acatgaaggc agagggaggg aataaaaaga ggaggcagaa tttaaatagg attttttaac 62340
tcctagtcca ataaataaat gatgcccaca gttgttggtg ttggacaaga gtctgttttc 62400
tgttgctttt agatctgaga actgagccct ctccttcaca acaaaattgg cctattaatt 62460
ccagtgttac ttcatgtaat ttttttattt gtccagaact aaaactatcc tttctctatt 62520
gtcgacaatt ccattggcta agccaggttt caattgtctg ctgaatatca ggagctctgt 62580
gttaaaatta actcattcat tctgctttga ttttagaaaa cagataaaca actgatagta 62640
tttttgcaag catcttttgt tctaaagcat aatatgtatt ggtctgtttt ggtacttcca 62700
tgtatgtatt tcatgttaaa accaagaagg ctgaatttag taaatccaaa gagtttcccc 62760
catcattttc ccttttcatt catttctact gccctaggtt gggccttcct catttcttgt 62820
ctgaatagct cctgatgggt ttccccaatt ttactttgct tgttcccacc acctttgtat 62880
ttctgaatac aaagaactga ttaggtcttt cccctacctt ataatcctca gtgacacctc 62940
tttgcctgct catagtagtt aacggtatct tgtgacatcc aaggctcctc agaatctggt 63000
aagtgccttt ctagctcagc ctcattgact tctgctcggc tactcctcct ccttccccca 63060
tcccatctat atttcatcca cagttaacat ccccttgctt ttactgatga tattctgtct 63120
tcatggaaag cctactgttg tctcctggct ttttcttcct ttctttcttg ggtgcacaat 63180
ccaattggtg aataataact tctttttaa ggcctagttt aaatatcact acctctatga 63240
aaattgtctt ttctatttta attttctctt tcttatccca gccagttcat cagctaatct 63300
ggtgacttct catcacctct actgctggtc taagccactc tcatcttaca cttggattat 63360

```
tggcaggagc cccctgactg gtcttcctgc ttccgtcttt gttccacaaa gtctgtcctt  63420

cacataacag ctacagtagt cttatagaaa taaaaatcag accacatcag ttgctcaagc  63480

ccctctagtg gcttcctatc tcacacgaaa aaagctcaag acccgtcctg ctctacaagg  63540

ccttgcgtga tctgggctcc ctattatctc tgatcttgga tcttaactcc taccactgca  63600

ggctttgctt acttttctgc aggtgcactg gcctccatgg caagcatacc cagccaggac  63660

tttagcactt gctgtctcta gtacttggaa cactatctct ccaggtatat atatggccca  63720

gctcattatt tcctccagac ttttttcttt aatatcatct tattgaagaa ttctttccta  63780

acaatcttgg aaaaaataat atcctcttca cactcactcc cctgactctt ggctttttat  63840

actctatccc ctttgaattt accctgattt actttttctt atagcactta tcactatctg  63900

acatagtagt tatttgttta ttctagaatt ctagcatttt tagggcatag actttgtctt  63960

tgtttaatgc tgaatttcca aaactaaaac agagccttgg taatagtata tgctcaataa  64020

aaatcaaatg tattacctag tagttaattg ttctatctct gtaatcccat aacacttgca  64080

gatggttcct ttatacccag tgtattttgg ttgtttttgc tgtactctgc ctctagactg  64140

tgagcaactt gaggataaag atcgattttt ttctttcaat ttattttata tttcaagtac  64200

catcctaggc agcatggata cataaaattc tgcattccag gattttaaag tcttacttct  64260

atctgttccc agtacagaat aaggacctag cattgtgcaa tacatgctca gtaagagttg  64320

gctagattaa gtattgaatg ttgtacaaat gagaagagct agctctcatt tgtggtttat  64380

gatggcaact gactagcagc ttttagtgta gtctctccta tgttgttgtt tttatgtttg  64440

tttgtttgag atggactttt gcttttgttg tccaggccgg agtgcaatgg cgcaatctca  64500

gctcacggcg acccccgcct cctgagttca agcaattctc ctgcttcatc ctcccgagta  64560

gctgggatta cagacatgtg ccaccacgcc cagctaattt ttttgtattt ttagtagaga  64620

catggtttct ccatgttggt caggctggtc tcaaactcct aacctcaggt ggtccacccg  64680

tcttggcctc ccaaagtgct gggatcacag atgtgagcca ctgcgcccgg cctctcctaa  64740

gtttgtatta aaatattaat attacaaatt ccagaaaaaa ttaaactaaa ttggacactc  64800

aagccattgg cagaatttta taataatttt atgccctaaa agcctgatag gatagaactg  64860

aaaaatgtca aaatgaaatg aaagctgcaa acactagctg tggctatatc ttgctatgtt  64920

catggaaaag taaaaaagcg agaaagggct tatattaaaa acaaacaaaa tcctatctat  64980

aggggaacat cgttttaaat actcaagaaa atcaacttag gaactggaag aaatatttag  65040

aagattactt tggtgcaaat taataagaca gtaacactgt aaagttggga agacatggca  65100

aacctaaaat tgcaggctga gatgtaaaga ggactagtaa aaagggatga agattaaata  65160

aggaaggaca tttgaaatgc agcagaagaa gtgaaagtat tatttgtagt agaatagagc  65220

agaattaagt gtagaaaacc atacacatac tgaagacaaa tttaagaagc tttcccaaaa  65280

tgcaaacaat aggaaaaact gcataaaata tatggcggat agaaagtgga gatcctaaag  65340

taagacttaa cgtgtttctg gaaactgata cgagcagaag aaacaaaaat acaattgaag  65400

aacaaaatgt attgaggtca agcatgaaag ttaaaaggac ccaccaattt ccaagtaact  65460

tccattttaa aaatcacatt tagagacagt gccactttat tttttaaaaa agataaacaa  65520

aattctacaa gaaactatgg aaaaataagc agcttactta atttaaagaa ataaaattca  65580

gattgacctt ggacttttct acactgaaat gtacattgac tcaattactc tgttttaaga  65640

gatctatcta aagccaattt atatactaaa ctgtgctata tggtgttatt tttaactgga  65700

gtaaaattta tacagaagta tactaaatta tactattcta ctaaaaagtt acaattaaat  65760
```

```
aaataatggt atatcccttt ttaatactgt gacagccacc acttaaaatc atgttttaaa  65820
attagaacat gctcatgata tattaaatta taaaaagaat accgtctttg tattatatgc  65880
ccctagtttg tgtgtatata tgtgtgtgtg tgtgtatgta tgtatgtgtg tgtgtatgca  65940
cagaaaacgg tcaacaatgt taataatggt atgtatctct tgagtaagca agaaatcatt  66000
tttttccaga attctgtgtg cacatgtttt gacaatgatg aaatattaat aaaaggcaga  66060
ttgtagaaaa agagaagttg gggagacgtt gacaaaagtt ttaaattttc tgtaacggct  66120
tctcatagtg acaacactac agggcaaggt actttatacc ttcacataga aggtttgaaa  66180
tatttgctat ccacccaaag agctgctgga aatttaatac aatgggctgg cataatcaaa  66240
aaagttctta gctatagaag atattttttc aggtataaaa tcaactgagt acttaattta  66300
atgcctataa gtaggagaaa cctacataga gatataaggt aaccctggga atagcaatta  66360
aaaaatctgt ttagaatggt aaagaaatgt gtaaaggaga aaataagttt gagctagaaa  66420
tggaacccgt gaaacaagca gaagacctag agaattaatt ttcttaggaa tgtgagtaag  66480
tgttgtattt gatatactgg ttatgaggac tgataaaaga tttaaaagaa atgcttcaca  66540
tatgactcag tattaagaat tagatatatc aaaactttgt ggacatagct aagaagtacc  66600
tagaagaaac ttggtagaat taaatgttta tattagaaaa aaacgtgaaa gtctaaaatg  66660
aatgatatat gattctagtt caaaaaaata gcaaactcaa ccctggtttg attattgcag  66720
tcacataaaa ataaaaattt aaaggtatgc agatttgaaa ggaagaagta aaactgtccc  66780
tgttcatagt tgacatgatc atctatgtag atcgtaagga aggcatctac aaaaagctac  66840
aagaactagt aagtttacca aggtcatagg ctacatggtc attatacatg aattaattag  66900
gtataaatac atgacatagt ataaaacgca ttagaaacaa aaagaaattt tcatttttaa  66960
aagtactgtt tataacaatt attttaaaat aaaatactga aggataaatc taacaaaata  67020
ggtacagtat ttatacactg aaaactataa aacatttctg agtaaaatta aagatactct  67080
gtttaaatgg agagatatca tatgctcatg gtttaaaaga caccacattg ctaaggtatc  67140
agttctcccc taaaagacct tacatattta acacaatctc atgcaaaaat cttaccaggc  67200
atttttatgg aaattgtaaa ctgcatgtaa attttgtatg gaaaaatcaa aggatataaa  67260
atagccagaa caatttttaa aaagaacaaa attgcaagaa tcagactacc tgatttcaag  67320
acttactata aagtagatta acccaaacaa tttgaaattg atatatggat agacaaatag  67380
atcaatagga aagagggaag tattcagata cagacatgaa cacatatgac caattgattt  67440
tcaataaaga gtccaaggca gctcaacaag ggaaaatatg caggtaatct tttcaacaaa  67500
tggtgttaga acaattggat atctgttaaa aagagaagaa ttataaaccc ttaactcaca  67560
ccatatacaa caattgactg aaaatatagt tctaaatgga agagctaaga caataaatct  67620
acttgaagaa aacatagaaa atcctcctaa tgtcaggcca agatttctta ggatataaaa  67680
agcaagagct ttcaagggaa aatattgata attaagtatt ttgggaaagc aggaaaaaag  67740
ccaagctaca ggctgggaga aagtatattt ttaaatgtat atctgataaa agacttgtag  67800
ccaaaataca taagggactc ctaaaactca cattaaaaac aaaagcaacc taactgacaa  67860
attaccccaa atcgccaaaa taacccaatt aaaaaatggc caaaagaccg gaatggatat  67920
ttgtcaaaat aggataagca tatgaaaaat gcccaatatc actaatcagg gaaatgcaaa  67980
tcaaactaca atgaaatact acttcattta gaatggctat taacaacaag ataactgtta  68040
gcgaggatgt ggagagaaga gaacctttac atactttcag tgggaatgta aattagtaca  68100
gccattatgg aaaatagtat agaagttcct tgaaaaatta aaaatataac taccatgtga  68160
```

```
tccagcaatc tcactactag gcatttatcc aaagggaata aaatcagtat gtcagaggga  68220
tatcttcact cctgtttatt gcagcactat ttgcaatagc caagatatgc aatcaaccta  68280
agtgtccatc aaaggataaa tggataagaa aatgttgtgt ataggccggg cgcggtggct  68340
cacgcctgta atcccagcac tttgggaggc cgaggcgggc ggatcacgag gtcaggagat  68400
cgagaccatc ctggctaaca cggtgaaacc ccgtctctac taaaaataca aaaaattagc  68460
cgggcgaggt ggcgggcgcc tgtagtccca gctactcggg aggctgaggc aggagaatgg  68520
cgtgaacccc agggggcgga gcctgcagtg agccgagatt gcgccactgc actccagcct  68580
gggcgacagc gagactccgt ctcaaaaaaa aaaaaaaaaa aaaaaaaaag aaaatgttgt  68640
gtatatgcac agtagaatac tattcagtca gaaaaacata atgaaatcct gaggttgggc  68700
atagtggctc atgcctgtaa tcccagtact ttgggaggct gagacaggag gatcacttaa  68760
gcctaagagt ttgagacaag cttgggcaaa atagtgagac cccatctcta caaaaaacat  68820
acaccaaaat tagctgggca tagtagtgcg cacctgtagc cctagctact caggaggctg  68880
aaatgggaga attgcttgag tctgggaggt cgaggatgca gtgagccgtg atggtgccac  68940
tgtactgcag cctgagtgac agagcaagaa cctgtctcaa aaaataaaaa aagaaatcct  69000
gatcctgtca tttgcaacaa catggataaa tctgaggaca ttatattaag tgaaataagc  69060
caggcacaga aagatgtaac cacaagatct cactcaaatg gaatctaaaa atgttaatct  69120
catagaagtt gagagtagaa taggggttac cagaggctga gaaggggaca cggggtgagg  69180
ggaaatgggg aaaagatggg tcaatgggta caatattaca gttagacaga aggaataagt  69240
tctgttctat tgcacagtag gatgactata gttaacagta atgtattgca tatttcaaaa  69300
tagctagaag ggaggatttt gaatgttctt actacaaaga aatgataaat gtttaaggcg  69360
atggatatac tacatatcct aatttgatca ttatacaata tagacatgta tcaaaacatc  69420
acattttacc tataaatatg tacaattctt ttgtatcaat cataaaataa aacctaaaaa  69480
gtgaaatttc tgtgttacaa agggggagaa cacagtctgt attacaattt ttttaactca  69540
aaaggtacaa aatatttgaa cagatgcttc aaaaaatatc aaatagttgt atagaattac  69600
ataagtttgt ttttattttt attatatata aatatgaatg aaataagtac atgaaaagat  69660
gttaaacatt attaatcatc agaggaatgt taatttaaac cacaatgaga tctgcataca  69720
taccagaatg acatcaatta aaataacagc tgacaatacc aaatgctgac aaggatatga  69780
agtcctcata tattgcaagt gacaatgtaa aatggcacaa ccactttgta aaactatttg  69840
ggagtttgtt agtaagcata cacttaccca gcaatcatat tcctaggtat tcaagaaaaa  69900
tggaaatgta catcctcaca aaaatttgta catgaacgtt cataatagtt ttatacacaa  69960
tagaaaaaaa tggaaataat tggtgagttg acaaataatg aagtgctatt caaaaataca  70020
atggaatgct gatacgtgca aaaaccacag ataaatctca aaagccttat cacataagat  70080
tatatactat atttttccat ttacataaaa ttctggaaag gtaaaactag tggaggaaac  70140
aggtacatga ttgttgaggc caggagctag ggaggggatg aactgcaaag aagcaaaaga  70200
taattggaac aggaatggaa atattctata tcttgattgt agtagtagtt gcacaacggt  70260
gtacatttgt caagccatca gcttttgcac ttaaaaactg gtatactttg cggaaaagta  70320
taccacataa aacaaaaccc ccatacaaaa aagaataaat taggccttag aatgaaaaga  70380
atctcaagtc aatgttgagg agcaatttag acgtgaattt tttaaattcc acagagaaag  70440
aaagatagta aaataagcca tgtgtgttca aatttacaat ttctgctgac ttgaatcatc  70500
agggtatttt aaaatcttgc tgtaaatcag attcccatgt tccaatcttg cagaagccgg  70560
```

```
gaaaattgga gatgatggtg ctattttgta agggatacgg aagtgggcaa gtctaaggac  70620
ttgtttatac acatagacca gggagactga acttagtact gggtaaaaaa aataaaggtc  70680
atcatggaac agatttgcaa acaatgaagt aaacagaata gcagagattt ggctttgtaa  70740
aaagaaaaaa aagcgattgt gccagaccac ttcagcgcct ctagttgctg aattgcagga  70800
ctggtagttg aaccaaaagc aataaacata atgcatcttg gctgtggtca gatattttga  70860
tttagtcaaa tatgaagccc tcaccactaa aattggaaaa tatggtttgc agtacagata  70920
cagtactagc tgaaaagtga tatctgaatt gtcctggcat gacgtggaga gcagaggaaa  70980
aagagaagtg taccacactg ggaatatcac ttttgttgtt gtagttgttg ttgcttgctt  71040
gttgctttta atttttttag gtttcagatt cagtaggtac atgttcagta ttgttacatg  71100
aatatattgt ataatggtga ggtttgggtt tctagtgtac ctgtcaccca aacagtgaac  71160
attgtaccca ataggtattt tttaacccgc atcccctcct accttcctca tttttggagt  71220
cctcagtgtc cattatttcc atctttatgt ccatgtgtat ccttttgggg tttttgtggt  71280
ttttttcgt atgtttagta gagactggat ttctccatgt tggccaggca tgtcttgagc  71340
tcctgcctgc ctcggcctcc caaagtgctg ggattacagg catgagccac tgtgcccgac  71400
cacatgtgtc ttcactactt atctcccaca tataagtgag gacacatgat acttgatttt  71460
ctttttctga gttgtttcac ttaggataat ggccttcagc tcaatccatg ttgctgcaaa  71520
ggacatgatt tcagggaata gcattttgaa ttttgggtga tgatcctatg gtgtgtttga  71580
agcattaaaa cgtttgtatg ggtagaacat ggggtgagaa atgtgtgtgg gtgggggtgg  71640
aggggtaggg ggaattagag atagataagg ccataataca gagggcctca taaagtcctc  71700
aataaaccat gttaaagagc aagactgtat ccttgaattc ccagaagcag ctggtgtaat  71760
cgtccaggct gtcttccacc tagcccaaag tttttcaac tctatcactt gctgcctctc  71820
cctaccatta aatgagtaag caatatactg agaaattaat aaaactatgt taaatagacc  71880
acttttgagc tccattttaa tgcttggaga agagtcggta agcattgtaa ttgattcaga  71940
aaagaaccac aatgttggaa actagaaaaa ggtaaacatt tgcatggctg agttaagaga  72000
acagagacat aagaaactgt tattacagga ctaggataga ctcatatacc agttactaag  72060
caggttcttg ggcaagtcct ttctgtacat ttattttctt atttataaaa tagggatgat  72120
aattcaagtc aattatctgt tatctacaat tctgaagttc caagagctct gaaaatcaga  72180
agttggttca gttttatttt gatttcttaa gtttgtggca cactcatttg atggtgaaac  72240
ccaggtttcg tagtcattta tcagttagtg tgaatattta tgaattctgc agaaataatg  72300
tttgatctta tggtgctacc ctaaattctg ctggatacat tcatatgtta tgcaaactac  72360
tatttttcta aaatctaaac aattctggat tctgaaaatt ctggcccctg tggtttcaga  72420
taagagacag tatgcttgta ataccttcct cttagggttg tatcaggata aaatttctta  72480
aggcagaact cagtaaacga tgaagctatt attatttatc attaattaag cttaaaaatt  72540
agattcccac ccccatcccc gagaatgaac aagaattagc acttgacgat ccttaatttt  72600
attcttaatg cttttatact gtactctctc gagcttgatt tatagtatat cagttattaa  72660
aatggaatgt tttccttaag aaacttctac gctgaacact taaccttcat ttctgcaatc  72720
tttacatact tggaaggata ccttatttgc ctttaggtat tagttgacag acttattttt  72780
cagtcatctt tcctaagggt catcttacga aattcatggt tagattatgc gttatatacc  72840
tcctaacgaa aacacgaatg gatatgctta ttttcttcaa gttctcaata aaaggaagtt  72900
cttaacatgt cataaaacaa gttctgtgta agtctttagt taaaagcact agagcaaaaa  72960
```

```
tacccatcta gatttcattc agtgtttccc aagtagaatt ttatttttgt ggttgaagtt  73020
tggcatgttt cctatttctt caagctatat aaaacccttt tgctgcgtct aatccatggc  73080
ctgcggacat ggaggactga ttttgcaata cttttctagc attgggaaac ttctaactaa  73140
aaattttgtg tgctggaata cttggaagaa aaggaaaggt catttaaaca aatactatat  73200
tttaaaatga agaaataaag caacatttta aatgtgtgat ttttgttaag atacttgcca  73260
ttagtgagag ttagggtggg acatatcagt aacgaatccg attgccacta tggctctgcc  73320
cccccaccat ctttcctctg ggaggatgtt ggggccaact tacgattgca acctgtgtgt  73380
gtgtttatcc tttgtttgga tacatgttac taggtgcccc actcttggcc agcaattcca  73440
gtgcctgggt ggtttgcctg agcaaagtgc ctgagtggct aggaatgtag agatagggct  73500
ttgacccaga gcacagggat gataaggttt actatagtgt aaggattaga atgaaggttc  73560
tcttctgctt cagaagtggg aagaggaagc aacacaggat gggatctcta tctggttcta  73620
ggtctcaggc tttctccagc ccgttttgcc aacttacaag caactaacca ccactaaact  73680
tcctctccct ggagaaggaa aaatttcact cacttgtgag tgagaagatc tgcatccaga  73740
tcctttctgt gccatgatta gctgtgctac atcaggcccg gtgttttcag gagtttagga  73800
ccaaacagcc cctttcagct cttgcattct cctagtcttt gacatcagaa ggaaagtgca  73860
ggcgttcaag ggagttcttg ttttacagtt tcaagcgatc tgacgtcagg cgaaatctct  73920
tcactctcta acagatattc catcttaaaa aaaatcccat gaaccctaat tcctgtgagt  73980
gtctctaaag tatattaaag actggattaa ttgtaatcta ggcagaaatc tgtctttgtg  74040
gttgttgttt aatatcactc agtacatgcc aatactcttc tttcacttag cttctggtaa  74100
tctatgaagc tactcgtggt ttcattcatt taaacccctc tgagcctcag cttcttcatg  74160
ctaaaggaaa ataacaggaa ataatggcat aaatgtgttt tgataaacat aaaacctttt  74220
gtaaacatgg ggttttattt atgatagcac aaaatattaa tataacttcc tctaataaca  74280
ttgacatacg tcacatctat agtagccagt agtaaacagg cagcatgcag ctctaaaaag  74340
tggacagatt ttcattgttc tgatttggaa tgtaacaata tctcctgttg gttctctcct  74400
tcctttctcc actggcccca actctaagca gtattccact gaactgaaga aactctactg  74460
ccaaattgca aagacatgcc ccatccagat caaggtgatg accccacctc ctcagggagc  74520
tgttatccgc gccatgcctg tctacaaaaa agctgagcac gtcacggagg tggtgaagcg  74580
gtgccccaac catgagctga gccgtgaatt caacgagggt aagcagaatt tgaatctcta  74640
actgttcaac ctccttgaag gtcaagattc tgtgggcatt tttgtttgag acccacctac  74700
ctgattcaga cttctgcact ccgatggcag atcagtctgc cttttttttt tttttttttt  74760
tttttggctg acagtatcta agaataatga taaataaatt catggctttc acagtggttg  74820
aactatttaa tattagtaat tactagatga cctgaactac tggttatctt tactccttcc  74880
tgcttccttc tttttatttt tcttgccttt aaaataaaat aagaggctgg gtacggtggc  74940
tcatgcccgt aatcccagca ctttgcgagg ccgaggtggg cagatcatga ggtcaggaga  75000
tcgagaccat cctggctaac acagtgaaac tccatctcta ctaaaaatac aaaaaaatta  75060
gctgggcatg gtggcgggca cctgtagtcc cagctactcg ggaggctgag gcaggagaat  75120
ggtgtgaacc caggaggcca agcttgcagt gaaccaagat ggcaccactg cactccagtc  75180
tgggcgacag agcgagactc catctcaaaa ataaaaaata aatgaaaaaa aaataagagg  75240
gtgccaggag actacatggt agctattcta cttggcccag gctacagttt cttcagattt  75300
agtgttttcc cagaaagatt ctcaagtcta gaccagttga gacctggaag ggtaagagaa  75360
```

```
aggagcacca aatgaaagaa ataatgaaaa aaccagaaga agaaaaagga aaaaaagatg  75420
agaaggcaag taatgggtaa ggggaataaa tagaaggcct agagcatact gtggccaatc  75480
aaataaagga ctgggagtgg agggatgagg tatcatgaag gccaccttta gacgctatat  75540
ccatgaataa gtcatgcctc atattctaca tctcagatcc tacaacaatt tagcagaaaa  75600
ggtcagcaat gccaagagtt cccttagatc tgatattata gttccatgaa gggagactaa  75660
acagagagtg ctgaaaagtg gaaggtaaga gcaggataaa gcataagcaa tcctcaaaga  75720
gtattgaggg tgccaaaggt gttgggggtt aggatacttt atagaaaaaa tattaaaata  75780
taaggattga taaatataga gagtataatt gtagagaaaa tcaatggaag aagaaagaga  75840
atggatcgga atttaaaaga agaaaataaa gtcaaaattc tctttaaaaa actatttttt  75900
acacattaat ttcaagtcct tgcccacatg gccacattat ccgtacattt atctcttgct  75960
tttcacttaa caatctgcca taaagaatat tgcaatatag atagacttca ttatcagcct  76020
ccctaacttg gtatttcacc aagataacat actatttgta agcgttttcc catttttttaa  76080
acataaaaat tgtttttagt tttaaccata atagatgatg cagcagagaa cattttgata  76140
tgcttcactt tttactttta ttgaatggtt tttgtagact gggactatag gacctaagag  76200
ctgttaaaaa cagctttacg ggtcccagtt cttggagcat cttctttttt ttggagctct  76260
gctaaatatc acaattttat gaaactttac tcagtctctt ttttaaaatt gcatcccttt  76320
tcttacaccc aacttgggac tccttcaaca cacaaacacc agaacgtttc ttatctttat  76380
aatcaacaca atgtttaaaa gttgaggagg aggaaagaag aagaagtgga agtcatatcc  76440
ttgctatctt ctgcttctca gtgtatttgc tggtcagact tttgggcagc attttctcag  76500
ttaaactgat tttttttaa attaatttgc ttatttccct ttcattttcc aggaagctgg  76560
caaaatttcc tccacgatga ggtcagagat gtagttatag agttccataa agcttgaatc  76620
attaatctta aactccaaat tataggactg ttcccttaac tgtagatgtg cattccagcc  76680
ctttctgttg ctataaaggt tatgacacct tcatgtattt gatatctggc tatgggatct  76740
gttcgtttct tcaaggatgc acattttctt tattatacag actatttctt ttgccaccaa  76800
catcctgttc atgcaatttc attttatttt ctttattttt aaggtaaaga actaactctt  76860
ttattgtttt ctgctctgca ggacagattg cccctcctag tcatttgatt cgagtagagg  76920
ggaacagcca tgcccagtat gtagaagatc ccatcacagg aagacagagt gtgctggtac  76980
cttatgagcc accccaggta aaaagcaaaa aaccaaacca aaaaacaaca cctctatgga  77040
ctgagtagac ttgagagaac atctgtttca gcaacaggga tgtttctagc atctatcact  77100
gtcttagttc ttgtcatcaa atatataata tttttgtatt tttttctacc tgttctccac  77160
atgctttccc ttcagaatac ctaaatatgc actgaatcaa cttggtaaca tggctctgtg  77220
tccatattcc catcttaagg gcagataaca attgaactgg caattgggtg tatacatgag  77280
attgttttat ccaactggca gttggacggg tagtggataa gcaatagtag tggatgcaag  77340
tgttaccata agtgggaaag cctaagaggg atctcttagc tgaagtttga atgaacagat  77400
gatagatttg taaatctgtt gcatgaagca gagtagtgtg gttgaaagta cactggtgta  77460
acaggaccca agttctttgg tttgctggct tgctgtgtgg accttcggca actctctctc  77520
tctaggcttc agttgcctta cccgtacgta tgtactttgg actagattat gtttaattct  77580
gagaacattt tgagctctaa gatgttatta atggaagtat atattcaaat ctatattgta  77640
ctgttttatc cacacaggga aaatattctt ggagcattgc tactgttttt ggcaattatc  77700
cccagtttc ccttttcagt gatattcatg aaggtggtat agcctatttg aattacatga  77760
```

```
tgtggatcag cttacaaacg aacaggatca aagatcacaa aatgttaaag cctgtctcac  77820
ctaaggtagt gttcagtgtt gcaaacatta gctttaagct tccccgcagg caagatgaag  77880
aaaaatctac aacagggttc agagtttgcc cttttaggag gaagcgtatc acttcatcag  77940
aagtggaatt ccttaaatag agggaagaac tgagaaggaa caacgtcagt ttaaaccctt  78000
gttaacacag attatttacc ccttgttttc aggttggcac tgaattcacg acagtcttgt  78060
acaatttcat gtgtaacagc agttgtgttg gagggatgaa ccgccgtcca attttaatca  78120
ttgttactct ggaaaccaga gagtaagtgg cgtatgtaaa attgtcattc tacacaaaaa  78180
atcacgagca gagggcaaag tgaaatcgtg gctgctttat cattaatttt gcatgtgcag  78240
cggagagctt gtcctttgtg ctctaaatcc ttgctacaaa cggttacata aaagatctaa  78300
gaaagtggag acaaaggaag gtgggtaaag ttagaaggaa aaaaagagct agaaaagtgt  78360
gcaagtcact tcatacctga attcttgaca tttgactgga attgttctga ttagaccatg  78420
gtcctcaagg catttcacag ttttttttaa gtctgcgctg ccttagggga ttttatcctt  78480
gagacatcca ctggcttaac tcaagtttcc ttcaaaatat gtagctaaat acagctgttc  78540
agctaatagc tcagaggttc tttggagaac aaatggaatg ttatttacta atattacttg  78600
tggcatgtta gcacttttgt gttctgccaa gtgcttttgg gtccattctc aaagccgcca  78660
tggctaagct ggtagtacgt tggcgatggc ccatatggga agtggaagtg gtagatcttc  78720
aggggacttt caaaatgctt tgaatttaac tctttcttcc cctttattct aattcctagt  78780
gggcaagtcc tgggccgacg ctgctttgag gcccggatct gtgcttgccc aggaagagac  78840
aggaaggcgg atgaagatag catcagaaag cagcaagttt cggacagtac aaagaacggt  78900
gatggtacga agcgccgtaa gtagatgtag tggccaaatg gggtagggtt gaatcttctc  78960
cagatgttgg agaatggggt gatattggag aagctgcatg ataagacctg tgaccttcag  79020
cagcaagtgg gacgtcagcc ctcagagcca gtgagaatag gtatagcatt gaagtggact  79080
ccaggcatgt actacagctt tacaaaaaca agtagtcatt gtgacaattt ctcagtccag  79140
ggattctcaa aatgtgactt ccacaccagt agcataaaca tcatctattc acagacacac  79200
accagcaaga tacgggcttt cctgcaacat tacttaagcc aaaggctatt tcccagcata  79260
ctgaatttct tttatgtatt cttccctacc atccttccac ctccttattg ctaggatcac  79320
aatcaatgta aaaacaattg tccccagtta aatggacgct tagggctaga gcctctaatc  79380
ttacatgtgt tgctggtact actgtctttt taatatgtat attaaatctg attaacatta  79440
atatttaatt attaagtata tttaatatgc attagtgctt tagaagtgtt cccaggatga  79500
aacttgcatt tttcctccac cagcgtttcg tcagaacaca catggtatcc agatgacatc  79560
catcaagaaa cgaagatccc cagatgatga actgttatac ttaccagtag gtcttccttg  79620
ggtgttcatg gttgcttcat tttaaccttc tttgaatggg cttttacagt atgatcatca  79680
tctcattatc tgtgacaatg ggaaaggagg tgtcttagtc agttgaagct gctacaacaa  79740
actaccgtag actagatggc ttataaacaa cagaagttta ttttctagag tctggaagtc  79800
tgagatcaag gtgcccctat ggtcgggttc tggtgagagt tctcttctga gttgcaaact  79860
gccattttct ccttgtattc tcatatagtg gagagggcta gagagctctc tagggtgttt  79920
tttttttttt tataagggca aaatcccatt tatgaaggct ccactctcat tacctaaatt  79980
acttcccaaa ggactcacct tctaatgtca tcacaatggg gttaaaattt ccatctgtga  80040
actttggaag gacagaaacc ttcagtccat aatggggaag aggggagacg gttgagagct  80100
ggtgatacaa aggagagaaa atatgtgttt tttaaaatta gaatattatt ctttctctcc  80160
```

acagttttgg actgtattac tagcatgagc ttctctactt acctacccac ccaactaaag 80220
ctaaactcct aacagaattt ttcttaccct aatatttaaa attaatttgt ccttcattat 80280
ttgagaatga taagattatc ctaggcagca tggccataga aatttaggcc gaaaatgttg 80340
tcagaaaaag ttcacaaaat tgataatgca gcaatgatag ccttgacttt gatgtctttt 80400
aggcagcact ataaagaaag ccaagcaagg cagaagcctg aattacagtc agccctccct 80460
atctgcctgt tccatatctg cagattcaac caatcacaga tcaaaaatag ttggaaaaaa 80520
acaataaaaa aatacaccaa tcaaaataat acaaatataa caacaatata gtataacaac 80580
taattgcatg gcatttacat tatattagat attataagta atctagaggt aattttaaac 80640
tatacagagg atatgcatag gttacgtgca aatactacac cattttatat aagggacttg 80700
agcaacctag gattttagta tccatggggg ccagatgggg gtgggtagtc ctggaatcaa 80760
tgctctgctg atatcaaaag acaactgtgt atgtaaatgg ccagaagtct tagcccaatt 80820
attatgtaag aacctcatta attcctacaa gggacattac ttctcttgca atcactaatg 80880
agatcacttt attagattat ggttgcagtt agttagttga attcttattg cattaggtct 80940
ttgccatgta gggtggcaat gacgttttgg tggctggcat agcccttgat gccatctaaa 81000
gcgatgacat gagacacagc caagcagggc caggagattt gaccatgaac tactaccctg 81060
ggattgaact aacgaaagtc aacggattta ggtgtgctgc actttcttcc tcatcttctt 81120
tgggtcctga ctctcagggg aataaattgc cagtagacca atcagacggt gagttagctg 81180
agattcccag tgtcttgttt ctcaaggtat atatggaaac tgacttgtga tgttaaagta 81240
aaacattacc ctgatacact aaatattcca aaagtcttaa tatgttttca gctgataaaa 81300
caggaactgc ttgaaaaatt attttaaaat ttcagtttgt actaagaagg aggtatcctt 81360
cttagtgtca tgtctcaagt tgagagaaga cttagcctaa ataatttatg ggtgaggaaa 81420
aactccatta atttaatata tattttgttg gtgtttggtg agtggcaaat atgctagacc 81480
ttgagcattt agagttcagt aggatacaat tcttacttc aactaccttg ccttctattg 81540
aggacacaaa cagttataat gtaataaata aatgtaatgt aataaaataa atattcctag 81600
atcaaggcct agtgctgtgt gagtacccaa gaagctccaa agatgcaaaa actataaata 81660
agagtaagat caagaaaagc ttctcagaga aggggtccca cagctgggat gagtaagagt 81720
taattcaaca aaaggtggag aacatttttc atttctgaat tctgactaat tctgcctttc 81780
ctactgggtg cagcaactgg ggtaaggcag ttaaagtgcc tagggtgcaa aatttaaata 81840
gtcactcaca cccaaggcaa tgcagttgtg ctaagtgcct ctcttgcctc actctagtcc 81900
tggcccggct catccgtttt tttggttttt gtttgttttg aaacaggatc tcactttgtt 81960
gcccaggttg gagtgtagtg gcaggatcat ggttcactgc agcctcagac tcccagactc 82020
cagcaatcct cccacctcac ctccccaggt agctgggacc acaggtgtgg gccaccacgc 82080
ccactaattt ttgcacattt tgtagagaag gagttttttt cccagggtgg tcttgaacta 82140
ctgagctcaa gcaatctgtt ccctcccaaa ttgccgggat tgtaggtgtg agccaccatg 82200
tctggcccct gctcataatt gtaaaagcct ttaagagctt ttatttaaag attttaaggg 82260
actctcttaa agagagaaac atattttatc ccacatggaa acttttatcc tatcaaacat 82320
agttacaatc tattcttatt ttttgtagta gtttagtttt atgaaggtgt tgcaaaaatg 82380
gtattggtgg atatgaatca tctcatcgct cctaagagaa atataggatt gggttcctat 82440
gcacctctgg tcacatacat ttcacaacag aataatatat cacttcgttt gttgtgtgtt 82500
tctgttaaga gacattttat ttaatatata ccgttgactc attaacatca gactcgtggc 82560

```
caattagcct tataactcat gcctgaataa agtttctcta acacacacac acacacacac  82620
acacacacac acatattttc tccataaggc atggaacgac cttctctcac ttagggacac  82680
tagatagcac ttccgcactg cccttgaggg tcttttaaat aacaaaatca ccaatgaaaa  82740
gcacaaaaat gtaaaacacg tggcgctaaa tagaccatga aaagaacgtg ggtttacggt  82800
ataagagcta caagatgaca gagcatctcc ttgttcgaac cagctgggaa tgcacacagg  82860
tgactcaaat ttttcatcac tctgcccggg tctgaaagac cacaaaaggg ccaagagtgt  82920
tgattttcat gttacaaata aacgttagca aataaacaaa ttgcaattac ggaatcctca  82980
aataatgagg attgaccaca cttctaacag ttctacagct tttcatgttt ccttctttcc  83040
ttctgctcac ttccataggt gaggggccgt gagacttatg aaatgctgtt gaagatcaaa  83100
gagtccctgg aactcatgca gtaccttcct cagcacacaa ttgaaacgta caggcaacag  83160
caacagcagc agcaccagca cttacttcag aaacagtgag tgtatcaacg tgtcatttta  83220
ggaggcatga gtgagggtga ctttatttgg atcagcaata gggtgattga tgagcaatgt  83280
ggaacataat gggagatagc agattgtcat agattcagat gacctggtat ggcaaccctc  83340
tttcagttgc aacctttttt acgtgtctta ttataacctt cccttcagaa ttccacttat  83400
gttctgaaat taaatacaaa ccatttctgg tgaattacaa agaaactcac actaacagtt  83460
ctcgtctcta tatgcctggt ccatacacac taacagtaag tacacactct atttggtagt  83520
gatgtgtata tttgaaaaca tgaaatcttt tctcatccca atggattgtc ttataaatct  83580
cctgggatgc acactatcca cttttgggaa taacactgta gaccagggat agcaaatagg  83640
ctttactata atataaagtg acttgtttga atgctgtaat gagaagaatt ctgagaccta  83700
gtgcatgata attggggaaa tatctgggtg cagaaggata aggtagcatc atgttgccgt  83760
attttagaat ctctgctcta gattgtcttc cagcagtaca tttttggcat aaatcaagcc  83820
agatttttca agtatattac catatacata taacctattt atatgttaag ctttgccttg  83880
aatcttggat ctttcctaaa gtgattttat gactgactag aatagaatag ctcttatgaa  83940
aggatgagag gttgaccaat caggaccttg tttatattta cctttctgtg gttaaaaata  84000
atcacttgtt agtttaatta aaatatgata tgtgtcctgg aagtattgtc agagactctg  84060
tagataagtg taaaatatat acattatgag tccacttgag taatgtagac tttcaacttc  84120
atactttagg caaaaaagaa gtcaaaaact atcttccaga ggcaaagatt atattttaca  84180
atagaaatgc aaatgaacaa taaaaatggt tattttctat gttattagct gttgtaggga  84240
gtcagctgtg gaaagtgtaa taaagagggc ttatgattat tattattatt attgagtctc  84300
gctctgtcac ccaggtagga gtgcagtggc actttcttgg ctcactgcaa cctctgccta  84360
gcgggttcaa gtgattctcc tgcctcagcc tcccgagtag ctgggattag aggcacctgc  84420
caccatgcct ggcagatttt ttgtattttt tagtagagat ggggtttcac catgttagcc  84480
aggctggtcg cgaactcctg aactcaggtg atccacccac ctcggcttcc cagagtgctg  84540
ggattacagg tgtgggccac cgtgccggcc ttgttattat gttttaatca atatgaatgt  84600
atctctgata gtaaagaaac actttctgag cacctgttat ctacagagtg gagtagacgg  84660
cagggagaaa agaggcacat tctctgttca aaggactcta agctatttga gcatccaaga  84720
tccttttggg cccgaaggga tctcaccatt tacttttagc ataaaagttt tgcaaatttt  84780
aatggtatgg ttttatttgt aagcctgagc agaaagttta atcacacagt gtattctgaa  84840
ggagaattag aactcagagt tgcagacaca atttccattg ctaatcatat ggatgttttg  84900
ggatatcaga tggaaatata tactaacata tttaagtgga aaatgattta gttcttataa  84960
```

aaccatacaa ccaggatcaa agaaacagag acctgtaaca tcatttatag acccaggagg 85020
gatatctacc tttcctaaga tatgtgtgtc atggtattaa gaaataccct caaatttcct 85080
cctgttcact ctgaaagttt gactatacca aaatgacctc caaaacatca ctaagtaata 85140
tatcatgctg aactagttgc tcttcagtac tctttcctgt cttttttttt ttttttttt 85200
cagttaataa gaaaaggtct catatgtagt acaggaattg gcaagctgct ttttgtaaag 85260
tcctggtagt aaatatttag attttctggg tctatattgt cttttgcaac tactcagctc 85320
tgtggttgta gcacagaaac agccgaagat aatgcataaa ggaaagagag tggctgttcc 85380
ataaatggaa ctttatggac cctaaaattt gaatttcata taattttcac atgccgtgaa 85440
atattattct ccttttgatt gttcctcccc ctattaaaaa ctgtaggccg ggcacggtgg 85500
ctcacgcctg taatcccagc actttggtag gccaaggtgg gtggatcacg aggtcaggag 85560
ctcgagacga gcctggtcaa tatggtgaaa ccccgtcgct actaaaaata caaaaattag 85620
ctgggcaagg tggcacgcac ctgtagtccc agctacttgg gaggctgagg cagaagaatc 85680
gcttgaacct gggaggcaga ggttgcagtg agccaagatt gtgccactgc actccagcct 85740
gggcaacaga gagagacttc atctcaaaaa gaaaaagaaa aaaaaataca tacatatata 85800
tatatatata tatatatata tatatatata tatatataaa ctattcttag cttgctgtag 85860
tttgatagtc tgtcttatag ataaatgcgt ggatctcctt tcattgcttc ttgaggctcc 85920
aattttgttt gataggtgta cttggaagtt aatatgtata ttccaagcta gaaagttatt 85980
aaaagatttt aggaaatcct aaagtggttt ttcaggtggc atttcagtat ctaataaaaa 86040
gcaacaccag ccttgaacag atatcttttt tgtctgagaa agtgaggcat gcccatccag 86100
atataaaatg tagttaacga cacaacctca ttgtcagatg aggctggaat agttgacttg 86160
attcacgtca catattctta ttgaagatgt gctatgtgaa agcattaagg atagaggtga 86220
gaaagatgta gctcctgcct tcccatggtc tacaatttaa tggtgaattt ctaaccttaa 86280
cactctgagt ttgaagaaag ctctggaaat ttatcctcag cattgtgcaa gttaatagga 86340
caattttaaa cagtttccat ggatcatatg agaaaaagaa tagtttcatg tcattgtttt 86400
agaaacttga caagccagga ggattgacat cattcagttc aggggcatat gctaaatgta 86460
tttgttttta tggcatacat gaaaatacat aaccctcttt ttctatacga tgagtatcca 86520
gtgcttattg tctgaccggc tcacattgct ctaaagggaa tttttattc atatttcata 86580
aaataatctg tgtccccaga gaagaaaaca catgttaata ttgtgttatt tttaaaagca 86640
cacaagattt tagggacata tttacacttt tttgcatgtg tggccacaga tagatagtaa 86700
agaactagta gcttcatagt tccctggtgt gttcatttaa ctgtattata tgcatgcttt 86760
tgagttggta tctcacagct gtgataactt gtgcatggaa atctaacaga ctgcaaaatt 86820
aaatctttgc aaaatataga catttggtct aattatgtct ttgtaacatt atatatacat 86880
gggtctccag tgattgatat gcatctatat aaatccttca gttgaattct tcagctgagt 86940
ttttttagct cttattttca tgcaaatctc caagaaagag catgaatgac taaacaaaga 87000
aaaacaaaaa tctaatttcc tggcaatcat ttgaaaagaa taaatcagct tggaaaatac 87060
ctataatagc ctgtgatttt ctttccaaaa agatagtacc aattttatgc tggtaaggaa 87120
tcaattttgt atttttcttt atagtagagg gaaaattagt gggaagagaa cgtactttct 87180
gtaaggtggc actacaatat ttttacttta attacttcta ttaggttccc actatgtgtt 87240
ttcttctgcc tgcttttcat ttgtgcatgg tttttctttt taaaaaaatt tcttcgcgtt 87300
taccttcatg atcataggct ttatcgaaga tagactttac agagctgctg tgaatcaaat 87360
tgttatagat acaagtaggc tttatattac gaagaaatgt gattttagtt gatttgctta 87420
cattggaata aatatagaga gttatgtttc tagatgccag aatctaatag aaagacaaat 87480
cggaccctat ctttagactt cttgccatcc tattatcaag ggacatcaac gcttaagaca 87540
gctttgcaga agcctcttga gacctattta gcaacgtttt gacttctgta cttcagatca 87600
gtactatttc ttttttcatt tgttagttgt tttcccttat tcttggcttc caacataaaa 87660
gcgaggctga catcactttg ttacagtctc gcttaggcta gctcttactt tcctctggaa 87720
atttattttt gagcttctac aggatgaatt ttatttaaat gataaaacag atctgtgaca 87780
tcctgatgag cccttagtgt ttccttctct tttatgatta cttgacaatt gtggctcatt 87840
agtaacacaa gtcagagatt attagaacaa agcaggatct ccaagtccat ggttccagcc 87900
cctcacacca tagccggata aactgaggct ctgtgaattt atagccagtt tataataaag 87960
ctaagactag aatcagattt agaacataga gctctttgta atgttgtgtt ctgctacatt 88020
ggcagttaag taagtagtta attataaaat ttaaacatct atttccattt ttctgtctct 88080
tttttgtagg attgttttag agatggggtc tagctatttt gcccaggctg gacttggact 88140
tctgggctca agcgatcccc tgcctcagcc tcccgagtag ctgtggacca caggcacacc 88200
ccactgtgcc tggcacgttt ttctgactct gttgttagtt acttggtatt tattcttgta 88260
ggttcacttt aaagtcctgt atctttaaac ttgtttggcg atggttatca tcaagaatat 88320
tgatattttt ttctcagatt catgtatctg agggagaagc aggcagtatt ttcagtatta 88380
tcaatgtaga aaagagaaag gtacacggtc tccaaactga tagaaaatgt caacaccgta 88440
tttctaggtt agacagagaa atcctccacg tttccagaat atctgaaatt gccagcttta 88500
taggttaaaa agagatgaat attgataatt tcatatgatt caccccttata gttattatgg 88560 aactacacaa gcttttacag tttccttttt tttttttttt tttttgaga cagagtcttg 88620 ctctgtcacc caggctagag tgcagtggca tgatctcggc tcactgaaac atttgcctcc 88680
tgggttcgaa caactctcct gcctcagcct cctgcgtagc tgggattaca gatgcctgcc 88740
accatgcccg gctaattttt gtattttgat atatatatat aatttttttt ttctttttttt 88800 ttttttttag tagagacggg atttcaccat gttggccagg ctggtctcaa acccctgacg 88860
ttgtgatccc cccgaccttg gcctcccaca gtgctgggat tacaggtgtg agccaccgcg 88920
cccagcctac agtttacttt tgaatttcat agttatgaag ttttcagggc agagatttat 88980
tatctctgaa ttggtaatga agaaaaacca tagagacggg gtttcaccat gttggccagg 89040
ctggtctcaa acccctgacc ttgtgatccc cctgaccttg gcctcccaca gtgctgggat 89100
tacaggtgtg agccaccgcg cccagcctac agtttacttt tgaatttcat agttatgaag 89160
ttttcagggc agagatttat tatctctgaa ttggtaatga agaaaaaact caatgattaa 89220
ttaaactcag atagattaaa ttacttttgt aacttctctc acctcattgc agaatcaggc 89280
tcagtcctag gtcttagagg tctttagtta gctgtacatt gcttccccat ccatttttat 89340
tcgggcatat tctgttaaga tgatatcaat tcttgccggt gacatggttt actgaatcct 89400
agcattaagc aaataaaaat gactttgttc ctttgaaagg catagccaaa tgtgattcaa 89460
gaagccaatc tgggaaacaa tttccaaaca gttcatgaga ttgcccaact ttcagcaaaa 89520
taaaagggtt tatttctggc atcctcgtgg tgtaaataat ttcttaatta tgcaaaaaat 89580
tgctttcttg ggtttgatat atgcatttat aggccgagtt ttttactcaa aggattaagg 89640
tatttatcca tctcaatctg ggaatatcca aaatactcat taaacagttc tttgtaaatg 89700
cctgatgcca caggccccat tctgataata tcatatttct ctatacctca cacttaggct 89760

```
agacaagaac tgtaatgagg gataataatt gaccagatga cattttacaa aagattcaag  89820
tttcttcttc ttcattcctt ttttttaatt gagtccagta aaccgtatgc gaagcactgt  89880
gttaaatacc ttgatctacc ttatctcagt ggtcctcgac tgaatcgcct tgtgtaactt  89940
attaaaaata tgttttcctg gatgccagct tgtgttggaa gggagccagg aaaatgcatt  90000
tttataagtt tcacaagtga ttctgatgtt tatttctggt taactactat agccttatcc  90060
catttcttcc tcataaaaat cttgagaagt ctcagtaatt gtaaaagaag ataaattgga  90120
agaacaaaaa tagcttttca ggcactctat tctgtctata ctatgatcat gaaggtataa  90180
ggagtgtgtt tctgaattca attgatttga atagatgaag tcctaggcct tcattttttc  90240
ttttctctgg ttcctctctg cagtctcctt tcagcctgct tcaggaatga gcttgtggag  90300
ccccggagag aaactccaaa acaatctgac gtcttcttta gacattccaa gcccccaaac  90360
cgatcagtgt acccatagag ccctatctct atattttaag tgtgtgtgtt gtatttccat  90420
gtgtatatgt gagtgtgtgt gtgtgtatgt gtgtgcgtgt gtatctagcc ctcataaaca  90480
ggacttgaag acactttggc tcagagaccc aactgctcaa aggcacaaag ccactagtga  90540
gagaatcttt tgaagggact caaaccttta caagaaagga tgttttctgc agattttgta  90600
tccttagacc ggccattggt gggtgaggaa ccactgtgtt tgtctgtgag ctttctgttg  90660
tttcctggga gggaggggtc aggtggggaa aggggcatta agatgtttat tggaaccctt  90720
ttctgtcttc ttctgttgtt tttctaaaat tcacagggaa gcttttgagc aggtctcaaa  90780
cttaagatgt ctttttaaga aaaggagaaa aaagttgtta ttgtctgtgc ataagtaagt  90840
tgtaggtgac tgagagactc agtcagaccc ttttaatgct ggtcatgtaa taatattgca  90900
agtagtaaga aacgaaggtg tcaagtgtac tgctgggcag cgaggtgatc attaccaaaa  90960
gtaatcaact ttgtgggtgg agagttcttt gtgagaactt gcattatttg tgtcctcccc  91020
tcatgtgtag gtagaacatt tcttaatgct gtgtacctgc ctctgccact gtatgttggc  91080
atctgttatg ctaaagtttt tcttgtacat gaaaccctgg aagacctact acaaaaaaac  91140
tgttgtttgg cccccatagc aggtgaactc attttgtgct tttaatagaa agacaaatcc  91200
accccagtaa tattgccctt acgtagttgt ttaccattat tcaaagctca aaatagaatt  91260
tgaagccctc tcacaaaatc tgtgattaat ttgcttaatt agagcttcta tccctcaagc  91320
ctacctacca taaaaccagc catattactg atactgttca gtgcatttag ccaggagact  91380
tacgttttga gtaagtgaga tccaagcaga cgtgttaaaa tcagcactcc tggactggaa  91440
attaaagatt gaaagggtag actacttttc tttttttac tcaaaagttt agagaatctc  91500
tgtttctttc cattttaaaa acatatttta agataatagc ataaagactt taaaaatgtt  91560
cctcccctcc atcttcccac acccagtcac cagcactgta ttttctgtca ccaagacaat  91620
gatttcttgt tattgaggct gttgcttttg tggatgtgtg attttaattt tcaataaact  91680
tttgcatctt ggtttatctt gcagtttttt tgtttctgtc tctctcactt tttttccact  91740
aaatactaga atattctcat gtaagtgctt gaagtagcat gtgtaggtct aaggaacaag  91800
aataataata gaatcatcac tttgttccta cgtacatttc ttctgtcagt atttggtatt  91860
tttatttaag atactctgta tcaaggtcat caatcgtaac aaggaactaa aatgcctaaa  91920
ctaacttaaa aaaatacttt agctctatga gttttaaagt ttgtcctagg aagccagaca  91980
ccatagaatc atttattgac attcctgaca aacctctagt tgtatgttaa ttcgccaaat  92040
ttactaaagt gaatttcaat caaatccaaa tgttttaaat aacatggctt ctgtggcata  92100
gacattagca aatatttggc cagaaatcaa cagtggaacc tattgtccaa tttttttttt  92160
```

tacttatgtt ttgagccctg aataattgct tttaaaagct tcataagaag ttctaaccaa 92220
aaaaaaaaaa ttagtatttt agataaatat ttcagaaaaa aaaatcttta tatttgagat 92280
aaaagtatat tagtaaaacc agatgctcct gttatatttg caaggtgttt ttcaattggt 92340
ctaataactt tgattcacaa agcccttaaa ggattggtga gtatgtttcg ttttttgata 92400
tttgcttttc tttcagaagg gtttttcttt tctttcagcc ttttttaagt aagtttttaa 92460
tgtgtttata gtgacttgta tataaatgca catatttgaa atgatggaaa atattagaaa 92520
attacagttt tcccatctag agaataaatg ctgcactgtc tttagtagcc agataacccg 92580
gctagagaga aaggtcacag gtaggcagta ctgggtaaaa ttgagagaag atatgattct 92640
ttttctgatg gtccatgttt tccctttttt tttttttttt cctgaccttt ctcataacaa 92700
ggatgctctg ctccgccctc agtatccctt tctgctccca aattctttac tgcagaaatg 92760
gtttgttgaa atagatttgg cctaagctat caccaaatcc tactagaggg ttgcttttta 92820
atgagcagtg gaagatttta gccaaaagaa ggaatctagt ggaattctag acatctagga 92880
ggtagatagt gtaacttgtg tctgcgcagg aattttgata ttctaccaca tagatagtca 92940
ctagggttgg aaccagaaaa cctgatttga agtcctatat gtcctaaaac cacttctcgc 93000
ttttcaattt tgaattttat tcttcggaaa ctgtgcagaa gcttatattg ttaaagttaa 93060
gaactgggac ttggctccac caggattttt cttcaaagct ggaaatacgt gaaatatgat 93120
tttctacatc tctgttacac tgaattctta gaaaaatcta gtgaggctct agagaaaaca 93180
acctgaggta tacaccttac gatttttttc tgcagacagc tggattctta ctttttttggg 93240 ttttggatag gagaggagag tgtaggcaag aaaaccagaa tggtacaggt cctgttattc 93300
ttctgaacac attttccttc tctttagttt ctccagaaat ttttggaata tttcacttaa 93360
gaactattgt attaaatttg taattttttt taaaaaaggt tgttcttcaa ggctttcaaa 93420
ttggctgagt ttattcagcc ttgcttcctt tttcaccgta tgtagttttc agaatgcttc 93480
ttctagttca gtcattttga aattaataat agacagacta ccttgcttcc cttccgtgtg 93540
gctttaaaac tcactttcat attaaaggga aggcattccg aatttctgac ctttcctgac 93600
tgttaacccc attcaactgt tcaccctcat ttctgggtat gttcaattaa gaatccaact 93660
cacctctggc cacttcctcc tattaattct tacatagtta tcttctatgc catgggccac 93720
atatcagagt gttaaatatt tgaggctgga gggaaacagt gaaagaagct aagaagctga 93780
tgtttcctga gcacctacaa atcactggac cctgtccagg gctgttacat gatctcattc 93840
ttaatagaaa tcttctagag taggtacaat atctaggcta caggttaaga aaatgagact 93900
caagaaactt gtacaacatc ctgcgtcact aagtttgtgt tagatgtttt gattgactta 93960
gaatccatgt tccttctttc ttcatctgtg gtttctgacc taccctcctc aaattagtgg 94020
cttatgatga aaaatggtaa atgaactaat aaaatagtca aaaataataa ccataagcta 94080
aagaaagcag gaggttgtaa caggaattgt aagaaggaat ttactctgag cgtccagaaa 94140
aaaaaaaaag caaaactttt aaatgtattt ttatttttct aattgtggct attaatgatt 94200
caagcactgc tttctattag ctcttgctgt acatttgact ggtttgagga gggacagata 94260
gagaggtctc ctcaggttac agaggaccaa ctgcatcagg aatatgggct acctggaatc 94320
ttaggtactt ttcagtgagc aaagagaatt gaagaaacat cagctggcag agaatctcct 94380
tactgccttg ccccaagctt tcctatactc tgatgtggac taatggatga gcctaagtgc 94440
agccatatgt gctgactctt tgaaaaggtt cccccacagg gacggagtgg attcagaagt 94500
gcttggtagt agctggagtt acctccttta cccctcttcc atcttggtct cctacatttc 94560

```
tcttactact tcatctattt cttgtcccca taacctagaa aaaacaatag gtgccaggag  94620
acctagttct gccctcagtg catccattta gcaacatgtg atcttgggca tatgtttttt  94680
cttagaacct tatatttacc catatgtata tttggaatag taatttctgt ccatctctgc  94740
cctgctatac catgacctgc tccacaagga tggtgtgaca atcattcaga aaatgtacaa  94800
agaagagttc ggtaacctga aatgttttat agttgggagg atttattgta tcaacaccag  94860
tatatatata caatgtggat ctataattgt gagtatttga taagggctaa agagaaaagt  94920
caatgccctc ctaccttaaa ggcagtgatt gtaaaataca cctgaattgt taatttacat  94980
taattgacat gataatttat acacattaaa atacagcata ttgtttgcat tcatctagct  95040
gtggctctcc attgacatgg aatggagcct tccttatttt catgtaatta tggagagaat  95100
gcagagtggc agcttcgaag accatcccta cgattgcagc acctaagtgc tagggccatt  95160
tttaaaatga ttttttcaa atattatgcc atataggctt ggaacctggg tccatttaca  95220
gagcctccaa aatttgaatt atacatatat atgcagataa aactcaaaga aaaaatttgt  95280
ctcccctcta atgtaaatat gcctgtgaca gggaaaaggt aaacaggaac aacataattc  95340
gctttgtttg agaattgtta aaggggagtt ttcccataac agactagaca cttgcttaaa  95400
gtccagtctt cattctgtgg tcacagtaat tcagtgtaga tgctgcatag tctgtacatt  95460
tcttcctcat cttctctttt tcagttctca tcatagccgt ataaggtagg atggattatt  95520
atatccattg cctccactac tctatgagtg tctcaaagat ggggaccatg ccttaagttt  95580
tattaacttg aacatctgac tcatgcagca agtgtaaatg tatgtagttt atatagtttt  95640
cttgtgagaa aacaaaggcc aggatgttaa gtagctcgca tgggcatcta tagcatccta  95700
acagatgacg gaggaaggct tcatctctga ctttgtgact ctcattgtag tacacatcac  95760
tagtttttat attaagataa aacatcagga atgacagttg agttgggaat attatctgtt  95820
agatataata tgacaaatga gttctggtaa ctttccaaat tgaagatcat gctgaatgga  95880
aaactattgg gtttttctgt tgctttgttt ttttcatttc tcccaggaga cttttggaaa  95940
gtcaatagaa tagttatttg ggcttcagcg ttctcctgtg tagaaatgct tttgacattc  96000
cagtaggttc tctcatacat catgaacatc tctattgaaa atgcatgttt ccaagtaggg  96060
gcctctgcat gacagcaaga tgagctgcca aatgcccagt ttgattgggt ttgtagtcat  96120
tttctgcata tcccaaatgg aatatacaga aagctacaaa tggaatgcct tagctgcagt  96180
ttgagggtgg gatatccatg tttttcgtca gcctttaagt ctttgctcaa ttcttttccc  96240
taactgcttt tcaaactcat ttgagttgaa gggaaaagag gagaagggaa tggagaaaac  96300
aactgaaggg aaaagaggag gcaagaattt tctctttctc aaaggaaata ctaaaccttg  96360
cactctgcac attcaggaaa aatatgattt gatgatagcc tcgcagtcag tttctcccta  96420
ttcaggaaat attctcagat ggaaacaaaa ttaacttctt accattaatc ctagaagaat  96480
gttttcaaat gtttggtttg aggccatgtt ttaaacagag acctgttgaa aatcaatagt  96540
ccccactctt cagtgtccct tgctcaccat tatttccatg tttgtcttcc taggacctca  96600
atacagtctc catcttcata tggtaacagc tccccacctc tgaacaaaat gaacagcatg  96660
aacaagctgc cttctgtgag ccagcttatc aaccctcagc agcgcaacgc cctcactcct  96720
acaaccattc ctgatggcat gggagccaac agtaagagca tctcctttta gctgtggctg  96780
aaggatgaac aggctagctt aggacaagac tctgtgatgg ggaaggcatg ttcttaagct  96840
aaatgagaga cacagtggga cagatcagat caaagtggag tggcttgggt ttctgactga  96900
acctttcact tttgaggttt atcattcatt gcaaaatata ctactggtag agatagggac  96960
```

ggatgtttct ttagtgtagg gataaggatt tctgtgaaaa gaacagtcta cttgctgcta 97020
tcctggatgg agactcacca cctgcagcct ttgaaatagt caaaaggaaa caaatgcaac 97080
atgcataaag tagcatgttg cagtgaactt aaaatctaga gaaataggcc gggcatggtg 97140
gctcacgact gcaatcctag cactttggga ggccgaggcg ggaggatcac ttgaggtcag 97200
gagttcgaga ccaacctggc caacatggtg aaaccccgtc tctattaaaa atacaaaagt 97260
tagctgagcc tggtggtgca tgcctgtaat cccagctact caggaggctg aggcatgaaa 97320
atcacttgaa cccgggaggc agaggttgca gtaaggtgag atcacactgc tgcactccag 97380
cctgggtgac agagtgagac tcagtctcaa aaaaaaaaaa aaaaatctag aaaagtagat 97440
tatcgtctgg actctatgaa aaaaatacct ctaattacaa agaagttact tctcgaatac 97500
ttaattttct atccataaaa ttgtcactat atatacttaa cattttatgt ctgttactct 97560
ataatcctgg ccttttaaac tcacctattc tatcccagac acagtcagta aggaactgat 97620
ctacgaagga acctgccttt tatttcttct cacacacatt cctcatatca gctaagtaca 97680
aatgaaaaag gcactgtaag aattgggcct ccaagtggat gatgactggc atatagcttt 97740
actataaata taattatctt ctccactagg actaaatcta gcaaagtgga tacacaaact 97800
tgaaggaaaa aaaagtcgtg gtaaaaatgc aaaagattgt ataacaccct cggggataca 97860
gaagactgaa cattgcatgg gtatcatata atccttacta cctaaaaaac agtaccctca 97920
agcttgtctt ttgaaatcct aattattttg atcaaacctc taaacgagca tttcagtgtt 97980
gtctcttctg aaagaaatca ggggaggcta ggattatgac tttctgtggt ctaatggcac 98040
acattcattg ttttggtttt tttttttttt ttttagacag agtttcgctc ttgttgccca 98100
ggctggagtg caatggcgca atctcggctc actgtaatct ctgcctccca ggttcaagtg 98160
attctcctgc ctcagcctcc cgaatagctg ggattacagg cgtgcaccac cacgcccggc 98220
taattttttg tatttttagt agaggtgggt tttcaccatg ttggccagac tggtcgcgaa 98280
ctcctgacct caggtgatcc acccacctca gcctcccaaa gtgctgggat tacaggcgtg 98340
agccaccgcg cctggccaca cattcatatt ttaatgagat agaggtgtgt gtgtttgcaa 98400
tggttgcctg ttatggcaaa cgtagacttt agagtgagat cactctctca ctaatgataa 98460
actcatcata aggcttaaaa cctgacccct tgacaggcct actttgacat aaaaagagta 98520
gaaaccattt attttcaact ttattttatt tcttgtgaca tcttagagtc ctcaagttcc 98580
ttcttggtat gacaaaattg tgataatagt gatgatggtt cacatttgta taacttacag 98640
tttgcctact ttttttctta tttgtacttt acaattattt cagaaggaaa acagattgag 98700
atgtgatagg gtatgctctt tagttagcta gttagtggca aagacctttt ctaggcatac 98760
tgctactcac taaagtagaa acaaattaca ttaatctttt agtaaattat tttgttcttt 98820
ttgacatgaa ggcaaaattc attttataaa tattgatatt aaactttttt tctctatcag 98880
tgagtgttta cacttaattg tttagtaaaa tatcagtaag tattggtggt gttcctgtat 98940
acaaccctga aaatggacca taagtaatag aatatttaat tgtatcatca tttattaggc 99000
acgtgagtcc ttctaaatat tgaagtcagt ctccctattc ccaaataaat gttccaaggg 99060
tcactctttc attcacagat ttgtgcattt atccacttac cctaagttta ctgagcacct 99120
actctgtgcc aggcactgtg ctagggactg tagggatcta gacacctata agatctaatc 99180
tctgtgcttg cacaggttag tgagggagac agaaatatca ccctcgaagg caaatacaag 99240
gaagaatatg ttaacattaa gagcaattag caattagaga attagaagca gagaaagggg 99300
aggaaagaga ttgttctcgg acaaggtaca aaagtcaaga ggtgcctaat tagtttggag 99360
tctgaccgtt ctgtttgact agatgtaggc tgtttgaagg ggtgtagtga gagcgaagat 99420
taaaaaggaa ggctggtagt ttaggccctt gataaaattt aaccagacaa gatggaccac 99480
tgggatgctg gtacatgatg atggcagtaa cccttttttgt tcctcctgct tctgttcagt 99540
tcccatgatg ggcacccaca tgccaatggc tggagacatg aatggactca gccccaccca 99600
ggcactccct cccccactct ccatgccatc cacctcccac tgcacacccc cacctccgta 99660
tcccacagat tgcagcattg tcaggtgagt ccacagcatg tgcccctggg ggcctgccct 99720
aagcatcccg ggatggtgga gggcggatac tgttatagtc cataaaacag ttggaaggga 99780
agacagcagt cctgtggttg gagttcagtc actattatct ctgatctgtg gagtggtcaa 99840
caatgtttta tcaaggaaaa ctactataac cagcatggaa acaagggaaa gtgtctgttg 99900
ataggcatat tgttttcatg tctgtttccc tcgccttcac ttactccctt cctcctctct 99960
cacattttta cattgtcaat tgcggccctc aagttggtgc tcagggctgg gtttccaaaa 100020
gggcaataaa cttgctatct cgctcctttt cctctctctc taatccttat agctctcagc 100080
caccatggga ccattatttt ggagttggat gtccataaaa agttttaatg ttatccaaaa 100140
tgacagggac tttcaaaaac tgatggcctt tactactctg cctatgggaa atgggcacac 100200
tccagaaaag gggagttgag ataagcagaa gaaagaaatg catgaagcct gaaagatttg 100260
cttcccacag aggcaagagt aggttcccag atttcttgcc tagtgtatat cttcttcttc 100320
tgcttcatgt gcagaatgat tgtttcattt ggctactgga acgatttgtg ttgattttcc 100380
tgctacgtca atcacaggga tggcaaagtg cgtggccttt tccacccagg gtctgttctg 100440
taatgatggt ggcatcatca tcagtctcag accagcacca aaaggaaggg gatctgtatc 100500
ctgagaagga cataaatcaa aaggcatgaa tgacttaatg gagtagaggc ctacaatttt 100560
tttcttaacc acatgagcca ttctcacaaa gcccagatac aaaacaaata aagtagagat 100620
gttctttttg aagtgtagag ccaagcagca agaaagctag gaacctgaac actggacttc 100680
cctttcaccc tttgcaatgg ttcctaggac acttacacag aaccctagaa ttccacagat 100740
caccatatga taatcgctga tctgcaggaa tccttatagt tgattttaat ttctgtagac 100800
ctaaacttca tgtcaccagt aatctccaga cctcagactt aaggcccaca tatatattac 100860
ccaatcctca tctctgatgt ggggcatcca agggcaaaat atattgggtt ttcccttatc 100920
tcgccaatgc agttggggtg aactttcttt ttctgtttcc tccttcctct tccctcctcc 100980
ctctgcagtt tcttagcgag gttgggctgt tcatcatgtc tggactattt cacgacccag 101040
gggctgacca ccatctatca gattgagcat tactccatgg atgtaagtaa ctgttagact 101100
tttctcaaat tttatttctt catttctttc ctctgatgac aaccgccttg tagttcaatc 101160
cctgatagtt taaaaatttg tttttgtcat gcccccaatt atccattttg atagaaccca 101220
taactatgtt agaaagattc ccaggcctca acctatacat attagaagct tagcaatcaa 101280
tcttccttag cttgtcttat cagtcaacaa ttgtctattg cacttacact attctcaagg 101340
tgggaaagag gagctattcc cgcaatcaaa acattcataa tttctaaaga attaatacaa 101400
ctttttgagt gtgctcatta atctgtatca gttcccagaa aggatagcag ggcaccggtg 101460
gtgctattct cttaaaaaca tggagagatg acacagtagt catttgccat gactatttaa 101520
aacaaaacta ggaatagaac acaaacgtgt aagcttacag tctttaactt tattaactgg 101580
ccttttctgc ctttctttaa attagtacct taagggagat tcagccgttc ctctcaatta 101640
aaactatatg ttcctttatt aattttcagt ttcatcctaa tagagcccag ccatttctaa 101700
tcattgggca ttatcaatgg ctatggggtc aaatcccaat caccctttt agtagcaatg 101760 agaacttggg gttatcactt tgcctctctg ggcctcagtt aataaaatat tgggttcaaa 101820
ttactccttt ctggctttca tatcctttga tttgtctttg aaacaagctg ggcgagaggg 101880
gactttttct tgcttcctac tccacttttt gaactcctgc tcacacggga gctagtgttg 101940
ctctggttta tggcaatctg atttgtctct taggccgcgc tcttcatgct gctctctttg 102000
gggttcacta gcctctcttc tagcttccag agggtacttt ggactgcggg aagaagacag 102060
tctctgcctc tgctgctact tctattgttg gggactcttt tttccccctc cttgagcacc 102120
gatgctagag atgcccctgc agcataagaa tgcccccacc atgaggtgac gtgtacatag 102180
tgtactgccc ctatgcccac ccctcttcac cccataaatc actcctggct gctgctccct 102240
gatagaataa gttataagca aaaactgcag ggaaagcttt aagagtaagt tccagtatta 102300
ttctgataac tttacagtca cttccgtcca ctgaagagaa cagagttgcc ctatatttga 102360
gagagtctcc tgtagtagat tcctacattt tggaacagag aatcttcctc ttccctatat 102420
ttttaaagtt atactttcca cttgctcact tatttccact ggggaatgtg tcaggatgtt 102480
cccttgatca ttaggatctg cagataccct ttataagttc atttctgctg atgttgacta 102540
agtcctatgc caatctgtgg gccacagctt tctcacctgt cagtcattag ttaaaatcca 102600
tccagggcat catgacaatg aacagagtct aatttacaaa gagctttgca tttactgaga 102660
gcctcaaaag tataaagaat ccaagaaaca taaaaagcta tgcttattta ggccgggcat 102720
ggtggctcac acctgtaatc ccagcacttt gggaggccga ggcaggcgga tcacgaggtc 102780
aggagaccga gaccatcctg gctaacacgg tgaaaccctg tctctactaa aaatacaaaa 102840
aattagccag gtgtggtggt gcacctctgt agtcccagct actcaggagg ccgaggcagg 102900
aaaatggcgt gaacttggga ggcggagttt gcagtgagcc gagatcacgc cactgcactc 102960
cagcctgggt gaaagtgcaa gactccgtct caaaaaaataa taaaaaaagc tatgcttatt 103020
tttttgtgga ttaccttctt tataaggtat tcttctgcta cagtaagaga ttaggaatac 103080
ctctaatggc ctgaaaattc acaccatagg aaaatatgac accagactac aaacttccaa 103140
attgagaaat gttgggaagc tgtgcaattt tctcctcctc acctcagctt cttcctgcgt 103200
atttctagaa agagacaccc ttttctcagc ttttatctta gagccagtct aagttattgg 103260
gcatcatcac ttcctggaaa aggaatgtga cctaaatttg gggaacttca ttagtatccc 103320
cataacatgc aaaaatgagg taacaataca acataataat aatacaaatg gttaatattt 103380
atagagtgtg ttgtaattta taaaatactt tcatagctgt atttacctat gagtctatag 103440
catcttttgc cctataaagc aattgtatct cattttacca aagaagaaac tgaggctggt 103500
agagaataag tgacttgctg aagttctata gccagtcagt gaccatcaaa acctctgcca 103560
cagttttctc actccaagca caatgtgctg tttacctacc attctgccct gtgaaaatat 103620
gagctatcac tgaaacaatc taaagaagag ctaacgcaga taaatgtaag tgatatcacc 103680
acagtcagtt aaggttgacc ctatttgcaa tgccttctgc acccattcac agaacataga 103740
cacagttgct ctgcattttg ataccttgct ttattcaaac accaagagac cttttagata 103800
aaagtgccgt ttcaggttct gaggatgccc taagtcccta attttttcac ttagttatgt 103860
gactttaaac ttgtcaacct ctctggcctt cagttgttct atctataaaa caggtctaat 103920
aatgtttacc actaatctgg ggattaaatg atatcatgaa tataaaataa ttcagggcct 103980
ggcacataga aagtactcaa tcttttcttc tcatctcctc aaccaagtgg tggtgacatt 104040
ccattaatac ctttcttcta gtgactagcc aggtaaattc aagcataagt aggtacctca 104100
tgtttctatt tgggattttt gccctctcat ctagctatta tcccaatttt accaatgaag 104160
aaactgaggc cagtagagac taagtgaagt gttctacaca ggcaggaaag acacctcaag 104220
gctgtgcctt tgtgcttagt tccatagagt tgaagactca gagaactaat tttattttct 104280
aatttgtgga tcaatagatt cagatcaatt aaaccagagc atcagggaat gataggatgc 104340
tgtggactaa atgtccgttt ttctccctgt tttcattctc catgacacct tcccctgttg 104400
cacaggatct ggcaagtctg aaaatccctg agcaatttcg acatgcgatc tggaagggca 104460
tcctggacca ccggcagctc cacgaattct cctccccttc tcatctcctg cggaccccaa 104520
gcagtgcctc tacagtcagt gtgggctcca gtgagacccg gggtgagcgt gttattgatg 104580
ctgtgcgatt caccctccgc cagaccatct ctttcccacc ccgagatgag tggaatgact 104640
tcaactttga catggatgct cgccgcaata agcaacagcg catcaaagag gagggggagt 104700
gagcctcacc atgtgagctc ttcctatccc tctcctaact gccagccccc taaaagcact 104760
cctgcttaat cttcaaagcc ttctccctag ctcctcccct tcctcttgtc tgatttctta 104820
ggggaaggag aagtaagagg ctacctctta cctaacatct gacctggcat ctaattctga 104880
ttctggcttt aagccttcaa aactatagct tgcagaactg tagctgccat ggctaggtag 104940
aagtgagcaa aaaagagttg ggtgtctcct taagctgcag agatttctca ttgactttta 105000
taaagcatgt tcacccttat agtctaagac tatatatata aatgtataaa tatacagtat 105060
agatttttgg gtggggggca ttgagtattg tttaaaatgt aatttaaatg aaagaaaatt 105120
gagttgcact tattgaccat tttttaattt acttgttttg gatggcttgt ctatactcct 105180
tcccttaagg ggtatcatgt atggtgatag gtatctagag cttaatgcta catgtgagtg 105240
acgatgatgt acagattctt tcagttcttt ggattctaaa tacatgccac atcaaacctt 105300
tgagtagatc catttccatt gcttattatg taggtaagac tgtagatatg tattcttttc 105360
tcagtgttgg tatattttat attactgaca tttcttctag tgatgatggt tcacgttggg 105420
gtgatttaat ccagttataa gaagaagttc atgtccaaac gtcctcttta gtttttggtt 105480
gggaatgagg aaaattctta aaaggcccat agcagccagt tcaaaaacac ccgacgtcat 105540
gtatttgagc atatcagtaa ccccccttaaa tttaatacca gataccttat cttacaatat 105600
tgattgggaa aacatttgct gccattacag aggtattaaa actaaatttc actactagat 105660
tgactaactc aaatacacat ttgctactgt tgtaagaatt ctgattgatt tgattgggat 105720
gaatgccatc tatctagttc taacagtgaa gttttactgt ctattaatat tcagggtaaa 105780
taggaatcat tcagaaatgt tgagtctgta ctaaacagta agatatctca atgaaccata 105840
aattcaactt tgtaaaaatc ttttgaagca tagataatat tgtttggtaa atgtttcttt 105900
tgtttggtaa atgtttcttt taaagaccct cctattctat aaaactctgc atgtagaggc 105960
ttgtttacct ttctctctct aaggtttaca ataggagtgg tgatttgaaa aatataaaat 106020
tatgagattg gttttcctgt ggcataaatt gcatcactgt atcattttct tttttaaccg 106080
gtaagagttt cagtttgttg gaaagtaact gtgagaaccc agtttcccgt ccatctccct 106140
tagggactac ccatagacat gaaaggtccc cacagagcaa gagataagtc tttcatggct 106200
gctgttgctt aaaccactta aacgaagagt tcccttgaaa ctttgggaaa acatgttaat 106260
gacaatattc cagatctttc agaaatataa cacatttttt tgcatgcatg caaatgagct 106320
ctgaaatctt cccatgcatt ctggtcaagg gctgtcattg cacataagct tccattttaa 106380
ttttaaagtg caaaagggcc agcgtggctc taaaaggtaa tgtgtggatt gcctctgaaa 106440
agtgtgtata tattttgtgt gaaattgcat actttgtatt ttgattattt ttttttctt 106500 cttgggatag tgggatttcc agaaccacac ttgaaacctt tttttatcgt ttttgtattt 106560

```
tcatgaaaat accatttagt aagaatacca catcaaataa gaaataatgc tacaatttta 106620
agaggggagg gaagggaaag ttttttttta ttattttttt aaaattttgt atgttaaaga 106680
gaatgagtcc ttgatttcaa agttttgttg tacttaaatg gtaataagca ctgtaaactt 106740
ctgcaacaag catgcagctt tgcaaaccca ttaaggggaa gaatgaaagc tgttccttgg 106800
tcctagtaag aagacaaact gcttccctta ctttgctgag ggtttgaata aacctaggac 106860
ttccgagcta tgtcagtact attcaggtaa cactagggcc ttggaaattc ctgtactgtg 106920
tctcatggat ttggcactag ccaaagcgag gcacccttac tggcttacct cctcatggca 106980
gcctactctc cttgagtgta tgagtagcca gggtaagggg taaaaggata gtaagcatag 107040
aaaccactag aaagtgggct taatggagtt cttgtggcct cagctcaatg cagttagctg 107100
aagaattgaa aagtttttgt ttggagacgt ttataaacag aaatggaaag cagagttttc 107160
attaaatcct tttacctttt tttttcttg gtaatcccct aaaataacag tatgtgggat 107220
attgaatgtt aaagggatat ttttttctat tatttttata attgtacaaa attaagcaaa 107280
tgttaaaagt tttatatgct ttattaatgt tttcaaaagg tattatacat gtgatacatt 107340
ttttaagctt cagttgcttg tcttctggta ctttctgtta tgggcttttg gggagccaga 107400
agccaatcta caatctcttt ttgtttgcca ggacatgcaa taaaatttaa aaaataaata 107460
aaaact                                                            107466
```

```
<210> SEQ ID NO 2
<211> LENGTH: 586
<212> TYPE: PRT
<213> ORGANISM: Homo sapiens

<400> SEQUENCE: 2

Met Leu Tyr Leu Glu Asn Asn Ala Gln Thr Gln Phe Ser Glu Pro Gln
1               5                   10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205
```

-continued

```
Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
        275                 280                 285

His Gly Ile Gln Met Thr Ser Ile Lys Lys Arg Arg Ser Pro Asp Asp
    290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln Gln His Gln His Leu
            340                 345                 350

Leu Gln Lys Gln Thr Ser Ile Gln Ser Pro Ser Ser Tyr Gly Asn Ser
        355                 360                 365

Ser Pro Pro Leu Asn Lys Met Asn Ser Met Asn Lys Leu Pro Ser Val
    370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
        435                 440                 445

Tyr Pro Thr Asp Cys Ser Ile Val Ser Phe Leu Ala Arg Leu Gly Cys
    450                 455                 460

Ser Ser Cys Leu Asp Tyr Phe Thr Thr Gln Gly Leu Thr Thr Ile Tyr
465                 470                 475                 480

Gln Ile Glu His Tyr Ser Met Asp Asp Leu Ala Ser Leu Lys Ile Pro
                485                 490                 495

Glu Gln Phe Arg His Ala Ile Trp Lys Gly Ile Leu Asp His Arg Gln
            500                 505                 510

Leu His Glu Phe Ser Ser Pro Ser His Leu Leu Arg Thr Pro Ser Ser
        515                 520                 525

Ala Ser Thr Val Ser Val Gly Ser Ser Glu Thr Arg Gly Glu Arg Val
    530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Glu Gly Glu
            580                 585
```

<210> SEQ ID NO 3
<211> LENGTH: 1761
<212> TYPE: DNA
<213> ORGANISM: Homo sapiens

<400> SEQUENCE: 3

-continued

```
atgttgtacc tggaaaacaa tgcccagact caatttagtg agccacagta cacgaacctg     60
gggctcctga acagcatgga ccagcagatt cagaacggct cctcgtccac cagtccctat    120
aacacagacc acgcgcagaa cagcgtcacg gcgccctcgc cctacgcaca gcccagctcc    180
accttcgatg ctctctctcc atcacccgcc atcccctcca acaccgacta cccaggcccg    240
cacagtttcg acgtgtcctt ccagcagtcg agcaccgcca agtcggccac ctggacgtat    300
tccactgaac tgaagaaact ctactgccaa attgcaaaga catgccccat ccagatcaag    360
gtgatgaccc cacctcctca gggagctgtt atccgcgcca tgcctgtcta caaaaaagct    420
gagcacgtca cggaggtggt gaagcggtgc ccaaccatg agctgagccg tgaattcaac     480
gagggacaga ttgcccctcc tagtcatttg attcgagtag aggggaacag ccatgcccag    540
tatgtagaag atcccatcac aggaagacag agtgtgctgg taccttatga gccaccccag    600
gttggcactg aattcacgac agtcttgtac aatttcatgt gtaacagcag ttgtgttgga    660
gggatgaacc gccgtccaat tttaatcatt gttactctgg aaaccagaga tgggcaagtc    720
ctgggccgac gctgctttga ggcccggatc tgtgcttgcc caggaagaga caggaaggcg    780
gatgaagata gcatcagaaa gcagcaagtt tcggacagta caaagaacgg tgatggtacg    840
aagcgcccgt ttcgtcagaa cacacatggt atccagatga catccatcaa gaaacgaaga    900
tccccagatg atgaactgtt atacttacca gtgaggggcc gtgagactta tgaaatgctg    960
ttgaagatca aagagtccct ggaactcatg cagtaccttc ctcagcacac aattgaaacg   1020
tacaggcaac agcaacagca gcagcaccag cacttacttc agaaacagac ctcaatacag   1080
tctccatctt catatggtaa cagctcccca cctctgaaca aaatgaacag catgaacaag   1140
ctgccttctg tgagccagct tatcaaccct cagcagcgca acgccctcac tcctacaacc   1200
attcctgatg gcatgggagc caacattccc atgatgggca cccacatgcc aatggctgga   1260
gacatgaatg gactcagccc cacccaggca ctccctcccc cactctccat gccatccacc   1320
tcccactgca cacccccacc tccgtatccc acagattgca gcattgtcag tttcttagcg   1380
aggttgggct gttcatcatg tctggactat ttcacgaccc aggggctgac caccatctat   1440
cagattgagc attactccat ggatgatctg gcaagtctga aaatccctga gcaatttcga   1500
catgcgatct ggaagggcat cctggaccac cggcagctcc acgaattctc ctccccttct   1560
catctcctgc ggaccccaag cagtgcctct acagtcagtg tgggctccag tgagacccgg   1620
ggtgagcgtg ttattgatgc tgtgcgattc accctccgcc agaccatctc tttcccaccc   1680
cgagatgagt ggaatgactt caactttgac atggatgctc gccgcaataa gcaacagcgc   1740
atcaaagagg agggggagtg a                                              1761
```

DNP63A GENE AND SCREENING METHODS OF ANTICANCER AGENT BY USING IT

CROSS-REFERENCE TO RELATED APPLICATIONS

This application claims priority under 35 U.S.C. §371 from international application PCT/KR2007/001576, filed Mar. 30, 2007.

TECHNICAL FIELD

The function of ΔNp63α which is specifically expressed in the epidermal stem cells and cancer cells and repressed during differentiation could be very important in the point of that about 80% of human cancer is derived from epithelial cell and cancer could be derived by genetic aberration from stem cell. Also as ΔNp63α has a function to inhibit p53 in cell proliferation and death and works as a carcinogenesis control gene when it is over-expressed, the quantitative balance between p53 and ΔNp63α in stem cell is regarded to control cellular proliferation and differentiation. Therefore, ΔNp63α's stability in protein level and its location in cell are thought to exert important function in the carcinogenesis.

p63 gene, located on chromosome 3q, encodes a nuclear protein with high sequence similarity with p53. p53 protein is a tumor-suppressor, having a transcription activation domain which is important in the regulation of cell cycle and cell death. Protein p63 exists in two different forms, each produced from distict transcripts by two selective promoters. The first transcript is translated to full-length proteins including N-terminal transcription activation domain like p53. It can cause cell death. The second transcript is translated to truncated proteins lacking N-terminal transcription activation domain (ΔNp63). ΔNp63 suppresses transcriptional activity of p53 and/or full-length p63 in a dominant-negative manner.

BACKGROUND ART

US Patent Publication No. US20020094547A1 (Invention Title: Differential diagnosis of cancer and other conditions based on expression of p63) relates to a gene product, referred to herein as p63, and to nucleic acids, including the gene, mRNAs, and cDNAs, encoding it, in particular, to methods of using the gene and gene product to diagnose and/or treat certain diseases and disorders such as cancer. The invention also relates to kits which may be used in such diagnostic and treatment methods. The invention also provides methods of distinguishing an epithelial squamous cell carcinoma from a non-epithelial cell carcinoma by detecting p63 nucleic acid or protein expression in cells derived from a carcinoma. In particular, p63 expression indicates that the carcinoma is an epithelial squamous cell carcinoma and the absence of p63 expression indicates that the carcinoma is a non-epithelial cell carcinoma or a carcinoma without squamous differentiation potential.

PCT Publication No. WO04048520A2 (Invention Title: A Transcriptional Target of p63 and p53, and method of use therefor) relates to identification of a novel shared transcriptional target, termed REDD1, that implicates ROS in the p53-dependent DNA damage response and in p63-mediated regulation of epithelial differentiation is disclosed.

EA Patent No. EA0003326B1 (Invention Title: Methods of cancer treating) relates to a method of treating a human subject for cancer comprising the steps of: (a) administering to said subject an organic non-peptide compound that is capable of binding to one or more domains of a human protein of the p53 family under physiological conditions, and stabilizing a functional conformation therein, and (b) permitting said stabilized protein to interact with one or more macromolecules that participate in a wild-type activity of said protein.

U.S. Pat. No. 6,479,285 (Invention Title: p53 as a regulator of cell differentiation) provides methods of the blocking of p53 function in embryonic tissues, and the use of these tissues as screening tools for substances that are capable of overcoming the p53-related block in differentiation. However, there is no example to screen for anti-cancer drugs using biochemical characters of ΔNp63α and exchange of intracellular location.

The present inventors found that ΔNp63α protein was transported from nucleus to cytoplasm during degradation, thereby completing the present invention.

DISCLOSURE

Technical Problem

It is an object of the present invention to develop an effective anticancer-drug screening system in a short time using characters of ΔNp63α, the specific growth regulator of epithelial cell carcinoma.

Technical Solution

The present invention relates to a gene encoding a ΔNp63α transported from the nucleus to the cytoplasm due to contact with potential anticancer-drugs in an epithelial cell carcinoma.

The present invention relates to a ΔNp63α protein transported from the nucleus to the cytoplasm due to contact with potential anticancer-drugs in an epithelial cell carcinoma.

The present invention relates to a ΔNp63α gene transported from the nucleus to the cytoplasm due to injection with potential anticancer-drugs in an epithelial cell carcinoma, and a recombinant vector comprising reporter genes to identify said gene.

The present invention relates to an epithelial cell carcinoma transformed with said recombinant vector.

The present invention relates to screening methods of anticancer-drugs comprising identifying the transportation of a ΔNp63α protein from the nucleus to the cytoplasm due to injection with potential anticancer-drugs in an epithelial cell carcinoma.

The present invention relates to screening methods of anticancer-drugs comprising that said carcinoma is transformed with a ΔNp63α gene and a recombinant vector comprising reporter genes to identify said gene.

The present invention relates to screening methods of anticancer-drugs comprising the steps of:

Cloning a ΔNp63α gene and reporter genes to identify said gene into a vector;

Transforming an epithelial cell carcinoma with said cloning vector and expressing for a certain time;

Contacting said carcinoma with potential materials; and

Identifying the transportation of a ΔNp63α gene location from the nucleus to the cytoplasm.

Figure 2:
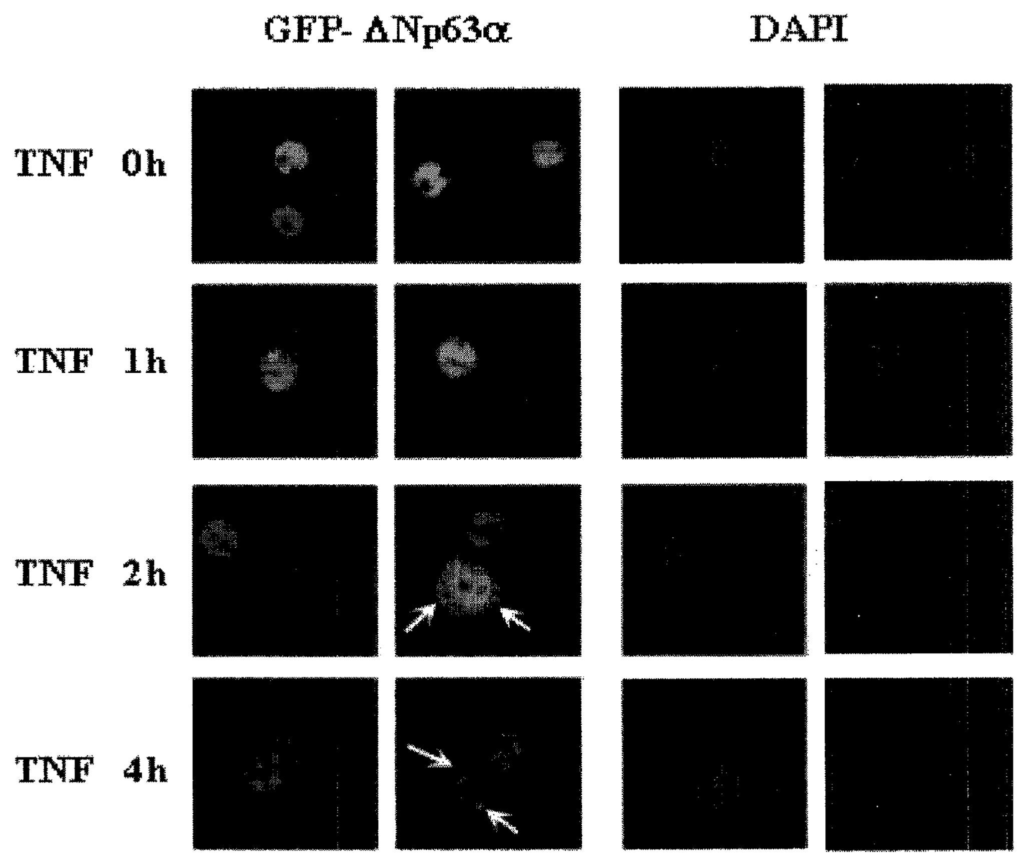

FIG. 2 shows the transportation of the ΔNp63α protein from the nucleus to the cytoplasm after TNF-α treatment.

Figure 3:
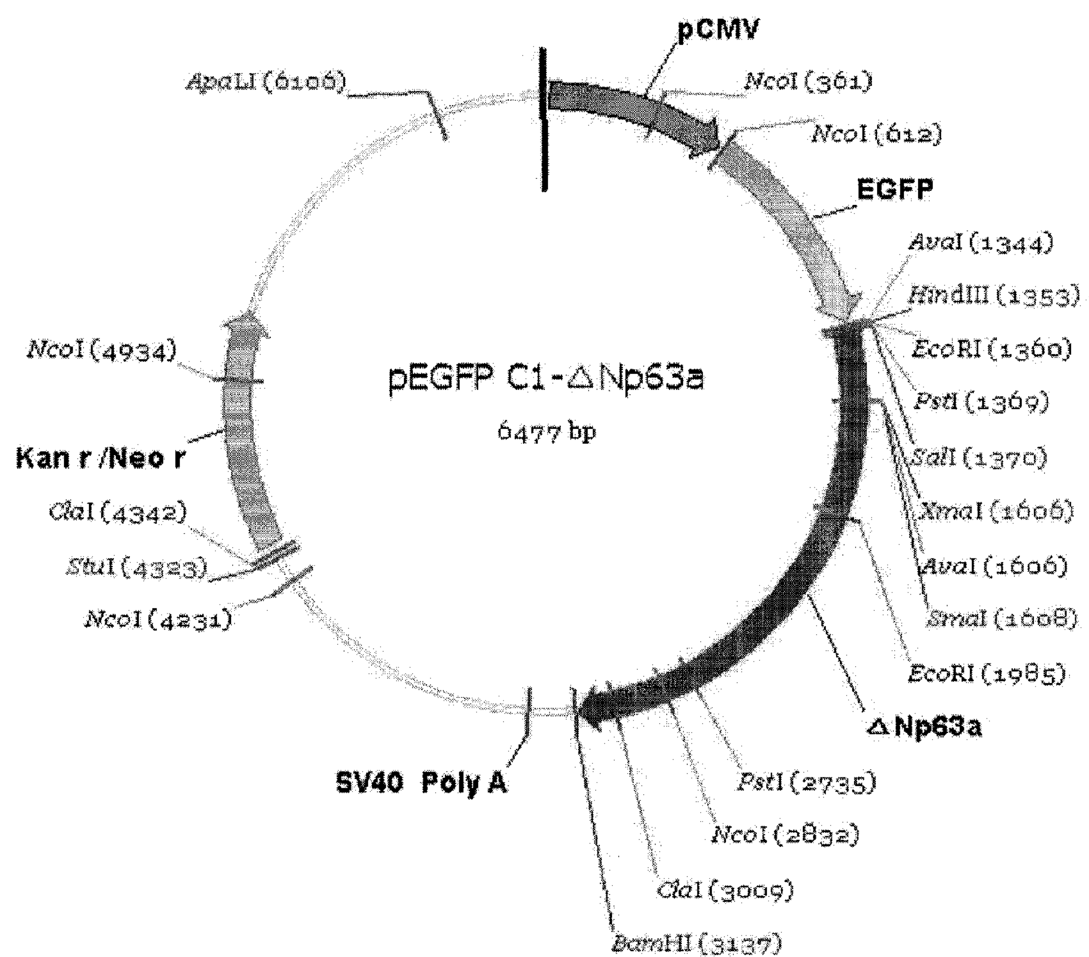

FIG. 3 shows a cleavage map of a recombinant expression vector comprising a ΔNp63α and a reporter gene according to the present invention.

BEST MODE

According to a first aspect, the present invention provides the gene of SEQ ID NO: 1 encoding the ΔNp63α protein which is transported from nucleus to cytoplasm by contacting with potential anticancer-drug in a carcinoma cell derived from epithelial cell. Preferably, cDNA of SEQ ID NO: 2, which resulted in reverse transcription of ΔNp63α mRNA, is used.

As used herein, the term "potential anticancer-drug" refers to effective materials that can kill cancer cells.

According to a second aspect, the present invention provides the ΔNp63α protein of SEQ ID NO: 2, which is transported from nucleus to cytoplasm by contacting with potential anticancer-drug in a carcinoma cell derived from epithelial cell.

According to a third aspect, the present invention provides a expression vector comprising a ΔNp63α gene which is transported from nucleus to cytoplasm by injection with potential anticancer-drug in a carcinoma cell derived from epithelial cell and a reporter gene to identify the expression in of said gene.

As used herein, the term "vector" means a nucleic acid molecule that can carry another nucleic acid bound thereto. As used herein, the term "expression vector" is intended to include a plasmid, cosmid or phage, which can synthesize a protein encoded by a recombinant gene carried by said vector. A preferred vector is a vector that can self-replicate and express a nucleic acid bound thereto.

According to a fourth aspect, the present invention provides a carcinoma cell derived from epithelial cell, which is transformed with said recombinant vector.

As used herein, the term "transformation" means that foreign DNA or RNA is absorbed into cells to change the genotype of the cells.

A suitable carcinoma cell derived from epithelial cell includes HeLa cells, HaCAT, ZR-75-1 or ME180, but is not limited thereto.

According to a fifth aspect, the present invention provides a method of screening for anticancer-drug comprising a step of identifying the transportation of a ΔNp63α protein from nucleus to cytoplasm by injection with potential anticancer-drug in a carcinoma cell derived from epithelial cell.

Methods for identifying the transportation to cytoplasm can be to use reporter genes. But reporter genes are not limited to the specific gene. Any genes that expressed easily detectable products can be used. Suitable reporter genes are well known to those of skill in the art. Examples of reporter genes include other enzyme detection systems such as chloramphenicol acetyl transferase (CAT), luciferase and β-galactosidase, bacterial luciferase, alkaline phosphatase and green fluorescent protein (GFP), but are not limited thereto. Detection of reporter genes is well known to those of skill in the art. In the case of the reporter gene detected by measuring the enzyme activity, the present invention includes steps of supplying with the enzyme and the suitable substrate generally, and detecting reaction products (for example, light produced by luciferase). Also, the present invention can include steps of detecting the presence or absence of gene products easily. Alternatively, the present invention can include quantification of expression level of reporter gene products. Methods for quantification refer to absolute quantification or quantification relative to the expression level of the housekeeping gene. These assays can be performed manually or using high-throughput systems automatically.

High throughput assays for the presence, absence, or quantification of gene expression are well known to those of skill in the art. For example, U.S. Pat. No. 5,559,410 discloses high throughput screening methods for protein and U.S. Pat. No. 5,585,635 discloses high throughput screening methods for nucleic acids binding. Also, U.S. Pat. Nos. 5,576,220 and 5,541,061 describe methods for ligand/antibody binding.

According to a sixth aspect, the present invention provides the method of screening for anticancer-drug comprising the steps of:

Cloning a ΔNp63α gene and a reporter gene to identify the expression of said gene into a vector;

Transforming with said cloned vector into a carcinoma cell derived from epithelial cell and expressing the ΔNp63α gene and the reporter gene;

Contacting said carcinoma cell with potential anticancer-drug; and

Identifying the transportation of the ΔNp63α gene location from nucleus to cytoplasm.

According to a seventh aspect, the present invention provides a kit for performing said screening methods.

Hereinafter, the present invention will be described in further detail with reference to examples. It is to be understood, however, that these examples are for illustrative purposes only and are not to be construed to limit the scope of the present invention.

MODE FOR INVENTION

Reference Example

Figure 1:
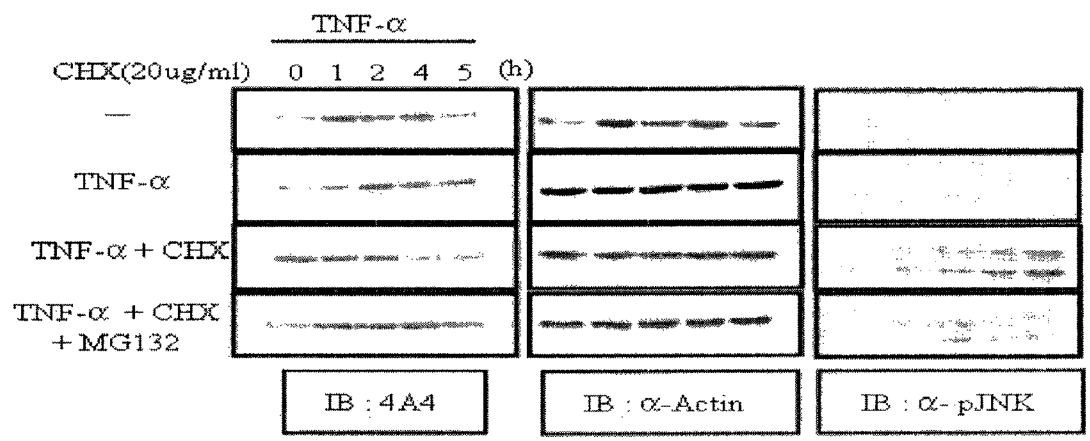
FIG. 1 shows that the amount of ΔNp63α is decreased in the protein level after TNF-α treatment. After TNF-α treatment for 16 hours, cyclohexamide which inhibit protein synthesis was added and the samples were obtained at the indicated time-points and observed for changes of protein stability. As a result, the protein degradation began after 4 hours of treatment with cyclohexamide. And treating with the proteasome inhibitor, MG132 (20 nM) together, the protein wasn't degraded and stabilized even after 4 hours.

Previously, ME180, ΔNp63α overexpressing carcinoma, was treated with TNF-α (tumor necrosis factor-alpha) which induces cell death. Also, the changes of the amount of ΔNp63α protein were observed. As a result, the amount of ΔNp63α decreased rapidly after treatment of TNF-α. It is identified that such degradation of ΔNp63α was proceeded by specific mechanism, that is, by proteasome-mediated mechanism (FIG. 1). Protein degradation pathways could be usually classified in large into two groups, the first one is a degradation pathway by a protease after its polyubiquitination and movement to proteases, and the other one is a degradation pathway by a caspases.

Example 1

Preparation of Recombinant Vectors

A vector pEGFP-C1 (clontech) was used. The pEGFP-C1 vector is easy to detect with fluorescence in case it is expressed because it encodes EGFP (Enhanced green fluorescent protein) gene as a reporter gene. Fusion protein was constructed by subcloning of ΔDNp63α gene of SEQ ID No: 1, the target gene for expression, by using restriction sites of SalI and BamHI within the MCS (multiple cloning site) located at the 3' end of the EGFP gene.

Example 2

Cell Preparation by Transformation with the Recombinant Vector

After preparation of competent *E. coli* DH10B cells using calcium chloride, transformation of *E. coli* was induced with the subcloned pEGFP-ΔNp63α by heat shock methods. At this time, the kanamycin was used as a selectable marker. The resulting colonies were incubated and then their plasmid DNAs were extracted with Miniprep Kit (Intron). The DNA sequence of the extracted plasmid DNAs were analyzed by the DNA sequence analysis.

Example 3

Methods of Screening for Anticancer Drugs

The recombinant vector constructed by the present inventor had fused ΔNp63α next to pEGFP-C1. The advantage of GFP is to observe easily in microscopy because GFP emit the green light at the specific absorbance (Excitation maximum=488 nm; emission maximum=507 nm). Therefore, the carcinoma cell line ME180 which was transformed with subcloned pEGFP-ΔNp63α by using Fugene 6 (Roche) was observed at 488 nm wavelength. GFP is inherently expressed all over the area of cell, however, it was identified that GFP expression was observed only in the nucleus after GFP fused with ΔNp63α. It was observed with microscope by mounting into a mounting solution having DAPI, after TNF-α (tumor necrosis factor-alpha) was treated and then cells were fixed timely.

As a signal of cell death induction, the intracellular location and expression patterns of ΔNp63α were observed. In detail, it was observed variation aspect and cell location of ΔNp63α with a time span, 0 hr, 1 hr, 2 hr and 4 hr with fluorescence microscope, after cloning ΔNp63α gene into the vector expressing Green Fluorescence Protein (GFP), expressing for a certain time by transformation into carcinoma cell, treating TNF-α which induce cell death, carcinoma cells being transformed and then the protein being expressed for a certain time. As a result, it was observed similar aspect of aggreasome, which looks like complex of preteasome, because ΔNp63α, which had been known to locate only in nucleus, moved from nucleus to cytoplasm about 2 hr after treatment of TNF-α (FIG. 2). Therefore, it could be expected that the degradation of ΔNp63α protein is conducted by proteasome in cytoplasm because its location change from nucleus to cytoplasm happen in a short time when cell death is induced.

Industrial Applicability

With a biochemical character of ΔNp63α which exchanges intracellular location, high-throughput screen for anticancer-drug could be achieved than the screening method of anticancer drug in the prior art. The present invention could be used to construct screening system for searching various anticancer drugs except TNF-α used herein, which induce carcinoma specific cell death.

The invention claimed is:

1. A method of screening candidate anticancer drugs comprising the steps of:

(a) contacting an epithelial carcinoma cell with a candidate anticancer drug; and (b) identifying the transportation of ΔNp63α protein from nucleus to cytoplasm upon contact with the candidate anticancer drug.

2. The method according to claim 1, wherein the carcinoma cell is transformed with a recombinant vector expressing ΔNp63α and a a reporter gene to identify expression of ΔNp63α.

3. A method of screening candidate anticancer drugs comprising the steps of:

(a) transforming an epithelial carcinoma cell with a vector expressing ΔNp63α and a reporter gene;

(b) contacting said carcinoma cell with a candidate anticancer drug; and (c) identifying the transportation of ΔNp63α protein from nucleus to cytoplasm in the carcinoma cell upon contact with the candidate anticancer drug.

* * * * *